(12) United States Patent
Hyde et al.

(10) Patent No.: US 8,706,518 B2
(45) Date of Patent: *Apr. 22, 2014

(54) METHODS AND SYSTEMS FOR PRESENTING AN INHALATION EXPERIENCE

(75) Inventors: Roderick A. Hyde, Redmond, WA (US); Robert Langer, Newton, MA (US); Eric C. Leuthardt, St. Louis, MO (US); Robert W. Lord, Seattle, WA (US); Elizabeth A. Sweeney, Seattle, WA (US); Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 474 days.

This patent is subject to a terminal disclaimer.

(21) Appl. No.: 12/383,509

(22) Filed: Mar. 25, 2009

(65) Prior Publication Data

US 2010/0163035 A1 Jul. 1, 2010

Related U.S. Application Data

(63) Continuation-in-part of application No. 12/317,934, filed on Dec. 30, 2008, and a continuation-in-part of application No. 12/319,143, filed on Dec. 31, 2008, and a continuation-in-part of application No. 12/378,284, filed on Feb. 12, 2009, and a continuation-in-part of application No. 12/378,485, filed on Feb. 13, 2009, and a continuation-in-part of application No. 12/380,013, filed on Feb. 20, 2009, and a continuation-in-part of application No. 12/380,108, filed on Feb. 23, 2009, and a continuation-in-part of application No. 12/380,587, filed on Feb. 27, 2009, and a continuation-in-part of application No. 12/380,679, filed on Mar. 2, 2009.

(51) Int. Cl.
*G06Q 10/00* (2012.01)
*G06F 19/00* (2011.01)
*A61M 11/00* (2006.01)

(52) U.S. Cl.
USPC .......................... 705/2; 702/19; 128/200.15

(58) Field of Classification Search
USPC ............................................................. 705/2
See application file for complete search history.

(56) References Cited

U.S. PATENT DOCUMENTS 3,946,726 A 3/1976 Pikul
4,652,261 A 3/1987 Mech et al.
4,784,162 A 11/1988 Ricks et al.
(Continued)

FOREIGN PATENT DOCUMENTS

EP 0328145 8/1989

OTHER PUBLICATIONS

Dog Health: Asthma, http://www.animalhospitals-usa.com/dogs/asthma.html, 2009, Publisher: Harper Collins.
(Continued)

*Primary Examiner* — Hiep V Nguyen

(57) ABSTRACT

Methods, computer program products, and systems are described that include accepting at least one indication of use of an inhalation device configured to dispense a bioactive agent to an individual and presenting at Least one artificial sensory experience to monitor at Least one side effect of the bioactive agent on the individual.

34 Claims, 38 Drawing Sheets

(56) References Cited

U.S. PATENT DOCUMENTS

| | | | |
|---|---|---|---|
| 4,974,729 A | 12/1990 | Steinnagel | |
| 5,071,704 A | 12/1991 | Fischel-Ghodsian | |
| 5,455,043 A | 10/1995 | Fischel-Ghodsian | |
| 5,458,853 A | 10/1995 | Porter et al. | |
| 5,487,378 A | 1/1996 | Robertson et al. | |
| 5,546,943 A | 8/1996 | Gould | |
| 5,610,674 A * | 3/1997 | Martin | 352/85 |
| 5,709,863 A | 1/1998 | Pageat | |
| 5,725,472 A | 3/1998 | Weathers | |
| 5,822,726 A | 10/1998 | Taylor et al. | |
| 5,842,467 A | 12/1998 | Greco | |
| 5,954,641 A | 9/1999 | Kehr et al. | |
| 6,026,807 A | 2/2000 | Puderbaugh et al. | |
| 6,067,523 A | 5/2000 | Bair et al. | |
| 6,168,562 B1 | 1/2001 | Miller et al. | |
| 6,223,744 B1 | 5/2001 | Garon | |
| 6,280,383 B1 | 8/2001 | Damadian | |
| 6,314,384 B1 | 11/2001 | Goetz | |
| 6,315,719 B1 | 11/2001 | Rode et al. | |
| 6,338,338 B1 | 1/2002 | Brace | |
| 6,411,905 B1 | 6/2002 | Guoliang et al. | |
| 6,425,764 B1 | 7/2002 | Lamson | |
| 6,443,153 B1 | 9/2002 | Viljanen et al. | |
| 6,491,643 B2 | 12/2002 | Katzman et al. | |
| 6,500,862 B1 | 12/2002 | Zanello | |
| 6,513,523 B1 | 2/2003 | Izuchukwu et al. | |
| 6,585,519 B1 | 7/2003 | Jenkins et al. | |
| 6,609,068 B2 | 8/2003 | Cranley et al. | |
| 6,647,358 B2 | 11/2003 | Grass et al. | |
| 6,684,880 B2 | 2/2004 | Trueba | |
| 6,780,171 B2 | 8/2004 | Gabel et al. | |
| 6,783,753 B2 | 8/2004 | Rabinowitz et al. | |
| 6,860,239 B1 | 3/2005 | Begun | |
| 6,889,687 B1 | 5/2005 | Olsson | |
| 6,978,212 B1 | 12/2005 | Sunshine | |
| 6,981,502 B2 | 1/2006 | McCormick et al. | |
| 7,044,911 B2 | 5/2006 | Drinan et al. | |
| 7,155,680 B2 | 12/2006 | Akazawa et al. | |
| 7,198,044 B2 * | 4/2007 | Trueba | 128/200.16 |
| 7,353,065 B2 * | 4/2008 | Morrell | 607/45 |
| 7,373,377 B2 | 5/2008 | Altieri | |
| 7,383,837 B2 * | 6/2008 | Robertson et al. | 128/200.23 |
| 7,427,417 B2 | 9/2008 | Jendrucko et al. | |
| 7,447,541 B2 | 11/2008 | Huiku et al. | |
| 7,720,696 B1 | 5/2010 | Berger et al. | |
| 8,068,983 B2 | 11/2011 | Vian et al. | |
| 2001/0006939 A1 | 7/2001 | Niven et al. | |
| 2001/0034023 A1 * | 10/2001 | Stanton et al. | 435/6 |
| 2002/0084996 A1 | 7/2002 | Temkin et al. | |
| 2003/0032638 A1 | 2/2003 | Kim et al. | |
| 2003/0036683 A1 | 2/2003 | Kehr et al. | |
| 2003/0114475 A1 | 6/2003 | Fox et al. | |
| 2004/0107961 A1 | 6/2004 | Trueba | |
| 2004/0116784 A1 | 6/2004 | Gavish | |
| 2004/0254501 A1 | 12/2004 | Mault | |
| 2005/0054942 A1 | 3/2005 | Melker et al. | |
| 2005/0115561 A1 | 6/2005 | Stahmann et al. | |
| 2005/0220843 A1 | 10/2005 | DeWitt et al. | |
| 2006/0031099 A1 | 2/2006 | Vitello et al. | |
| 2006/0058694 A1 | 3/2006 | Clark et al. | |
| 2006/0207596 A1 | 9/2006 | Lane | |
| 2007/0068514 A1 | 3/2007 | Giroux | |
| 2007/0068515 A1 | 3/2007 | Churchill | |
| 2007/0112624 A1 | 5/2007 | Jung et al. | |
| 2007/0123783 A1 | 5/2007 | Chang | |
| 2008/0014566 A1 | 1/2008 | Chapman et al. | |
| 2008/0038701 A1 | 2/2008 | Booth et al. | |
| 2008/0087279 A1 | 4/2008 | Tieck et al. | |
| 2008/0142010 A1 | 6/2008 | Weaver et al. | |
| 2008/0172044 A1 | 7/2008 | Shelton | |
| 2008/0209289 A1 | 8/2008 | Farnsworth et al. | |
| 2008/0230057 A1 | 9/2008 | Sutherland | |
| 2008/0294012 A1 | 11/2008 | Kurtz et al. | |
| 2008/0318913 A1 | 12/2008 | Fox et al. | |
| 2009/0171259 A1 | 7/2009 | Soerensen et al. | |
| 2009/0223249 A1 | 9/2009 | Julkowski et al. | |
| 2009/0306741 A1 * | 12/2009 | Hogle et al. | 607/54 |
| 2011/0226242 A1 | 9/2011 | Von Hollen et al. | |

OTHER PUBLICATIONS

Karen Vail, Chemical and Nonchemical Management of Fleas, 1999, Publisher: facilities.lipscomb.edu/media.asp?SID=145&UKEY=7743, Published in: US.

Julian R. Yates III, Ctenocephalides felis (Bouche), http://www.extento.hawaii.edu/kbase/urban/site/catflea.htm, , Published in: US.

Mehlhorn, et al., Effects of Imidacloprid on Adult and Larval Stages of the Flea Ctenocephalides Felis After In Vivo and In Vitro Application: a Light- and Electron-Microscopy Study; Parasitology Research, 1999, pp. 625-637, vol. 85, No. 8-9, Published in: US.

Susan Little, Feline Asthma, The Winn Feline Foundation, 2003, Publisher: http://www.winnfelinehealth.org/health/asthma.html, Published in: US.

Placerville Veterinary Clinic, Flea Control, www://placervillevet.com/flea_control.htm, 1995-2008, Published in: US.

Cranshaw, et al., Fleas and Plague, http://www.ext.colostate.edu/pubs/insect/05600.html, 2008, Published in: US.

Jeff Feinman, VMD,CVH, Fleas and Ticks, http://www.homevet.com/petcare/fleas.html, 1996-1997, Published in: US.

J.B. Siddall, Insect Growth Regulators and Insect Control: A Critical Appraisal, Environmental Health Perspectives, Apr. 1976, pp. 119-126, vol. 14, Published in: US.

Label Instructions Tightened on Flea & Tick Control Products for Pets, http://www.epa.gov/pesticides/factsheets/hartzq_a.htm, Nov. 2002, Publisher: Environmental Protection Agency, Published in: US.

T. Roy Fukuto, Mechanism of Action of Organophosphorus and Carbamate Insecticides, Environmental Health Perspectives, Jul. 1990, pp. 245-254, vol. 87, Published in: US.

M. Tomizawa, et al., Neonicotinoid Insecticide Toxicology: Mechanisms of Selective Action, Annual Review of Pharmacology and Toxicology, Feb. 2005, pp. 247-268, vol. 45.

C.J. Harland, et al., Remote Detection of Human Electroencephalograms Using Ultrahigh Input Impedance Electric Potential Sensors, Applied Physics Letters, Oct. 21, 2002, pp. 3284-3286, vol. 81, No. 17, Publisher: American Institute of Physics.

Mencke, et al., Therapy and Prevention of Parasitic Insects in Veterinary Medicine Using Imidacloprid, Current Topics in Medicinal Chemistry, Jul. 2002, vol. 2, No. 7.

Hovda, et al., Toxicology of Newer Pesticides for Use in Dogs and Cats, Vet Clin North Am Small Anim. Pract., Mar. 2002, pp. 455-567, vol. 32, No. 2.

U.S. Appl. No. 12/383,819, Hyde et al.
U.S. Appl. No. 12/384,104, Hyde et al.
U.S. Appl. No. 12/384,203, Hyde et al.
U.S. Appl. No. 12/386,574, Hyde et al.
U.S. Appl. No. 12/386,669, Hyde et al.
U.S. Appl. No. 12/387,057, Hyde et al.
U.S. Appl. No. 12/387,151, Hyde et al.
U.S. Appl. No. 12/387,321, Hyde et al.
U.S. Appl. No. 12/387,472, Hyde et al.

Usmani, Omar S. et al.; "Glucocorticoid Receptor Nuclear Translocation in Airway Cells After Inhaled Combination Therapy"; American Journal of Respiratory and Critical Care Medicine; bearing a date of Apr. 28, 2005; pp. 704-712; vol. 172; located at http://ajrccm.atsjournals.org/cgi/content/abstract/172/6/704 [abstract only].

"Fear of Flying"; The Virtual Reality Medical Center (VRMC); Bearing a date of Jan. 1, 2007, p. 1; located at: http://www.vrphobia.com/therapy.htm.

* cited by examiner

600

Start 610
accepting an indication of a bioactive agent-dispensing inhalation device 620
presenting an indication of an artificial sensory experience at least partially based on accepting an indication of a bioactive agent-dispensing inhalation device Finish

Start

610
accepting an indication of a bioactive agent-dispensing inhalation device

| 702 accepting an indication of a bioactive agent-dispensing inhalation device configured to interface with a computing device | 706 accepting an indication of a bioactive agent-dispensing inhalation collar | 708 accepting an indication of a bioactive agent-dispensing virtual-reality headset |

704
accepting an indication of a bioactive agent-dispensing inhalation device configured to interface wirelessly with a computing device

620
presenting an indication of an artificial sensory experience at least partially based on accepting an indication of a bioactive agent-dispensing inhalation device Finish

FIG. 7

```
                            600
                             ↙
         ( Start )
             │
┌────────────┴──────────────────────────────────────────────┐
│ 610                                                        │
│ accepting an indication of a bioactive agent-dispensing inhalation device │
│ ┌─────────────┐ ┌─────────────────────────────────────────┐│
│ │ 802         │ │ 804                                     ││
│ │ accepting at│ │ accepting an indication of a medicine-dispensing ││
│ │ least one of a│ │ inhalation device                     ││
│ │ bioactive   │ │ ┌─────────────────────────────────────┐ ││
│ │ agent dosing│ │ │ 806                                 │ ││
│ │ schedule or a│ │ │ accepting an indication of a prescription medicine- │ ││
│ │ bioactive   │ │ │ dispensing inhalation device        │ ││
│ │ agent       │ │ │ ┌─────────────────────────────────┐ │ ││
│ │ administration│ │ │ │ 808                             │ │ ││
│ │ schedule    │ │ │ │ accepting an indication of at least one of a │ │ ││
│ │             │ │ │ │ steroid, a bronchodilator, menthol, nitrous │ │ ││
│ │             │ │ │ │ oxide, a benzodiazepine, an anti-allergic agent, │ │ ││
│ │             │ │ │ │ a muscle relaxant, or anesthetic │ │ ││
│ │             │ │ │ └─────────────────────────────────┘ │ ││
│ │             │ │ └─────────────────────────────────────┘ ││
│ └─────────────┘ └─────────────────────────────────────────┘│
└────────────┬──────────────────────────────────────────────┘
             │
┌────────────┴──────────────────────────────────────────────┐
│ 620                                                        │
│ presenting an indication of an artificial sensory experience at least partially │
│ based on accepting an indication of a bioactive agent-dispensing inhalation │
│ device                                                     │
└────────────┬──────────────────────────────────────────────┘
             │
         ( Finish )
```

FIG. 8

```
                                    600
                                   ↙
                    ┌─────┐
                    │Start│
                    └──┬──┘
                       │
┌──────────────────────┴──────────────────────────────┐
│ 610                                                  │
│ accepting an indication of a bioactive agent-dispensing inhalation device │
└──────────────────────┬──────────────────────────────┘
                       │
┌──────────────────────┴──────────────────────────────────────────────┐
│ 620                                                                  │
│ presenting an indication of an artificial sensory experience at least partially │
│ based on accepting an indication of a bioactive agent-dispensing inhalation │
│ device                                                               │
│ ┌──────────────────────────────────────────────────────────────────┐ │
│ │ 1002 presenting an indication of a prescribed artificial sensory experience │
│ ├─────────────────┬────────────────────────────────────────────────┤ │
│ │ 1004            │ 1006                                            │ │
│ │ presenting   an │ presenting an indication of at least one effect of the │
│ │ indication of a │ prescribed artificial sensory experience        │ │
│ │ virtual   world ├────────────────────────┬───────────────────────┤ │
│ │ experience,   a │ 1008                   │ 1010                  │ │
│ │ massively       │ presenting an indication│ presenting an indication │
│ │ multiplayer     │ of at least one desired │ of at least one expected │
│ │ online game, or │ effect of the prescribed│ adverse effect of the │ │
│ │ a      learning │ artificial     sensory │ prescribed  artificial│ │
│ │ tutorial        │ experience             │ sensory experience    │ │
│ └─────────────────┴────────────────────────┴───────────────────────┘ │
└──────────────────────┬──────────────────────────────────────────────┘
                       │
                    ┌──┴───┐
                    │Finish│
                    └──────┘
```

Start 610
accepting an indication of a bioactive agent-dispensing inhalation device 620
presenting an indication of an artificial sensory experience at least partially based on accepting an indication of a bioactive agent-dispensing inhalation device

| 1002 presenting an indication of a prescribed artificial sensory experience |

| 1102 presenting an indication of at least one time period of an expected change in bioactive agent effectiveness | 1104 presenting an indication of at least one time period of an expected change in bioactive agent blood concentration | 1106 recommending an artificial sensory experience administration schedule |

Finish

FIG. 11

```
                                    600
                                   ╱
                    ┌─────┐  ←
                    │Start│
                    └──┬──┘
┌──────────────────────┴──────────────────────────────┐
│ 610                                                  │
│ accepting an indication of a bioactive agent-dispensing inhalation device │
└──────────────────────┬──────────────────────────────┘
┌──────────────────────┴──────────────────────────────┐
│ 620                                                  │
│ presenting an indication of an artificial sensory experience at least partially │
│ based on accepting an indication of a bioactive agent-dispensing inhalation │
│ device                                               │
│  ┌ ─ ─ ─ ─ ─ ─ ─ ─ ─ ─ ─ ─ ─ ─ ─ ─ ─ ─ ─ ─ ─ ─ ─ ┐ │
│  │ 1402                                           │ │
│  │ presenting the indication to a third party     │ │
│  │  ┌ ─ ─ ─ ─ ─ ─ ─ ─ ─ ─ ┐ ┌ ─ ─ ─ ─ ─ ─ ─ ─ ─ ┐│ │
│  │  │ 1404               │ │ 1406              │ │ │
│  │  │ presenting the indication to a │ │ selectively presenting the │ │ │
│  │  │ health care provider │ │ indication only to the individual │ │ │
│  │  └ ─ ─ ─ ─ ─ ─ ─ ─ ─ ─ ┘ └ ─ ─ ─ ─ ─ ─ ─ ─ ─ ┘│ │
│  └ ─ ─ ─ ─ ─ ─ ─ ─ ─ ─ ─ ─ ─ ─ ─ ─ ─ ─ ─ ─ ─ ─ ─ ┘ │
└──────────────────────┬──────────────────────────────┘
                    ┌──┴───┐
                    │Finish│
                    └──────┘
```

Start 610
accepting an indication of a bioactive agent-dispensing inhalation device 620
presenting an indication of an artificial sensory experience at least partially based on accepting an indication of a bioactive agent-dispensing inhalation device 1502
accepting an indication of an albuterol-dispensing collar configured to be worn proximate to the neck of an individual, accepting a prescribed administration schedule of the albuterol-dispensing collar for the individual, and presenting a prescription for engagement of the individual with a virtual world experience configured to teach the individual a deep breathing technique Finish

Start 2210
accepting at least one indication of use of an inhalation device configured to dispense a bioactive agent to an individual 2220
presenting at least one artificial sensory experience to monitor at least one side effect of the bioactive agent on the individual Finish

FIG. 22

```
                    2200
      ┌─────┐      ↙
      │Start│
      └──┬──┘
```

2210
accepting at least one indication of use of an inhalation device configured to dispense a bioactive agent to an individual > 2302
> accepting an indication of a bioactive agent-dispensing inhalation device configured to interface with a computing device
>
> > 2304
> > accepting an indication of a bioactive agent-dispensing inhalation device configured to interface wirelessly with a computing device

2220
presenting at least one artificial sensory experience to monitor at least one side effect of the bioactive agent on the individual

```
      ┌──────┐
      │Finish│
      └──────┘
```

FIG. 23

```
                    ┌─────┐
                    │Start│                    2200
                    └──┬──┘                 ↙
                       │
┌──────────────────────┴──────────────────────────────────┐
│ 2210                                                    │
│ accepting at least one indication of use of an inhalation device │
│ configured to dispense a bioactive agent to an individual │
│ ┌─────────────────┐  ┌─────────────────────────────┐    │
│ │ 2402            │  │ 2404                        │    │
│ │ accepting an    │  │ accepting an indication of a│    │
│ │ indication of a │  │ bioactive agent-dispensing virtual- │
│ │ bioactive agent-│  │ reality headset             │    │
│ │ dispensing inhalation │                          │    │
│ │ collar          │  │ ┌─────────────────────────┐ │    │
│ │                 │  │ │ 2406                    │ │    │
│ │                 │  │ │ accepting at least one of a │ │
│ │                 │  │ │ bioactive agent dosing  │ │    │
│ │                 │  │ │ schedule or a bioactive │ │    │
│ │                 │  │ │ agent administration    │ │    │
│ │                 │  │ │ schedule                │ │    │
│ │                 │  │ └─────────────────────────┘ │    │
│ └─────────────────┘  └─────────────────────────────┘    │
└──────────────────────┬──────────────────────────────────┘
                       │
┌──────────────────────┴──────────────────────────────────┐
│ 2220                                                    │
│ presenting at least one artificial sensory experience to monitor at │
│ least one side effect of the bioactive agent on the individual │
└──────────────────────┬──────────────────────────────────┘
                       │
                   ┌───┴────┐
                   │ Finish │
                   └────────┘

FIG. 24
```

```
                    ┌─ 2200
             Start

┌──────────────────────────────────────────────────────────────┐
│ 2210                                                         │
│ accepting at least one indication of use of an inhalation   │
│ device configured to dispense a bioactive agent to an        │
│ individual                                                   │
└──────────────────────────────────────────────────────────────┘

┌──────────────────────────────────────────────────────────────┐
│ 2220                                                         │
│ presenting at least one artificial sensory experience to     │
│ monitor at least one side effect of the bioactive agent on   │
│ the individual                                               │
│                                                              │
│  ┌─────────────────────┐  ┌──────────────────────────────┐  │
│  │ 2702                │  │ 2704                         │  │
│  │ receiving data from │  │ presenting a sensate         │  │
│  │ an automated        │  │ experience                   │  │
│  │ medical device      │  │                              │  │
│  │                     │  │  ┌────────────────────────┐  │  │
│  │                     │  │  │ 2706                   │  │  │
│  │                     │  │  │ presenting at least    │  │  │
│  │                     │  │  │ one of an olfactory    │  │  │
│  │                     │  │  │ stimulus, a haptic     │  │  │
│  │                     │  │  │ stimulus, a visual     │  │  │
│  │                     │  │  │ stimulus, an auditory  │  │  │
│  │                     │  │  │ stimulus, or a taste   │  │  │
│  │                     │  │  │ stimulus for monitoring│  │  │
│  │                     │  │  │ the at least one       │  │  │
│  │                     │  │  │ desired effect of the  │  │  │
│  │                     │  │  │ bioactive agent        │  │  │
│  │                     │  │  └────────────────────────┘  │  │
│  └─────────────────────┘  └──────────────────────────────┘  │
└──────────────────────────────────────────────────────────────┘

Finish
```

Start 2210
accepting at least one indication of use of an inhalation device configured to dispense a bioactive agent to an individual 2220
presenting at least one artificial sensory experience to monitor at least one side effect of the bioactive agent on the individual 2802
presenting an artificial sensory experience implemented on a mobile device 2804
presenting a virtual world, a modification to a virtual world, a computer game, a modification to a computer game, a website, a modification to a website, an online course, or a modification to an online course Finish

Start 2210
accepting at least one indication of use of an inhalation device configured to dispense a bioactive agent to an individual 2220
presenting at least one artificial sensory experience to monitor at least one side effect of the bioactive agent on the individual > 2902
> presenting an artificial sensory experience to monitor at least one of physical activity, body weight, body mass index, heart rate, blood oxygen level, or blood pressure temporally associated with an artificial sensory experience Finish

FIG. 29

```
                                    2200
         ┌─────┐                   ↙
         │Start│
         └──┬──┘

┌─────────────────────────────────────────────────────────────┐
│ 2210                                                         │
│ accepting at least one indication of use of an inhalation   │
│ device configured to dispense a bioactive agent to an       │
│ individual                                                   │
└─────────────────────────────────────────────────────────────┘

┌─────────────────────────────────────────────────────────────┐
│ 2220                                                         │
│ presenting at least one artificial sensory experience to    │
│ monitor at least one side effect of the bioactive agent on  │
│ the individual                                               │
│                                                              │
│  ┌─ 3202 ──────────────────┐  ┌─ 3204 ──────────────────┐  │
│  │ monitoring at least one │  │ monitoring at least one │  │
│  │ of visual field test    │  │ of body movement test   │  │
│  │ function output, eye    │  │ function output or      │  │
│  │ movement test function  │  │ motor skill test        │  │
│  │ output, pupil movement  │  │ function output         │  │
│  │ test function output,   │  │                         │  │
│  │ face pattern test       │  │                         │  │
│  │ function output,        │  │                         │  │
│  │ hearing test function   │  │                         │  │
│  │ output, or voice test   │  │                         │  │
│  │ function output         │  │                         │  │
│  └─────────────────────────┘  └─────────────────────────┘  │
└─────────────────────────────────────────────────────────────┘

┌──────┐
         │Finish│
         └──────┘
```

╭─────╮
                        │Start│
                        ╰─────╯
                           │
┌──────────────────────────┴──────────────────────────────┐
│2210                                                      │
│accepting at least one indication of use of an inhalation│
│device configured to dispense a bioactive agent to an    │
│individual                                                │
└──────────────────────────┬──────────────────────────────┘
┌──────────────────────────┴──────────────────────────────┐
│2220                                                      │
│presenting at least one artificial sensory experience to │
│monitor at least one side effect of the bioactive agent  │
│on the individual                                         │
│                                                          │
│  ┌─ ─ ─ ─ ─ ─ ─ ─ ─ ─ ┐  ┌─ ─ ─ ─ ─ ─ ─ ─ ─ ─ ─ ─ ┐    │
│  │ 3302               │  │ 3304                    │    │
│  │ recording at least │  │ accepting an indication │    │
│  │ one monitored      │  │ of a collar configured  │    │
│  │ effect of the      │  │ to dispense a           │    │
│  │ bioactive agent    │  │ bronchodilator to an    │    │
│  │                    │  │ individual and          │    │
│  │                    │  │ presenting a virtual    │    │
│  │                    │  │ world to monitor an     │    │
│  │                    │  │ individual's            │    │
│  │                    │  │ hypertension in response│    │
│  │                    │  │ to administration of the│    │
│  │                    │  │ bronchodilator          │    │
│  └─ ─ ─ ─ ─ ─ ─ ─ ─ ─ ┘  └─ ─ ─ ─ ─ ─ ─ ─ ─ ─ ─ ─ ┘    │
└──────────────────────────┬──────────────────────────────┘
                        ╭──┴───╮
                        │Finish│
                        ╰──────╯
```

FIG. 33

METHODS AND SYSTEMS FOR PRESENTING AN INHALATION EXPERIENCE

CROSS-REFERENCE TO RELATED APPLICATIONS

The present application is related to and claims the benefit of the earliest available effective filing date(s) from the following Listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of United States patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Dec. 30, 2008, application Ser. No. 12/317,934, which is currently co-pending, or is an application of which a currently co-pending application is entitled to the benefit of the filing date.

For purposes of the USPTO extra-statutory requirements, the present application constitutes a continuation-in-part of United States patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Dec. 31, 2008, application Ser. No. 12/319,143, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 12, 2009, application Ser. No. 12/378,284, which is currently co-pending, or is an application of which a currently co-pending application is entitled to the benefit of the filing date.

For purposes of the USPTO extra-statutory requirements, the present application constitutes a continuation-in-part of United States patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 13, 2009, application Ser. No. 12/378,485, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 20, 2009, application Ser. No. 12/380,013, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 23, 2009, application Ser. No. 12/380,108, which is currently co-pending, or is an application of which a currently co-pending application is entitled to the benefit of the filing date.

For purposes of the USPTO extra-statutory requirements, the present application constitutes a continuation-in-part of U.S. patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Feb. 27, 2009, application Ser. No. 12/380,587, which is currently co-pending, or is an application of which a currently co-pending application is entitled to the benefit of the filing date.

For purposes of the USPTO extra-statutory requirements, the present application constitutes a continuation-in-part of United States patent application entitled METHODS AND SYSTEMS FOR PRESENTING AN INHALATION EXPERIENCE, naming RODERICK A. HYDE; ROBERT LANGER; ERIC C. LEUTHARDT; ROBERT W. LORD; ELIZABETH A. SWEENEY; CLARENCE T. TEGREENE; AND LOWELL L. WOOD as inventors, filed Mar. 2, 2009, application Ser. No. 12/380,679, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to methods and systems for an inhaled bioactive agent combined with an artificial sensory experience.

SUMMARY

In one aspect, a method includes but is not limited to accepting at least one indication of use of an inhalation device configured to dispense a bioactive agent to an individual and presenting at least one artificial sensory experience to monitor at least one side effect of the bioactive agent on the individual. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to means for accepting at least one indication of use of an inhalation device configured to dispense a bioactive agent to an individual and means for presenting at least one artificial sensory experience to monitor at least one side effect of the bioactive agent on the individual. In addition to the foregoing, other method aspects are described in the claims, drawings, and text forming a part of the present disclosure.

In one aspect, a system includes but is not limited to circuitry for accepting at least one indication of use of an inhalation device configured to dispense a bioactive agent to an individual and circuitry for presenting at least one artificial sensory experience to monitor at least one side effect of the bioactive agent on the individual. In addition to the foregoing, other method aspects are described in the claims, drawings, and text forming a part of the present disclosure.

In one aspect, a computer program product includes but is not limited to a signal-bearing medium bearing one or more instructions for accepting at least one indication of use of an inhalation device configured to dispense a bioactive agent to an individual and one or more instructions for presenting at least one artificial sensory experience to monitor at least one side effect of the bioactive agent on the individual. In addition to the foregoing, other method aspects are described in the claims, drawings, and text forming a part of the present disclosure.

In one aspect, a system includes but is not limited to a computing device and instructions that when executed on the computing device cause the computing device to accept at least one indication of use of an inhalation device configured to dispense a bioactive agent to an individual and present at least one artificial sensory experience to monitor at least one side effect of the bioactive agent on the individual. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 6 illustrates an operational flow representing example operations related to combining an inhaled bioactive agent and an artificial sensory experience.

FIG. 7 illustrates an alternative embodiment of the operational flow of FIG. 6.

FIG. 8 illustrates an alternative embodiment of the operational flow of FIG. 6.

FIG. 10 illustrates an alternative embodiment of the operational flow of FIG. 6.

FIG. 11 illustrates an alternative embodiment of the operational flow of FIG. 6.

FIG. 14 illustrates an alternative embodiment of the operational flow of FIG. 6.

FIG. 15 illustrates an alternative embodiment of the operational flow of FIG. 6.

FIG. 22 illustrates an operational flow representing example operations related to combining an inhaled bioactive agent and an artificial sensory experience.

FIG. 23 illustrates an alternative embodiment of the operational flow of FIG. 22.

FIG. 24 illustrates an alternative embodiment of the operational flow of FIG. 22.

FIG. 27 illustrates an alternative embodiment of the operational flow of FIG. 22.

FIG. 28 illustrates an alternative embodiment of the operational flow of FIG. 22.

FIG. 29 illustrates an alternative embodiment of the operational flow of FIG. 22.

FIG. 32 illustrates an alternative embodiment of the operational flow of FIG. 22.

FIG. 33 illustrates an alternative embodiment of the operational flow of FIG. 22.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates system 100 for accepting an indication of at least one health-related condition and/or presenting an indication of at least one artificial sensory experience and an indication of at least one inhalation therapy at least partially based on the accepting at least one indication of a health-related condition. The system 100 may include accepter module 102, presenter module 104, and/or administration unit 106. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, system 3200 may include mobile device 132.

FIG. 2 illustrates system 100 for accepting an indication of at least one health-related condition and/or presenting an indication of at least one artificial sensory experience and an indication of at least one inhalation therapy at least partially based on the accepting at least one indication of a health-related condition. The system 100 may include accepter module 102, presenter module 104, administration unit 106, and/or monitoring unit 3202. Accepter module 102 may receive and/or transmit information and/or data to and/or from user 118, database 122, presenter module 3410, output device 130, and/or health care provider 136. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, mobile device 132 may communicate with accepter module 102, presenter module 104, healthcare provider 136, user 118, individual 134, monitoring unit 3202, and/or administration unit 3222.

FIG. 3 illustrates an exemplary inhalation device 110. An exemplary inhalation device 110 may include a closure device, a transducer, and/or a dispensing reservoir. Inhalation device 110 may include, for example, a collar, a necklace, and/or a bracelet. Inhalation device 110 may include tubing, a chain, a polymer, a metal, a textile, and may be solid and/or hollow. Closure device 302 may include a buckle, Velcro, a snap, a clasp, a lock, a coupler, elastic, and/or magnets. Transducer 304 may include a blood glucose monitor, a blood oxygen monitor, means for sending a signal to a reservoir to dispense medication, such as an antenna, means for powering the unit, such as a battery, memory, and/or a computer processor. Dispensing reservoir 306 may include means for power, such as a battery, means for receiving conditional input, such as a processor and/or memory, means for dispensing a bioactive agent in aerosol, dust and/or vapor form, such as a nebulizer, a sprayer, and/or a nozzle. Additionally, the dispensing reservoir 306 may be removable and/or refillable.

FIG. 4 further illustrates system 100 including accepter module 102 and/or presenter module 104. Accepter module 102 may include computer interfacing accepter module 402, inhalation collar indication accepter module 406, headset indication accepter module 408, schedule accepter module 410, inhalation device accepter module 412, unregulated device accepter module 418, and/or recreational device accepter module 420. Computer interfacing accepter module 402 may include wireless accepter module 404. Inhalation device accepter module 412 may include prescription medicine device accepter module 414 and/or prescription medicine accepter module 416. Recreational device accepter module 420 may include recreational compound indication accepter module 422.

FIG. 5 illustrates system 100 including accepter module 102 and/or presenter module 104. Presenter module 104 may include prescription artificial sensory experience presenter module 424, algorithm utilizer module 440, medical history indication presenter module 444, experimental indiciation presenter module 446, reference tool indication presenter module 448, output device presenter module 450, and/or third party presenter module 456. Prescription artificial sensory experience presenter module 424 may include artificial sensory experience presenter module 426, artificial sensory experience effect presenter module 428, effectiveness change presenter module 434, concentration change presenter module 436, and/or recommender module 438. Artificial sensory experience effect presenter module 428 may include artificial sensory experience desired effect presenter module 430 and/or artificial sensory experience adverse effect presenter module 432. Algorithm utilizer module 440 may include contraindication algorithm utilizer module 442. Output device presenter module 450 may include user interface presenter module 452 and/or mobile device presenter module 454.

Figure 1:
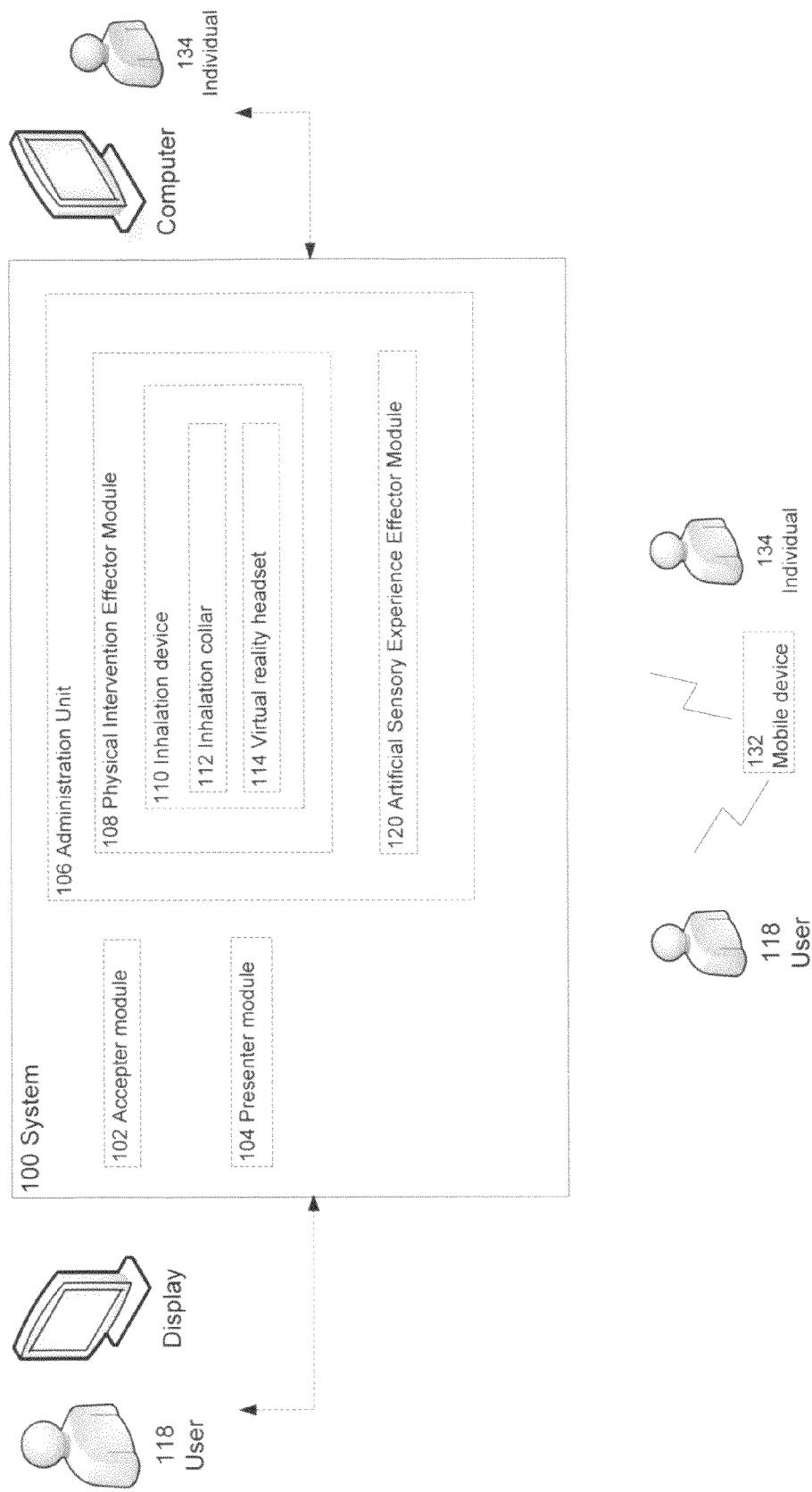
FIG. 1 illustrates an exemplary environment in which one or more technologies may be implemented.
Figure 2:
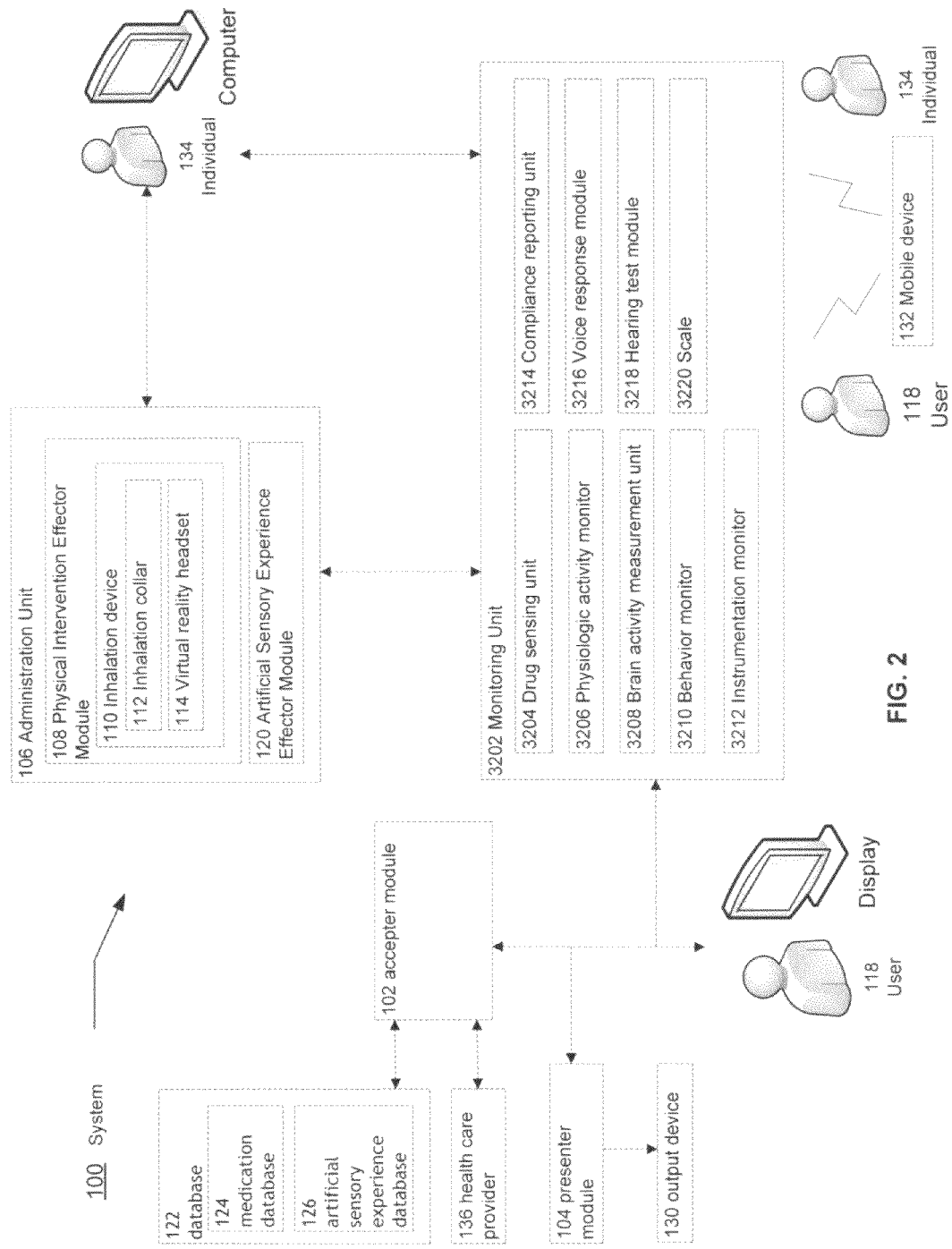
FIG. 2 illustrates an exemplary environment in which one or more technologies may be implemented.
Figure 3:
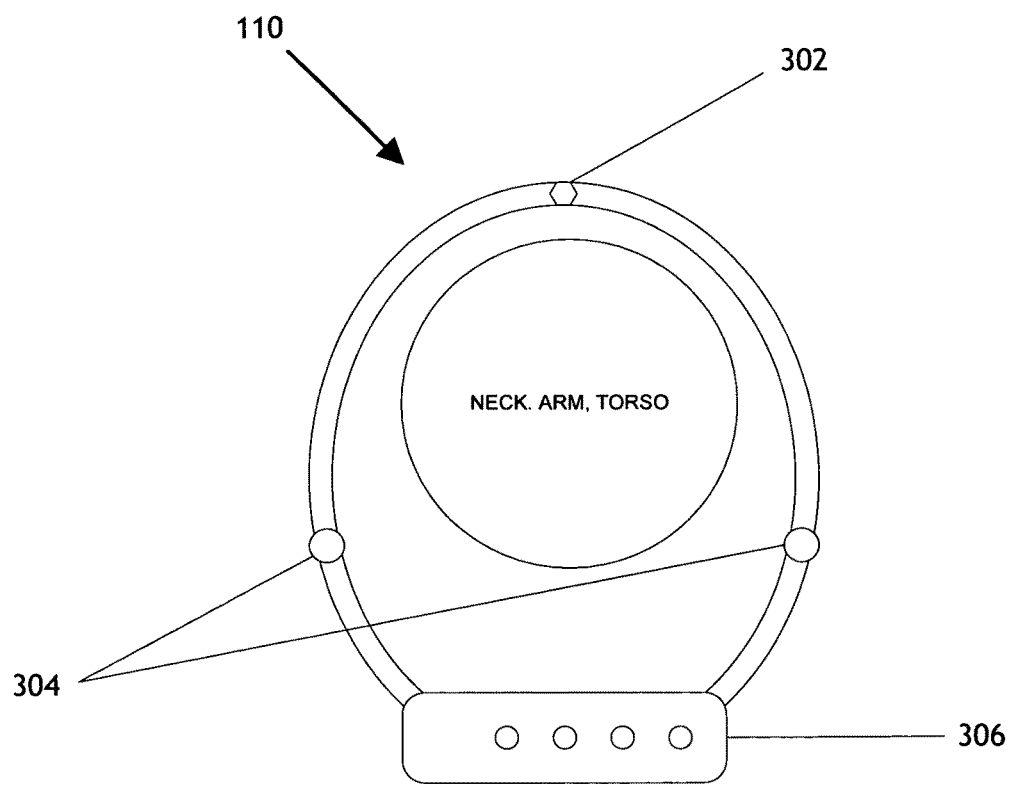
FIG. 3 illustrates an exemplary inhalation device.
Figure 4:
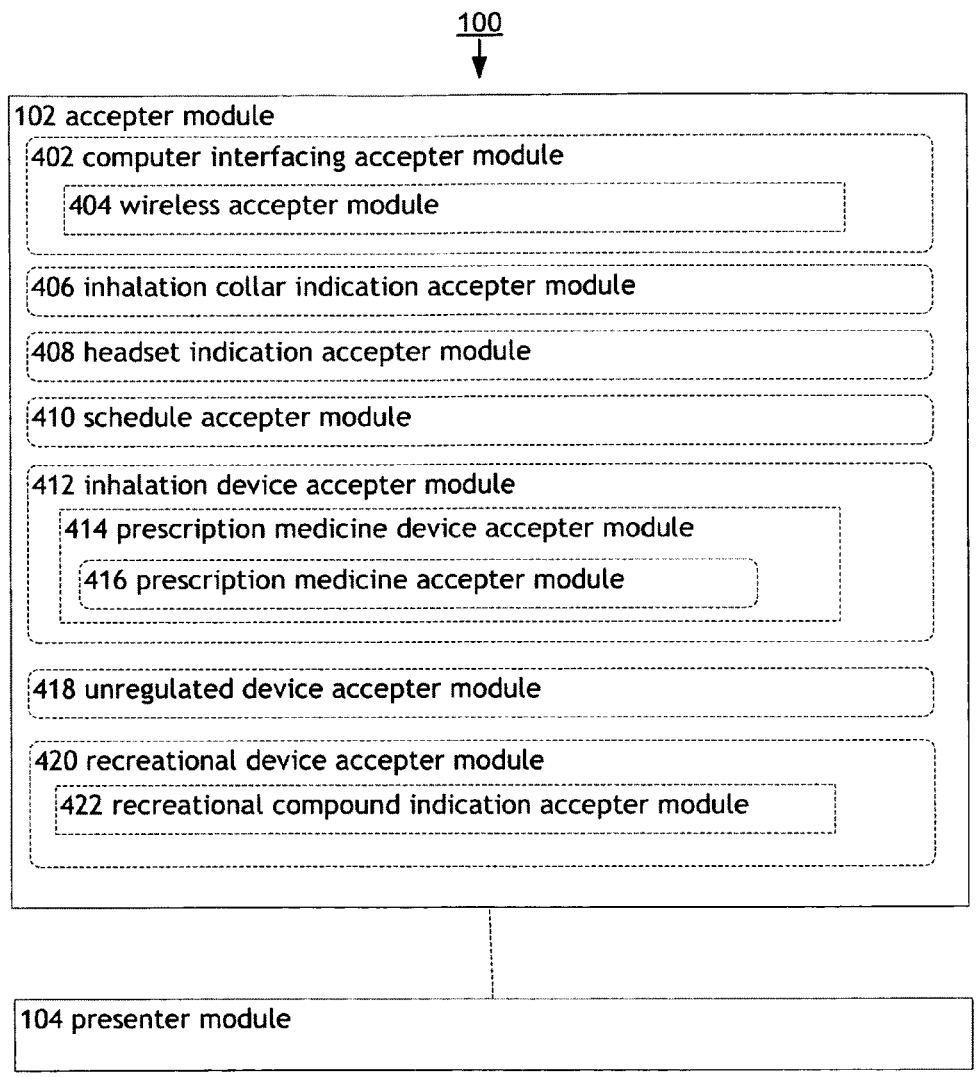
FIG. 4 illustrates an exemplary environment in which one or more technologies may be implemented.
Figure 5:
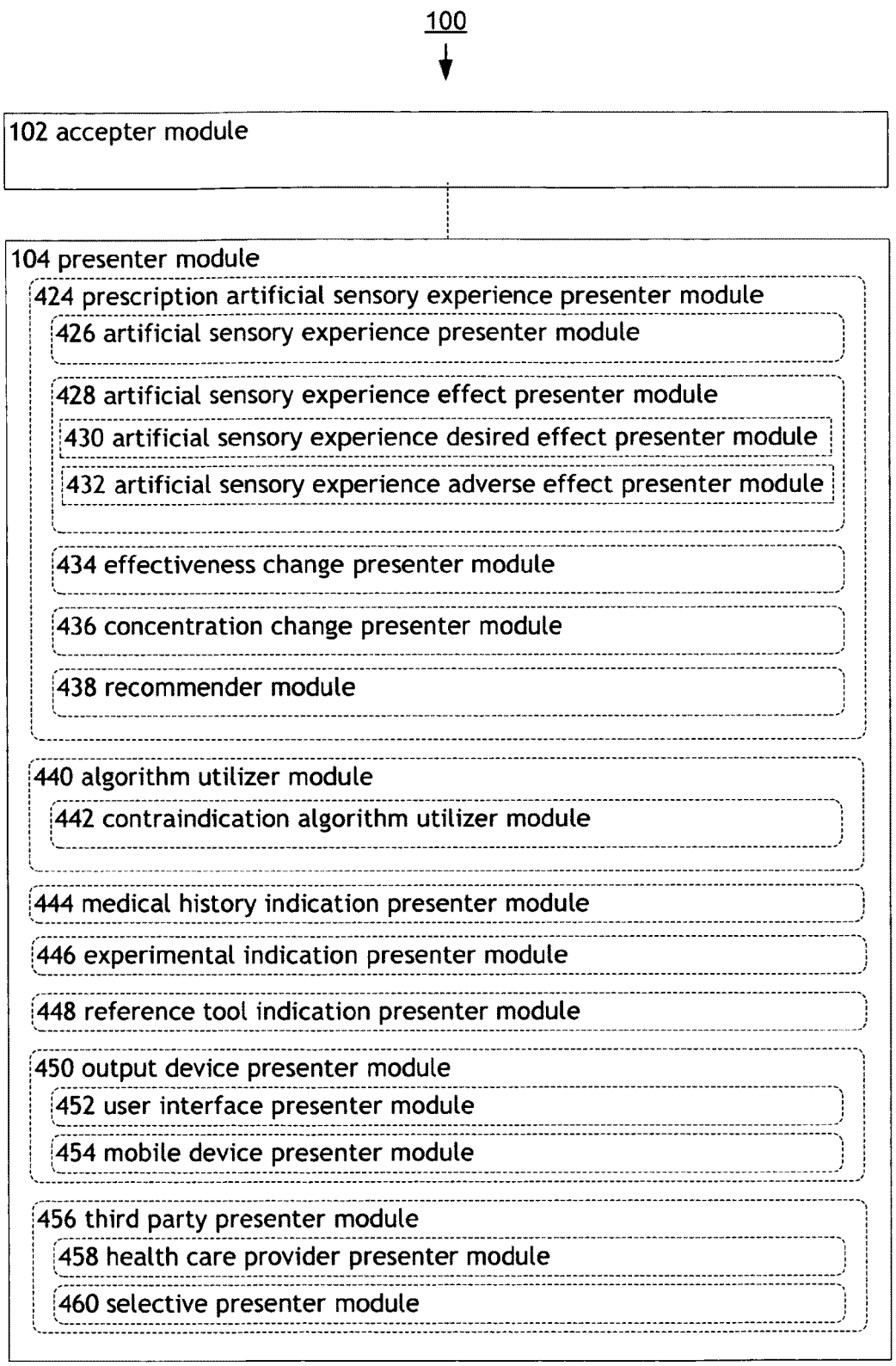
FIG. 5 illustrates an exemplary environment in which one or more technologies may be implemented.

Third party presenter module 456 may include health care provider presenter module 458 and/or selective presenter module 460.

FIG. 6 illustrates an operational flow 600 representing example operations related to accepting an indication of at least one health-related condition and presenting an indication of at least one artificial sensory experience and an indication of at least one inhalation therapy at least partially based on the accepting at least one indication of a health-related condition. In FIG. 6 and in following figures that include various examples of operational flows, discussion and explanation may be provided with respect to the above-described examples of FIGS. 1 through 5, and/or with respect to other examples and contexts. However, it should be understood that the operational flows may be executed in a number of other environments and contexts, and/or in modified versions of FIGS. 1 through 5. Also, although the various operational flows are presented in the sequence(s) illustrated, it should be understood that the various operations may be performed in other orders than those which are illustrated, or may be performed concurrently.

After a start operation, the operational flow 600 moves to operation 610. Operation 610 depicts accepting an indication of at least one health-related condition. For example, as shown in FIGS. 1 through 5, accepter module 102 may accept an indication of a bioactive agent-dispensing inhalation device. One example of a bioactive agent-dispensing inhalation device may include an inhaler used for delivering a bioactive agent into the body using a body airway. Some other examples may include a collar, necklace, and/or a bracelet with a bioactive agent dispenser proximate to the nose, mouth, and/or inhalation route. In one embodiment, accepter module 102 may accept an indication of a bioactive agent-dispensing collar for dispensing a medication, such as a steroid and/or a bronchodilator. In some instances, accepter module 102 may include a computer processor, a user interface, and/or computer memory.

Then, operation 620 depicts presenting an indication of at least one artificial sensory experience and an indication of at least one inhalation therapy at least partially based on the accepting at least one indication of a health-related condition. For example, as shown in FIGS. 1 through 5, presenter module 104 may present an indication of a virtual world at least partially based on accepting an indication of a bioactive agent-dispensing inhalation device. One example of an artificial sensory experience may include a virtual world and/or other computer-simulated experience. Other examples of an artificial sensory experience may include experiences triggering sight, smell, hearing, touch, and/or taste. For example, presenter module 104 may present an indication of an artificial sensory experience including a virtual scent environment, which may include olfactory stimulation for improving memory. In an additional embodiment, presenter module 104 may present an indication of an artificial sensory experience including a virtual experience where the user is exposed to a virtual mountain environment coupled with a bronchodilator dose from a bioactive agent-dispensing inhalation collar. In this embodiment, the combination bronchodilator and virtual world treatment may serve to help an asthma sufferer to learn effective breathing techniques. Presenting an indication of an artificial sensory experience may include presenting the indication to a physician, to a computer monitor, to a mobile device, and/or to a third party. In some instances, presenter module 104 may include a computer processor and/or a communication device, such as a printer, a computer monitor, and/or a speaker.

FIG. 7 illustrates alternative embodiments of the example operational flow 600 of FIG. 6. FIG. 7 illustrates example embodiments where operation 610 may include at least one additional operation. Additional operations may include operation 702, operation 704, operation 706, and/or operation 708.

Operation 702 illustrates accepting an indication of a health-related physical condition. For example, as shown in FIGS. 1 through 5, computer interfacing accepter module 402 may accept an indication of a bioactive agent-dispensing inhalation device configured to interface with a computing device. In one embodiment, computer interfacing accepter module 402 may accept an indication of a bioactive agent-dispensing inhalation device configured to interface with a virtual game, such as World of Warcraft. Some examples of a computing device may include a personal computer, a virtual-reality helmet and/or headset, and/or a virtual environment. In some instances, computer interfacing accepter module 402 may include a computer processor.

Further, operation 704 illustrates accepting an indication of a bioactive agent-dispensing inhalation device configured to interface wirelessly with a computing device. For example, as shown in FIGS. 1 through 5, wireless accepter module 404 may accept an indication of a bioactive agent-dispensing inhalation device configured to interface wirelessly with a computing device. In one embodiment, wireless accepter module 404 may accept an indication of a wireless inhalation collar configured to interface wirelessly with a computer coupled to wireless video glasses. In this embodiment, both the inhalation collar and the video glasses may be wirelessly connected to the computer. The wireless bioactive agent-dispensing inhalation device may be wirelessly coupled to a computing device using, for example, an IEEE 802.11 computer network and/or a Bluetooth wireless sensor network. One example of wireless video glasses may include Qingbar GP300 video glasses available from 22moo International Pty Ldt., Cabramatta NSW, Australia. In some instances, wireless accepter module 404 may include a computer processor and/or a wireless receiving device, such as a receiving antenna.

Operation 706 illustrates accepting an indication a health-related condition from a medical history. For example, as shown in FIGS. 1 through 5, inhalation collar indication accepter module 406 may accept an indication of a bioactive agent-dispensing inhalation collar. A bioactive agent-dispensing inhalation collar may include a collar with, for example, means for dispensing a bioactive agent, such as a reservoir and/or an accompanying valve and spray nozzle. Additionally, means for dispensing a bioactive agent may include means for dispensing an aerosol, vapor, a powder (e.g. pulmicort and/or foradil), and/or a mist, such as a nebulizer, means for measuring and/or detecting a condition, such as blood oxygen level and/or body temperature, and/or means for processing information, such as a computer processor and/or computer memory. Further, a bioactive agent may be dispensed and/or dispersed in and/or include a surfactant. In one embodiment, inhalation collar indication accepter module 406 may accept an indication of a bioactive agent-dispensing collar having means for dispensing a steroid as an aerosol. Further, a bioactive agent-dispensing inhalation collar may include means for power, such as a battery and/or circuitry for receiving power from an external source, such as an AC adapter power supply. In some instances, inhalation collar indication accepter module 406 may include a computer processor.

Operation 708 illustrates accepting an indication of a bioactive agent-dispensing virtual-reality headset. For example, as shown in FIGS. 1 through 5, headset indication accepter module 408 may accept an indication of a bioactive agent-dispensing virtual-reality headset. A virtual-reality headset may include a microphone, headphones or speakers for hearing, and/or a display. A virtual-reality headset may be configured for enabling a user to engage in an artificial sensory experience including sound, smell, and/or sight. One example of a virtual-reality headset may include a virtual reality helmet configured to give the user a 360° view of a mountain landscape while dispensing a bronchodilator for helping the user learn improved breathing techniques. Another example of a virtual reality head set may include an Olympus Eye-Trek FMD-200-TFT active matrix head mounted display with Speaker, available from Olympus America Inc., Center Valley Pa. In some instances, headset indication accepter module 408 may include a computer processor.

FIG. 8 illustrates alternative embodiments of the example operational flow 600 of FIG. 6. FIG. 8 illustrates example embodiments where the operation 610 may include at least one additional operation. Additional operations may include an operation 802, an operation 804, an operation 806, and/or an operation 808.

Operation 802 illustrates accepting an indication of a health-related mental condition. For example, as shown in FIGS. 1 through 5, schedule accepter module 410 may accept at least one of a bioactive agent dosing schedule or a bioactive agent administration schedule. Accepting a bioactive agent dosing schedule or a bioactive agent administration schedule may include accepting from a computer processor, accepting from a memory device, and/or accepting from a user input. In one embodiment, schedule accepter module 410 may accept a dosing schedule specifying a bronchodilator administration dosage for a specified time period, such one dose from an inhalation device once every thirty minutes. In another embodiment, schedule accepter module 410 may accept a bioactive agent administration schedule specifying at least one time a bronchodilator may be administered. In some instances, schedule accepter module 410 may include a computer processor.

Operation 804 illustrates accepting an indication of a medicine-dispensing inhalation device. For example, as shown in FIGS. 1 through 5, inhalation device accepter module 412 may accept an indication of a medicine-dispensing inhalation device. A medicine-dispensing inhalation device may include a device for dispensing a substance for treating a disease and/or illness. For example, a medicine-dispensing inhalation device may include an inhaler as described in Robertson et al., U.S. Pat. No. 7,383,837, which is incorporated herein by reference. Some other examples may include a metered-dose inhaler, a dry powder inhaler, and/or a nebulizer. In one embodiment, inhalation device accepter module 412 may accept an indication of a medicine-dispensing metered-dose inhaler configured to dispense albuterol. In some instances, inhalation device accepter module 412 may include a computer processor.

Further, operation 806 illustrates accepting an indication of a health-related condition from a user input. For example, as shown in FIGS. 1 through 5, prescription medicine device accepter module 414 may accept an indication of a prescription medicine-dispensing inhalation device. A prescription medicine-dispensing inhalation device may include a device configured to dispense a medication only available from a licensed health care provider. Some examples of a prescription medication available from a licensed health care provider may include albuterol, coricosteroids, nitrous oxide, a benzodiazepine, Theophylline, nedocromil sodium, and/or fluticasone/salmeterol. In one embodiment, prescription medicine device accepter module 414 may accept an indication of a prescription medicine-dispensing inhalation device configured for dispensing ciclesonide. In some instances, prescription medicine device accepter module 414 may include a computer processor.

Further, operation 808 illustrates indication of at least one of a prescribed artificial sensory experience or a prescribed inhalation therapy. For example, as shown in FIGS. 1 through 5, prescription medicine accepter module 416 may accept an indication of at least one of a steroid, a bronchodilator, menthol, nitrous oxide, a benzodiazepine, or halothane. One example of a steroid may include an anabolic steroid, which may be a derivative of androgens (such as testosterone), for stimulating growth. Another example of a steroid may include a corticosteroid, which may be often used as an anti-inflammatory prescribed for asthma. A bronchodilator may include a substance that dilates the bronchi and bronchioles decreasing airway resistance and thereby facilitating airflow. Menthol may include an organic and/or synthetic compound with local anesthetic and counterirritant qualities often used for relieving throat irritation and/or as a decongestant. Nitrous oxide may include a gas often used as a weak general anesthetic. A benzodiazepine may include a class of psychoactive drugs with varying hypnotic, sedative, anxiolytic, anticonvulsant, muscle relaxant and amnesic properties, which may be mediated by slowing down the central nervous system. In one embodiment, prescription medicine accepter module 416 may accept an indication of a benzodiazepine. One example of benzodiazepine delivery through an inhalation route may be disclosed in Kim et al., U.S. Patent Publication No. 2003/0032638, which is incorporated herein by reference. An anti-allergic agent may include an agent configured to block the action of allergic mediators and/or to prevent activation of cells and degranulation processes. Some examples of an anti-allergic agent may include an antihistamine and/or cromones like mast cell stabilizers, such as cromoglicic acid and nedocromil sodium. A muscle relaxant may include a bioactive agent for affecting skeletal muscle function and/or decreasing muscle tone. One example of a skeletal muscle relaxant may include carisoprodol. Additionally, a muscle relaxant may include a smooth muscle relaxant. One example of a smooth muscle relaxant may include a methylxanthine, such as Theophylline. An anesthetic may include an inhalational general anesthetic, such as halothane, desflurane, enflurane, isoflurane, and/or sevoflurane. In some instances, prescription medicine accepter module 416 may include a computer processor.

Figure 9:
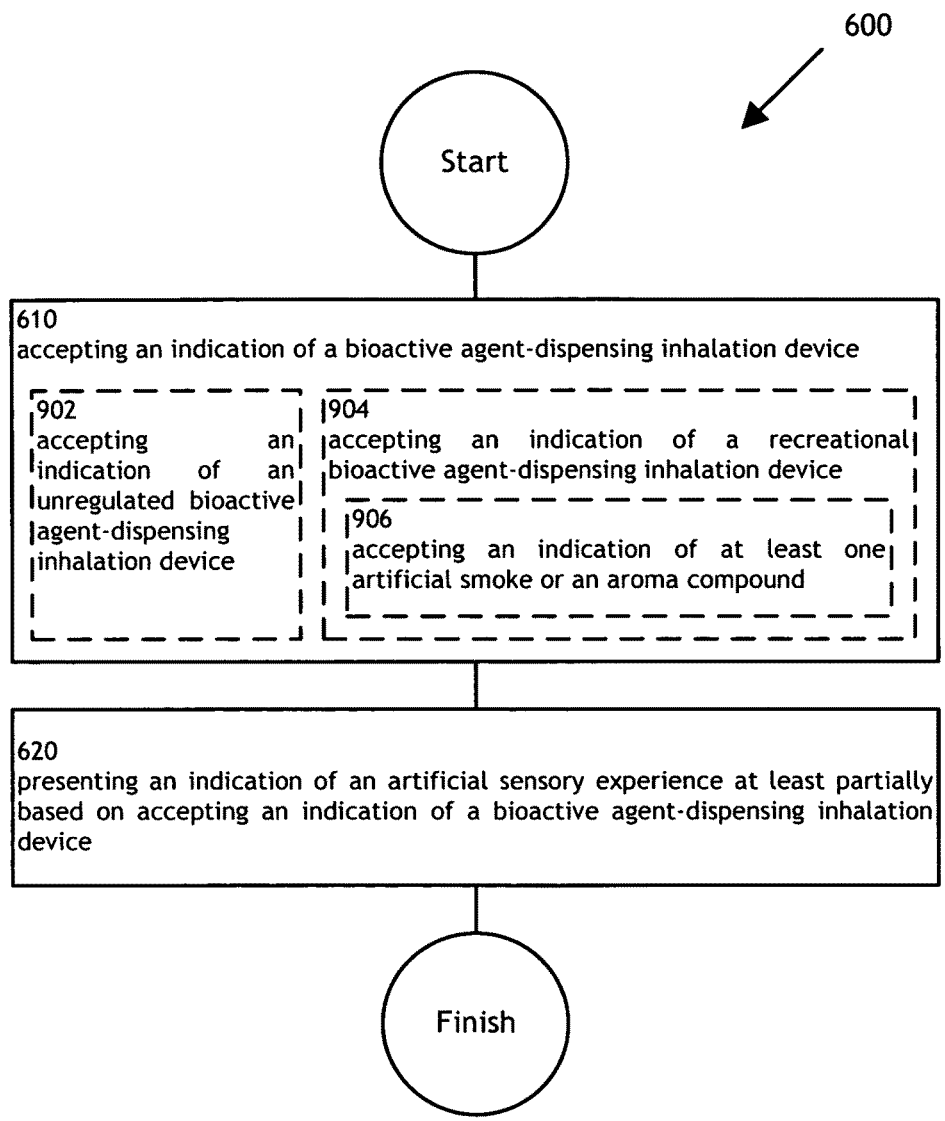
FIG. 9 illustrates an alternative embodiment of the operational flow of FIG. 6.

FIG. 9 illustrates alternative embodiments of the example operational flow 600 of FIG. 6. FIG. 9 illustrates example embodiments where the operation 610 may include at least one additional operation. Additional operations may include an operation 902, an operation 904, and/or an operation 906.

Operation 902 illustrates accepting an indication of an unregulated bioactive agent-dispensing inhalation device. For example, as shown in FIGS. 1 through 5, unregulated device accepter module 418 may accept an indication of an unregulated bioactive agent-dispensing inhalation device. In one embodiment, unregulated device accepter module 418 may accept an indication of an oxygen-dispensing inhalation device. Some examples of an unregulated bioactive agent may include oxygen, aromas used for aromatherapy, and/or menthol. In another embodiment, unregulated device accepter module 418 may accept an indication of an aromatherapeutic-dispensing inhalation collar. In some instances, unregulated device accepter module 418 may include a computer processor.

Operation 904 illustrates accepting an indication of a recreational bioactive agent-dispensing inhalation device. For example, as shown in FIGS. 1 through 5, recreational device accepter module 420 may accept an indication of a recreational bioactive agent-dispensing inhalation device. In one embodiment, recreational device accepter module 420 may accept an indication of a recreational bioactive agent-dispensing inhalation device. Some examples of a recreational bioactive agent may include an aroma compound used for aromatherapy and/or artificial smoke. Other examples of a recreational bioactive agent may include incense and/or smoke, such as incense and/or smoke used in a religious rite. In some instances, recreational device accepter module 420 may include a computer processor.

Further, operation 906 illustrates accepting an indication of at least one artificial smoke or an aroma compound. For example, as shown in FIGS. 1 through 5, recreational compound indication accepter module 422 may accept an indication of at least one artificial smoke or an aroma compound. In one embodiment, recreational compound indication accepter module 422 may accept an indication of artificial smoke while experiencing a virtual world. In another embodiment, recreational compound indication accepter module 422 may accept an indication of lemon oil while experiencing an artificial sensory experience. In this embodiment, the use of lemon oil as an aromatherapeutic may serve to enhance a user's mood and/or provide relaxation. In some instances, recreational compound indication accepter module 422 may include a computer processor.

FIG. 10 illustrates alternative embodiments of the example operational flow 600 of FIG. 6. FIG. 10 illustrates example embodiments where operation 620 may include at least one additional operation. Additional operations may include operation 1002, operation 1004, operation 1006, operation 1008, and/or operation 1010.

Operation 1002 illustrates indication of at least one of a prescribed artificial sensory experience or a prescribed inhalation therapy. For example, as shown in FIGS. 1 through 5, prescription artificial sensory experience presenter module 424 may present an indication of a prescribed artificial sensory experience. A prescribed artificial sensory experience may include any artificial sensory experience prescribed by a health care professional, such as a physician, a mental health specialist, a nurse, a physical therapist, an occupational therapist, a chiropractor, and/or a homeopathic practitioner. In one embodiment, prescription artificial sensory experience presenter module 424 may present an indication of a virtual world prescribed by a psychiatrist. In this embodiment, the prescribed virtual world may be configured to be administered in conjunction with a prescribed bioactive agent. Administering a prescribed bioactive agent in conjunction with a prescribed artificial sensory experience may serve to increase efficacy of the combined therapy, for example, by serving as a distraction from pain. In some instances, prescription artificial sensory experience presenter module 424 may include a computer processor and/or a display device, such as a computer monitor and/or a printer.

Further, operation 1004 illustrates an indication of at least one of a virtual world experience, a massively multiplayer online game, or a learning tutorial. For example, as shown in FIGS. 1 through 5, artificial sensory experience presenter module 426 may present an indication of a virtual world experience, a massively multiplayer online game, or a learning tutorial. A virtual world experience may include a computer-based simulated environment intended to be interactive. Some examples of a virtual world experience may include a text-based chat room, computer conferencing, an online game, a single player game, and/or a computer tutorial. A massively multiplayer online game may include a video game capable of supporting multiple players, such as World of Warcraft and/or SecondLife. Additionally, a massively multiplayer online game may include an experience, such as a game, which may include a video game or other interactive experience involving numbers of individuals, for example, a religious ceremony or combat training exercise. An online learning tutorial may include a screen recording, a written document (either online or downloadable), or an audio file, where a user may be given step by step instructions on how to do something. In one embodiment, artificial sensory experience presenter module 426 may present an indication of a virtual world experience, such as World of Warcraft. In some instances, artificial sensory experience presenter module 426 may include a computer processor.

Further, operation 1006 illustrates indication of at least one effect of the indication of at least one of a prescribed artificial sensory experience. For example, as shown in FIGS. 1 through 5, artificial sensory experience effect presenter module 428 may present an indication of at Least one effect of the prescribed artificial sensory experience. In one embodiment, artificial sensory experience effect presenter module 428 may present an indication of at least one effect of the prescribed artificial sensory experience. An effect may include a reaction and/or thing that occurs as a result of the artificial sensory experience. For example, an effect may include a side effect, a desired effect, and/or an adverse effect. Some examples of an effect may include an increased bioactive agent efficacy, dizziness, and/or a decreased heart rate. In some instances, artificial sensory experience effect presenter module 428 may include a computer processor.

Further, operation 1008 illustrates presenting an indication of at least one expected desired effect of the prescribed artificial sensory experience. For example, as shown in FIGS. 1 through 5, artificial sensory experience desired effect presenter module 430 may present an indication of at least one desired effect of the prescribed artificial sensory experience. Some examples of a desired effect may include effects such as an increased bioactive agent efficacy, a cured illness and/or condition, and/or a changed behavior. In one embodiment, artificial sensory experience desired effect presenter module 430 may present an indication of an increased opioid efficacy measured by self pain evaluation by an individual. In some instances, artificial sensory experience desired effect presenter module 430 may include a computer processor and/or a display, such as a monitor and/or a printer.

Further, operation 1010 illustrates an indication of at least one prescribed inhalation therapy. For example, as shown in FIGS. 1 through 5, artificial sensory experience adverse effect presenter module 432 may present an indication of an expected adverse effect of the prescribed artificial sensory experience. An adverse effect may include a harmful and/or undesired effect resulting from an intervention, such as an artificial sensory experience. Some examples of an adverse effect may include headache, dizziness, depression, bleeding, seizure, and/or fever. In one embodiment, artificial sensory experience adverse effect presenter module 432 may present an indication of fever in an individual while being administered a prescribed artificial sensory experience and bioactive agent. In some instances, artificial sensory experience adverse effect presenter module 432 may include a computer processor, a display device, such as a monitor and/or printer, and/or medical instrumentation, such as a thermometer configured for measuring a body temperature.

FIG. 11 illustrates alternative embodiments of the example operational flow 600 of FIG. 6. FIG. 11 illustrates example embodiments where operation 620 may include at least one additional operation. Additional operations may include operation 1102, operation 1104, and/or operation 1106.

Operation 1102 illustrates an indication of at least one prescribed bioactive agent. For example, as shown in FIGS. 1 through 5, effectiveness change presenter module 434 may present an indication of at least one time period of an expected change in bioactive agent effectiveness. In one embodiment, effectiveness change presenter module 434 may present an indication of a time period when an opioid is expected to decrease in effectiveness. Such an indication of decrease and/or change in bioactive agent effectiveness may serve to indicate an appropriate time period for administering and/or modifying an artificial sensory experience to compensate for a change in bioactive agent efficacy. In another embodiment, effectiveness change presenter module 434 may present an indication of a time period where a blood stream morphine concentration drops. This time period of low blood stream morphine concentration may be appropriate for presenting an immersive virtual world for serving as a distraction to any increase in pain caused by lowered morphine concentration. In some instances, effectiveness change presenter module 434 may include a computer processor.

Further, operation 1104 illustrates an indication of at least one time period of an expected change in bioactive agent blood concentration. For example, as shown in FIGS. 1 through 5, concentration change presenter module 436 may present an indication of at least one time period of an expected change in bioactive agent blood concentration. In one embodiment, concentration change presenter module 436 may present an indication of a one hour time period of an expected change in hydrocodone blood concentration. Indicating a time period of a change in blood concentration may serve to help determine an artificial sensory experience administration schedule. For example, if a bioactive agent blood concentration is expected to be reduced during a certain time period, an artificial sensory experience configured for distracting an individual from pain may be selected for administration during that time period. In some instances, concentration change presenter module 436 may include a computer processor and/or a display device, such as a printer and/or a computer monitor.

Further, operation 1106 illustrates recommending at least one of an artificial sensory experience administration schedule. For example, as shown in FIGS. 1 through 5, recommender module 438 may recommend an artificial sensory experience administration schedule. In one embodiment, recommender module 438 may recommend a time schedule for administration of a virtual world experience. A time schedule may be recommended by taking into account factors involving the individual and/or the bioactive agent. For example, efficacy of the bioactive agent versus time may be a factor, such as a time period when the bioactive agent is less effective. Efficacy of the bioactive agent may be a factor in determining when an artificial sensory experience is administered because of the potential for the artificial sensory experience to compensate for a changed bioactive agent efficacy. An additional factor may include an attribute of the individual, such as how a bioactive agent and/or specific artificial sensory experience affects the individual, for example a side effect. Another example of recommending an artificial sensory experience may be found in Akazawa et al., U.S. Pat. No. 7,155,680, which is incorporated herein by reference. In some instances, recommender module 438 may include a computer processor.

Figure 12:
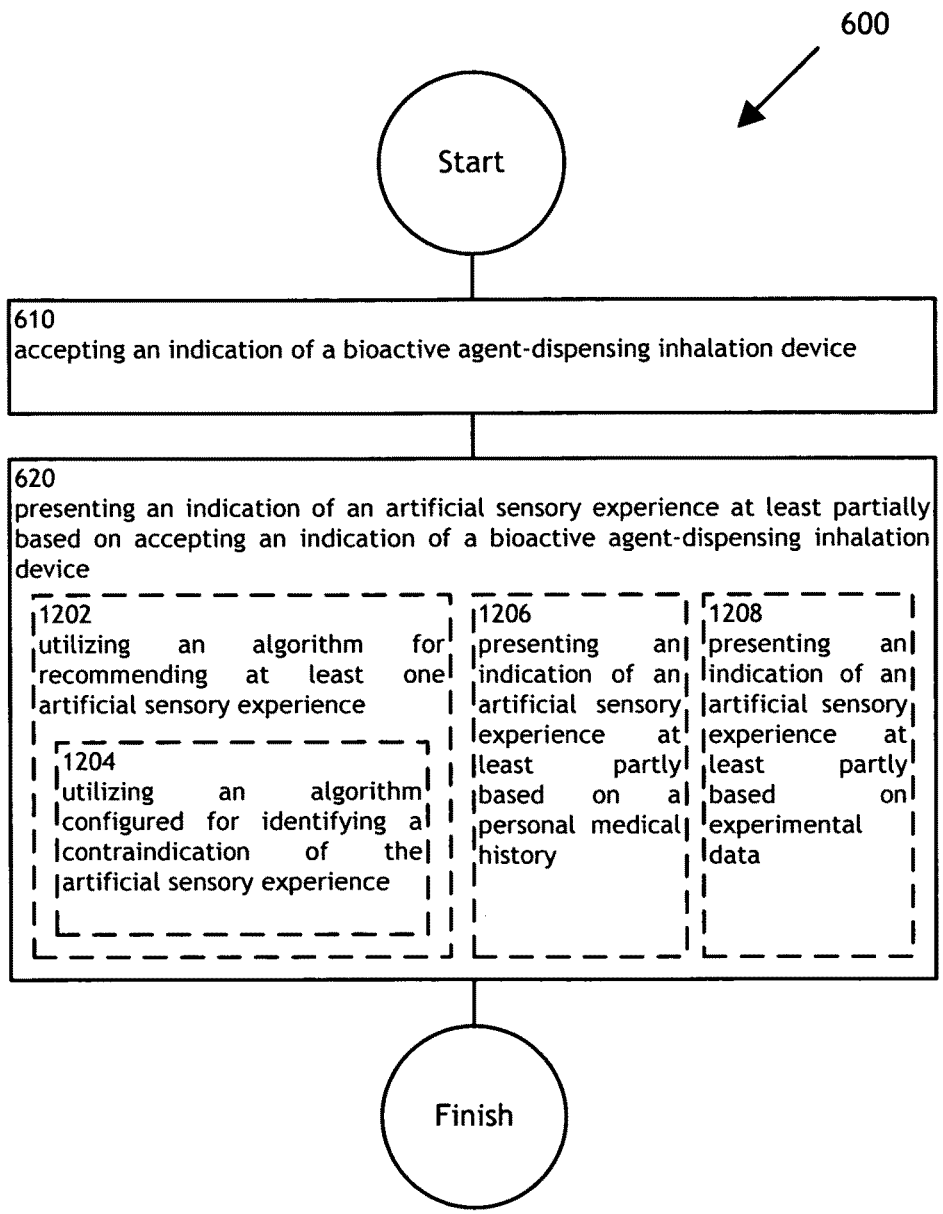
FIG. 12 illustrates an alternative embodiment of the operational flow of FIG. 6.

FIG. 12 illustrates alternative embodiments of the example operational flow 600 of FIG. 6. FIG. 12 illustrates example embodiments where operation 620 may include at least one additional operation. Additional operations may include operation 1202, operation 1204, operation 1206, and/or operation 1208.

Operation 1202 illustrates an indication of an unregulated inhalation. For example, as shown in FIGS. 1 through 5, algorithm utilizer module 440 may utilize an algorithm for recommending at least one artificial sensory experience. An algorithm for recommending an artificial sensory experience may include any computation, formula, statistical survey, and/or look-up table for determining and/or selecting a suitable artificial sensory experience. Some examples may include a computer software algorithm, a calculator, a flowchart, and/or a decision tree. In one embodiment, algorithm utilizer module 440 may utilize an algorithm that uses an inputted indication of an analgesic, such as oxycodone, and determines a suitable artificial sensory experience by analyzing periods of low blood concentration of the oxycodone. In this embodiment, algorithm utilizer module 440 may recommend an artificial sensory experience that may be effective in pain distraction when bioactive agent blood concentration may be reduced but before an additional dose may be available. In some instances, algorithm utilizer module 440 may include a computer processor.

Further, operation 1204 illustrates an indication of an unregulated inhalation. For example, as shown in FIGS. 1 through 5, contraindication algorithm utilizer module 442 may utilize an algorithm configured for identifying a contraindication of the artificial sensory experience. A contraindication of an artificial sensory experience may include giving an indication against the advisability of the artificial sensory experience. For example, contraindication algorithm utilizer module 442 may utilize an algorithm that considers an individual's personal medical history, such as a phobia, and may recommend not prescribing a certain artificial sensory experience, which may include an object that may trigger the phobia. Contraindication algorithm utilizer module 442 may identify a contraindication of an artificial sensory experience for reasons such as an adverse effect and/or inefficacy. In some instances, contraindication algorithm utilizer module 442 may include a computer processor.

Operation 1206 illustrates presenting an indication of an artificial sensory experience at least partly based on a personal medical history. For example, as shown in FIGS. 1 through 5, medical history indication presenter module 444 may present an indication of an artificial sensory experience at least partly based on a personal medical history. A medical history may include a personal history and/or a family history. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In one embodiment, medical history indication presenter module 444 may present an indication of a suitable virtual world based on a personal medical history. In this embodiment, the personal medical history may indicate that an individual may be averse to a certain virtual world, such as a virtual world with rapid animation that may cause nausea. In some instances, medical history indication presenter module 444 may include a computer processor and/or a display device, such as a computer monitor and/or a printer.

Operation 1208 illustrates utilizing an algorithm configured for recommending at least one of an artificial sensory experience. For example, as shown in FIGS. 1 through 5, experimental data indication presenter module 446 may present an indication of an artificial sensory experience at least partly based on experimental data. Experimental data may include any data from an experiment, such as a clinical trial. The experiment may be an experiment including an individual and/or a group of people. In one embodiment, experimental data indication presenter module 446 may present an indication of a virtual world suitable for an individual based on a clinical trial involving a group of 1,000 people showing a certain success rate for reducing a phobia, such as fear of heights. In some instances, experimental data indication presenter module 446 may include a computer processor and/or a display device, such as a computer monitor, a mobile phone, and/or a printer.

Figure 13:
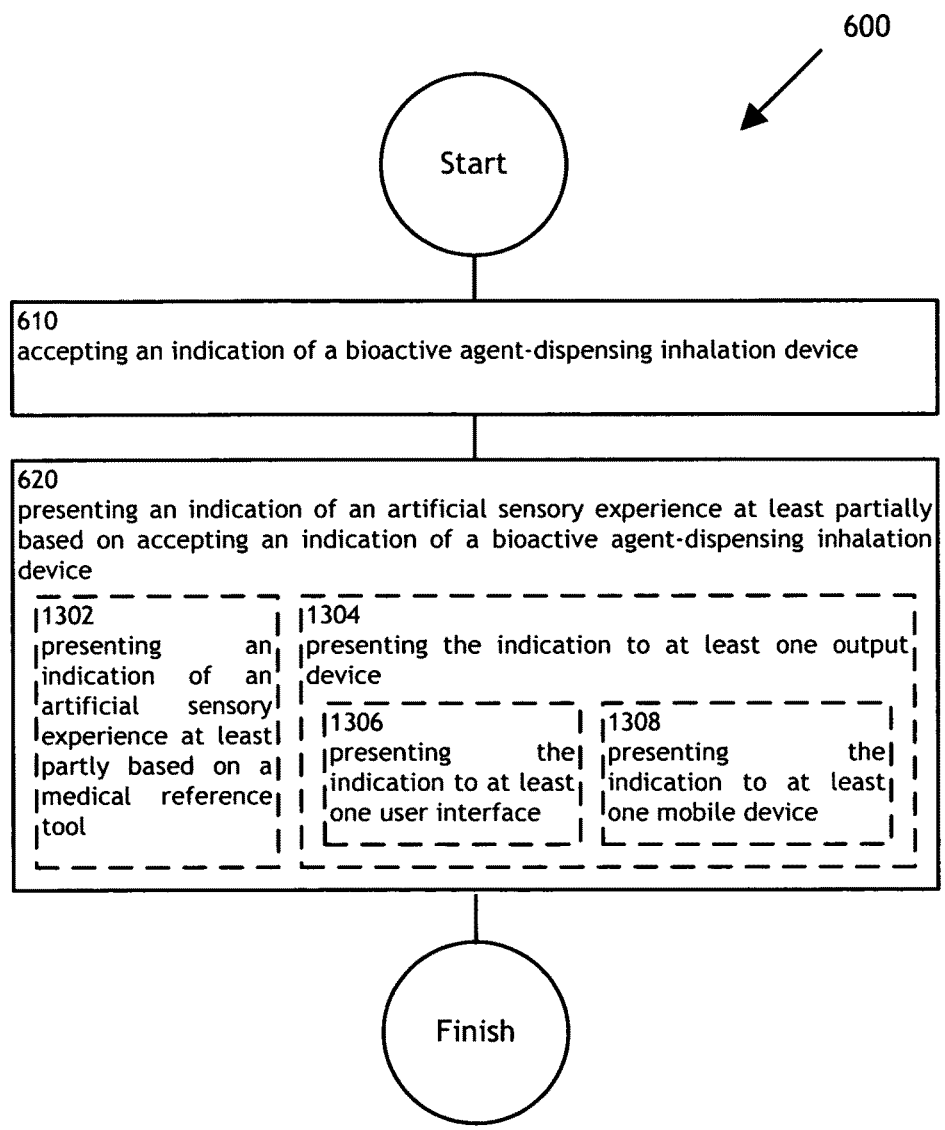
FIG. 13 illustrates an alternative embodiment of the operational flow of FIG. 6.

FIG. 13 illustrates alternative embodiments of the example operational flow 600 of FIG. 6. FIG. 13 illustrates example embodiments where the operation 620 may include at least one additional operation. Additional operations may include an operation 1302, an operation 1304, an operation 1306, and/or an operation 1308.

Operation 1302 illustrates presenting at least one of an indication of an artificial sensory experience or an indication of inhalation therapy at least partly based on a medical reference tool. For example, as shown in FIGS. 1 through 5, reference tool indication presenter module 448 may present an indication of an artificial sensory experience at least partly based on a medical reference tool. A medical reference tool may include a reference book, a reference database, and/or reference software. Some examples of a medical reference book may include a medical dictionary, a medical journal, and/or a book of drug interactions. One example of a reference database may include the National Cancer Center Cancer Image Reference (NCC-CIR) database and/or DynaMed. Some examples of reference software may include Skyscape software for a mobile phone and/or MedAlert. In one embodiment, reference tool indication presenter module 448 may present an indication of an artificial sensory experience based on a reference database, such as a database including data from a clinical trial. In some instances, reference tool indication presenter module 448 may include a computer processor and/or a display device, such as a mobile phone, a printer, and/or a computer monitor.

Operation 1304 illustrates presenting the indication to at least one output device. For example, as shown in FIGS. 1 through 5, output device presenter module 450 may present to at Least one output device. In one example, output device presenter module 450 may present an indication of a combination prescription medication and an artificial sensory experience therapy to an output device 130, such as a printer and/or monitor at a health clinic. An output device may include any hardware device configured for receiving computer output. Some examples of an output device may include a printer, a monitor, a mobile phone, a speaker, and/or a visual display unit. The output device 130 may be used by individual 134. In some instances, output device presenter module 450 may include a computer processor.

Further, operation 1306 illustrates presenting the indication to at least one user interface. For example, as shown in FIGS. 1 through 5, user interface presenter module 452 may present to at least one user interface. In one embodiment, user interface presenter module 452 may present to a touchscreen device. A user interface may include means by which an individual may interact with a system. Some examples of a user interface may include a touchscreen, a graphical user interface, a tactile interface, and/or a live user interface. In some instances, user interface presenter module 452 may include a computer processor.

Further, operation 1308 illustrates presenting the indication to at least one mobile device. For example, as shown in FIGS. 1 through 5, mobile device presenter module 454 may present to at least one mobile device. In one embodiment, mobile device presenter module 454 may present to a mobile phone. A mobile device may include a portable computing device and may have wireless connection capability. Some examples of a mobile device may include a laptop or notebook computer, a personal digital assistant (PDA), an ipod, a smartphone, an Enterprise digital assistant (EDA), and/or a pager. In some instances, mobile device presenter module 454 may include a computer processor.

FIG. 14 illustrates alternative embodiments of the example operational flow 600 of FIG. 6. FIG. 14 illustrates example embodiments where operation 620 may include at least one additional operation. Additional operations may include operation 1402, operation 1404, and/or operation 1406.

Operation 1402 illustrates presenting the indication to at least one third party. For example, as shown in FIGS. 1 through 5, third party presenter module 456 may present to an individual's physician. A third party may include a party that is an independent party, person, and/or entity. Some examples of a third party may include a physician, a medical database, a hospital, a law enforcement agency, and/or a pharmacy. In one embodiment, third party presenter module 456 may present an indication to an insurance company. Another example of reporting to a third party may include creating displays and reports for aggregating data from therapy results, further discussed in Bair et al., U.S. Pat. No. 6,067,523, which is incorporated herein by reference. In some instances, third party presenter module 456 may include a computer processor and/or a communications device, such as a monitor and network link.

Further, operation 1404 illustrates presenting the indication to at least one health care provider. For example, as shown in FIGS. 1 through 5, health care provider presenter module 458 may present to a health care provider. A health care provider may include a pharmacy, a pharmaceutical company, a medical device company, a research institution, a computer software and/or computer hardware company, a website, a nurse and/or a physician. In one embodiment, health care provider presenter module 458 may present to a physician a prescribed combination artificial sensory experience and bioactive agent therapy via a secured website. In some instances, health care provider presenter module 458 may include a computer processor.

Further, operation 1406 illustrates selectively presenting the indication only to the individual. For example, as shown in FIGS. 1 through 5, selective presenter module 460 may selectively present only to the individual. Selective presenting may include limiting and/or blocking access of an individual's compliance results and/or a prescribed therapy, such as a prescribed artificial sensory experience and/or bioactive agent to a specific party. For example, selective presenter module 460 may present only to individual 134 and may keep results of a certain combination therapy confidential. In one embodiment, an encryption key may be employed to protect selected information. In an additional example, selective presenter module 460 may report only to a law enforcement agency and/or representative, such as a probation officer, and not to individual 134. In some instances, selective presenter module 460 may include a computer processor.

FIG. 15 illustrates alternative embodiments of the example operational flow 600 of FIG. 6. FIG. 15 illustrates example embodiments where the operation 620 may include at least one additional operation. Additional operations may include an operation 1502.

Operation 1502 illustrates accepting an indication of an individual's asthma, presenting a prescribed administration schedule of an albuterol-dispensing collar therapy for the individual, and presenting a prescription for engagement of the individual with a virtual world experience configured to teach the individual a deep breathing technique. For example, as shown in FIGS. 1 through 5, accepter module 102 and/or presenter module 104 may accept an indication of an albuterol-dispensing collar configured to be worn proximate to the neck of an individual, accept a prescribed administration schedule of the albuterol-dispensing collar for the individual, and present a prescription for engagement of the individual with a virtual world experience configured to teach the individual a deep breathing technique. In some instances, accepter module 102 and/or presenter module 104 may include a computer processor.

Figure 16:
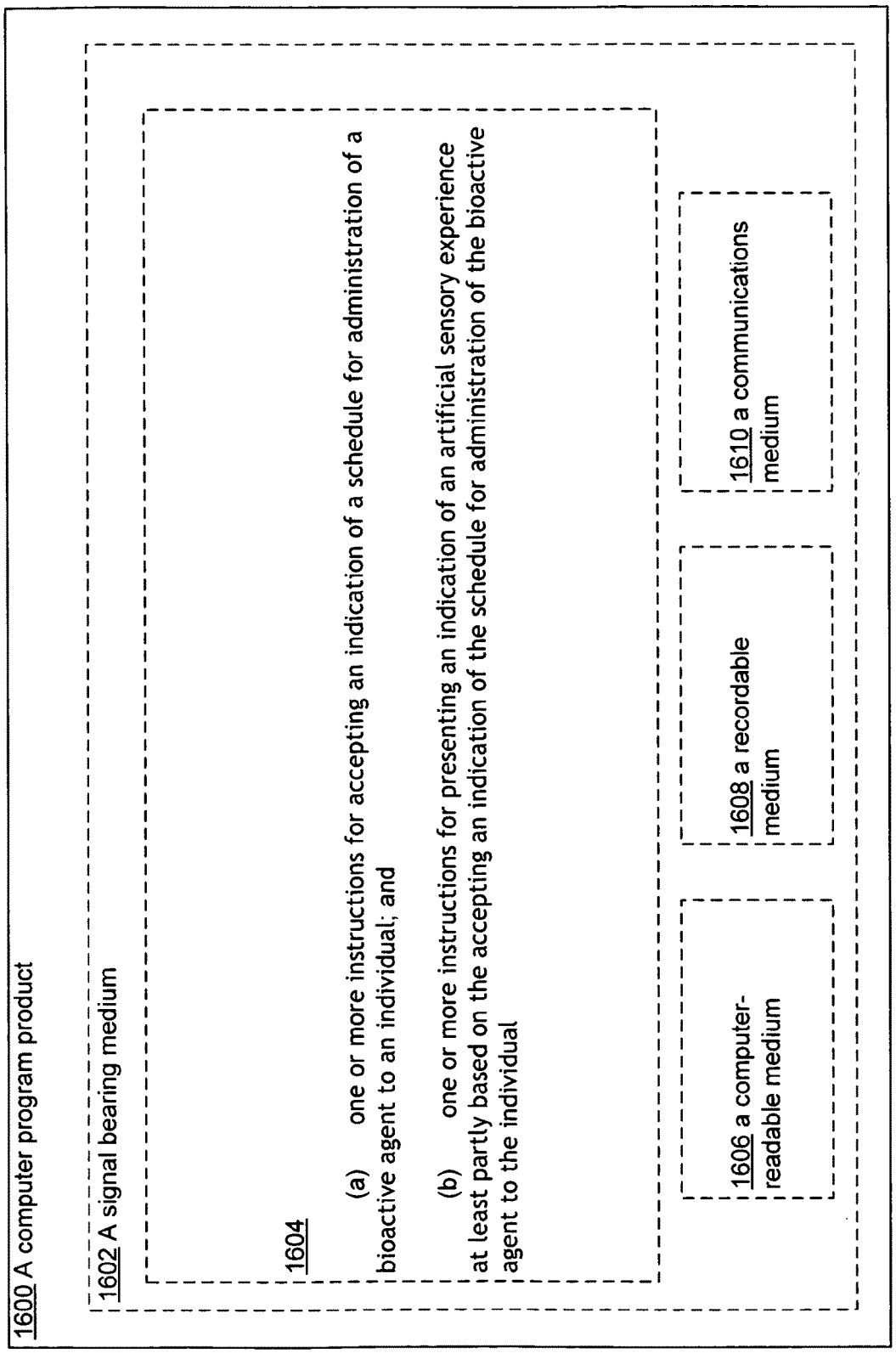
FIG. 16 illustrates a computer program product related to combining an inhaled bioactive agent and an artificial sensory experience.

FIG. 16 illustrates a partial view of an example computer program product 1600 that includes a computer program 1604 for executing a computer process on a computing device. An embodiment of the example computer program product 1600 is provided using a signal-bearing medium bearing 1602, and may include one or more instructions for accepting an indication of at least one health-related condition and one or more instructions for presenting an indication of at least one artificial sensory experience and an indication of at least one inhalation therapy at least partially based on the accepting at least one indication of a health-related condition. The one or more instructions may be, for example, computer executable and/or logic-implemented instructions. In one implementation, the signal-bearing medium 1602 may include a computer-readable medium 1606. In one implementation, the signal bearing medium 1602 may include a recordable medium 1608. In one implementation, the signal bearing medium 1602 may include a communications medium 1610.

Figure 17:
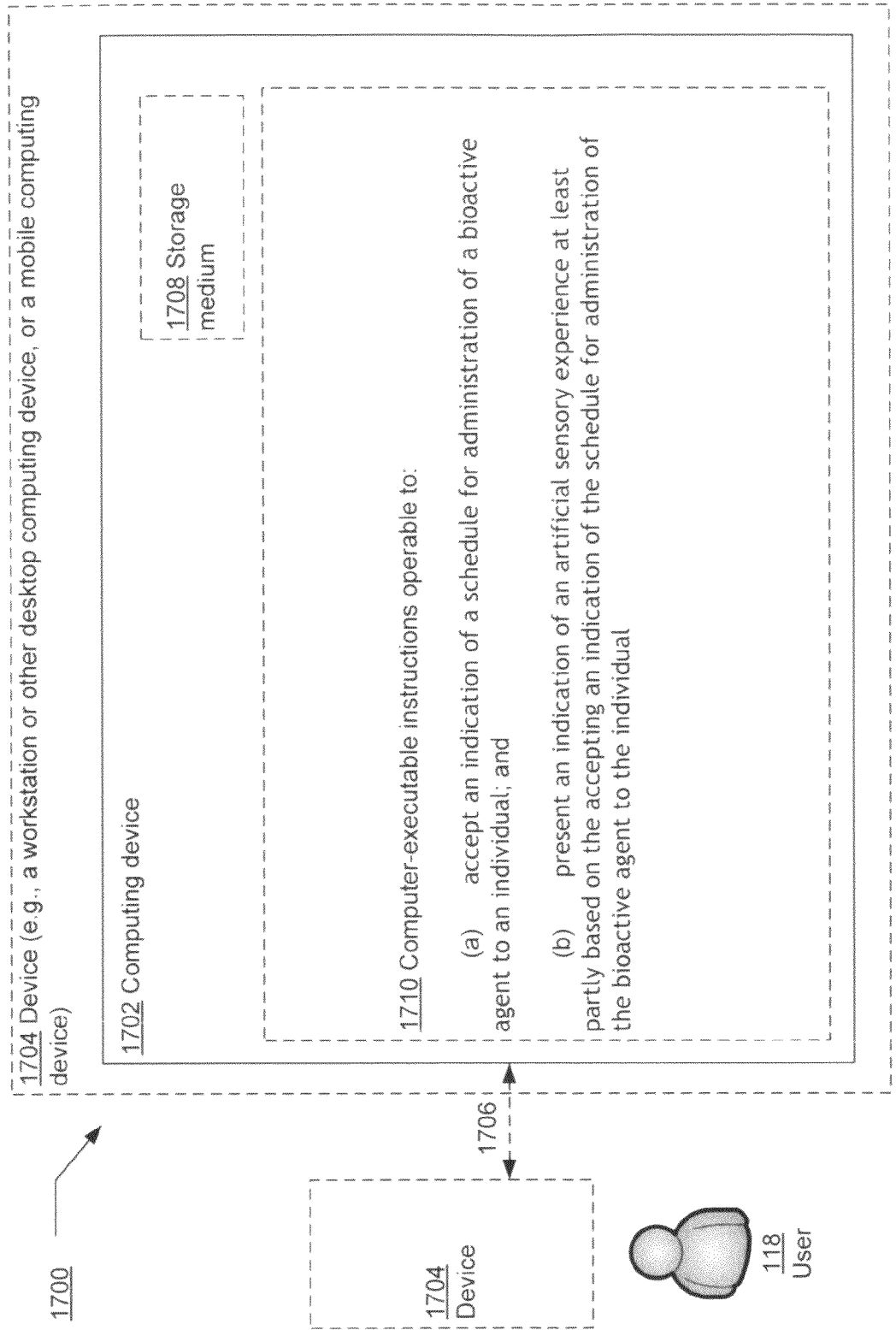
FIG. 17 illustrates a system related to combining an inhaled bioactive agent and an artificial sensory experience.

FIG. 17 illustrates an example system 1700 in which embodiments may be implemented. The system 1700 includes a computing system environment. The system 1700 also illustrates the user 118 using a device 1704, which is optionally shown as being in communication with a computing device 1702 by way of an optional coupling 1706. The optional coupling 1706 may represent a local, wide-area, or peer-to-peer network, or may represent a bus that is internal to a computing device (e.g., in example embodiments in which the computing device 1702 is contained in whole or in part within the device 1704). A storage medium 1708 may be any computer storage media.

The computing device 1702 includes computer-executable instructions 1710 that when executed on the computing device 1702 cause the computing device 1702 to accept an indication of a schedule for administration of a bioactive agent to an individual and present an indication of an artificial sensory experience at least partly based on the accepting an indication of the schedule for administration of the bioactive agent to the individual. As referenced above and as shown in FIG. 17, in some examples, the computing device 1702 may optionally be contained in whole or in part within the device 1704.

In FIG. 17, then, the system 1700 includes at least one computing device (e.g., 1702 and/or 1704). The computer-executable instructions 1710 may be executed on one or more of the at least one computing device. For example, the computing device 1702 may implement the computer-executable instructions 1710 and output a result to (and/or receive data from) the computing device 1704. Since the computing device 1702 may be wholly or partially contained within the computing device 1704, the device 1704 also may be said to execute some or all of the computer-executable instructions 1710, in order to be caused to perform or implement, for example, various ones of the techniques described herein, or other techniques.

The device 1704 may include, for example, a portable computing device, workstation, or desktop computing device. In another example embodiment, the computing device 1702 is operable to communicate with the device 1704 associated with the user 118 to receive information about the input from the user 118 for performing data access and data processing and presenting an output of the user-health test function at least partly based on the user data.

Figure 18:
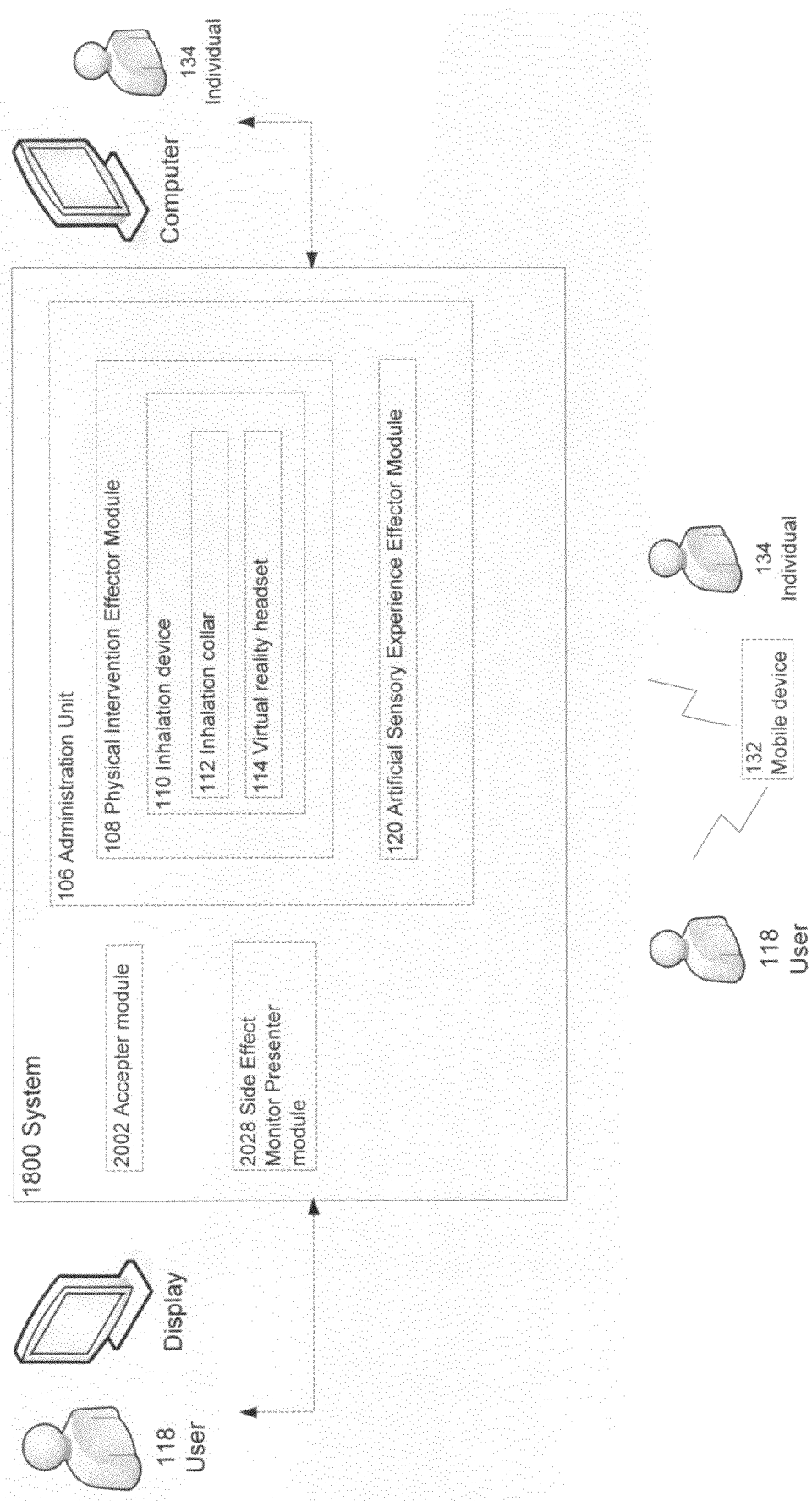
FIG. 18 illustrates an exemplary environment in which one or more technologies may be implemented.

FIG. 18 illustrates system 1800 for accepting at least one indication of use of an inhalation device configured to dispense a bioactive agent to an individual and/or presenting at least one artificial sensory experience to monitor at least one side effect of the bioactive agent on the individual. System 1800 may include accepter module 2002, side effect monitor presenter module 2028, and/or administration unit 106. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, system 1800 may include mobile device 132.

Figure 19:
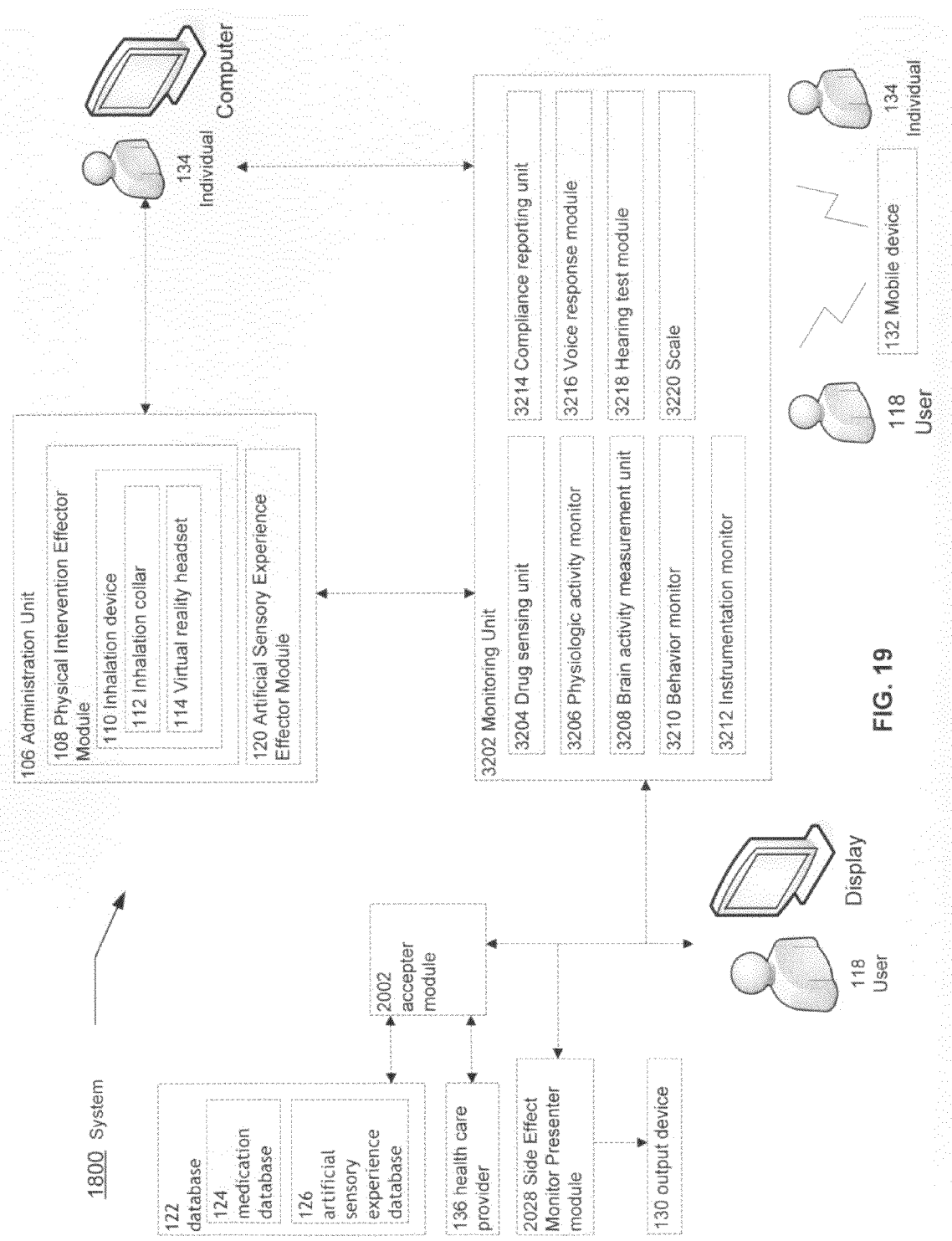
FIG. 19 illustrates an exemplary environment in which one or more technologies may be implemented.

FIG. 19 illustrates system 1800 for accepting at least one indication of use of an inhalation device configured to dispense a bioactive agent to an individual and/or presenting at least one artificial sensory experience to monitor at least one side effect of the bioactive agent on the individual. System 1800 may include accepter module 2002, side effect monitor presenter module 2028, administration unit 106, and/or monitoring unit 3202. Accepter module 2002 may receive and/or transmit information and/or data to and/or from user 118, database 122, side effect monitor presenter module 2028, output device 130, and/or health care provider 136. A user may include user 118, individual 134, health care provider 136, a patient, and/or another affected person or entity. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 106 may include physical intervention effector module 108 and/or artificial sensory experience effector module 120. Physical intervention effector module 108 may include inhalation device 110. Inhalation device 110 may include inhalation collar 112 and/or virtual reality headset 114. Additionally, mobile device 132 may communicate with accepter module 2002, presenter module 2028, healthcare provider 136, user 118, individual 134, monitoring unit 3202, and/or administration unit 106.

Figure 20:
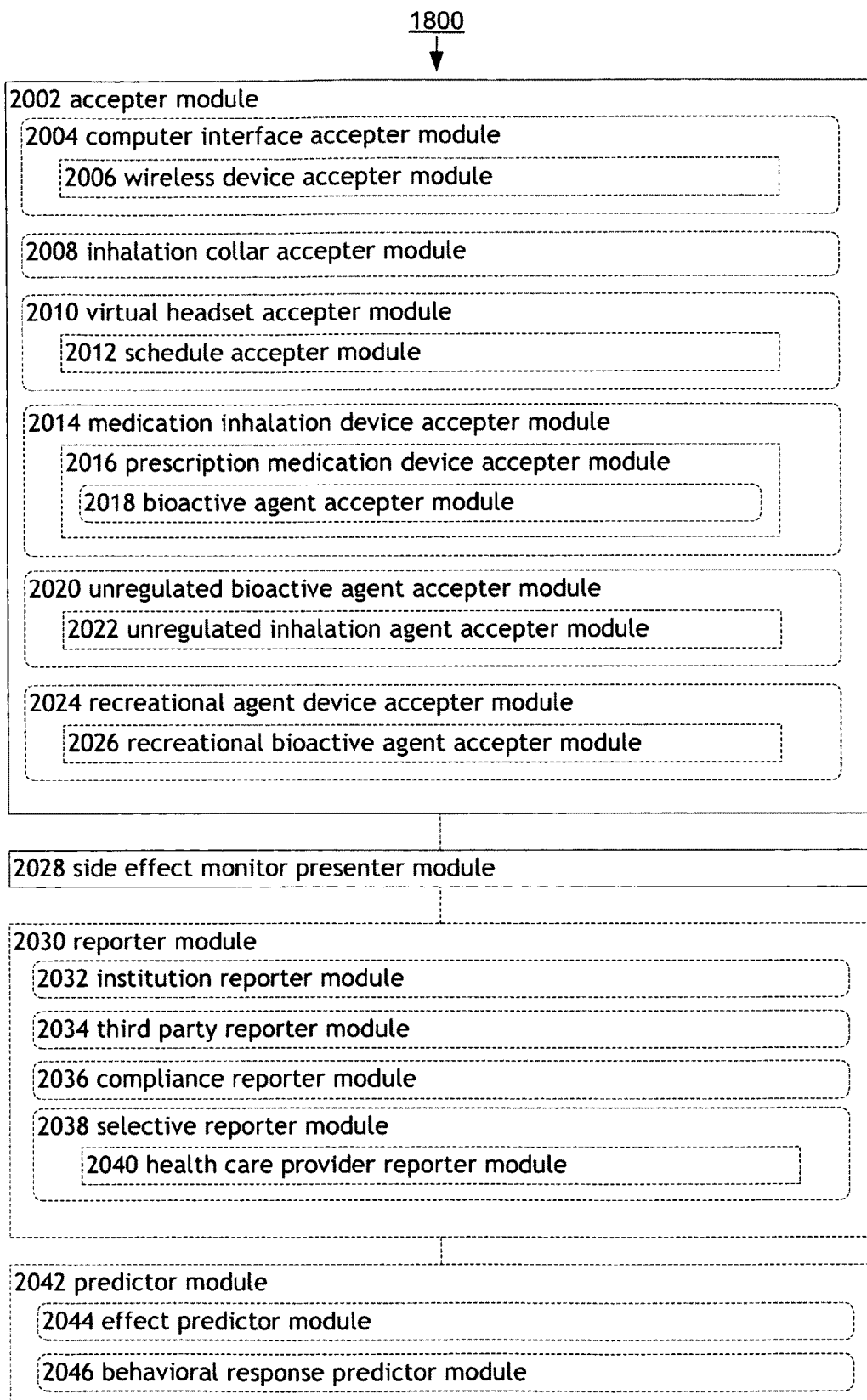
FIG. 20 illustrates an exemplary environment in which one or more technologies may be implemented.

FIG. 20 further illustrates system 1800 including accepter module 2002, side effect monitor presenter module 2028, reporter module 2030, and/or predictor module 2042. Accepter module 2002 may include computer interface accepter module 2004, inhalation collar accepter module 2008, virtual headset accepter module 2010, medication inhalation device accepter module 2014, unregulated bioactive agent accepter module 2020, and/or recreational agent device accepter module 2024. Computer interface accepter module 2004 may include wireless device accepter module 2006. Virtual headset accepter module 2010 may include schedule accepter module 2012. Medication inhalation device accepter module 2014 may include prescription medication device accepter module 2016. Prescription medication device accepter module 2016 may include bioactive agent accepter module 2018. Unregulated bioactive agent accepter module 2020 may include unregulated inhalation agent accepter module 2022. Recreational agent device accepter module 2024 may include recreational bioactive agent accepter module 2026. Reporter module 2030 may include institution reporter module 2032, third party reporter module 2034, compliance reporter module 2036, and/or selective reporter module 2038. Selective reporter module 2038 may include health care provider reporter module 2040. Predictor module 2042 may include effect predictor module 2044 and/or behavioral response predictor module 2046.

Figure 21:
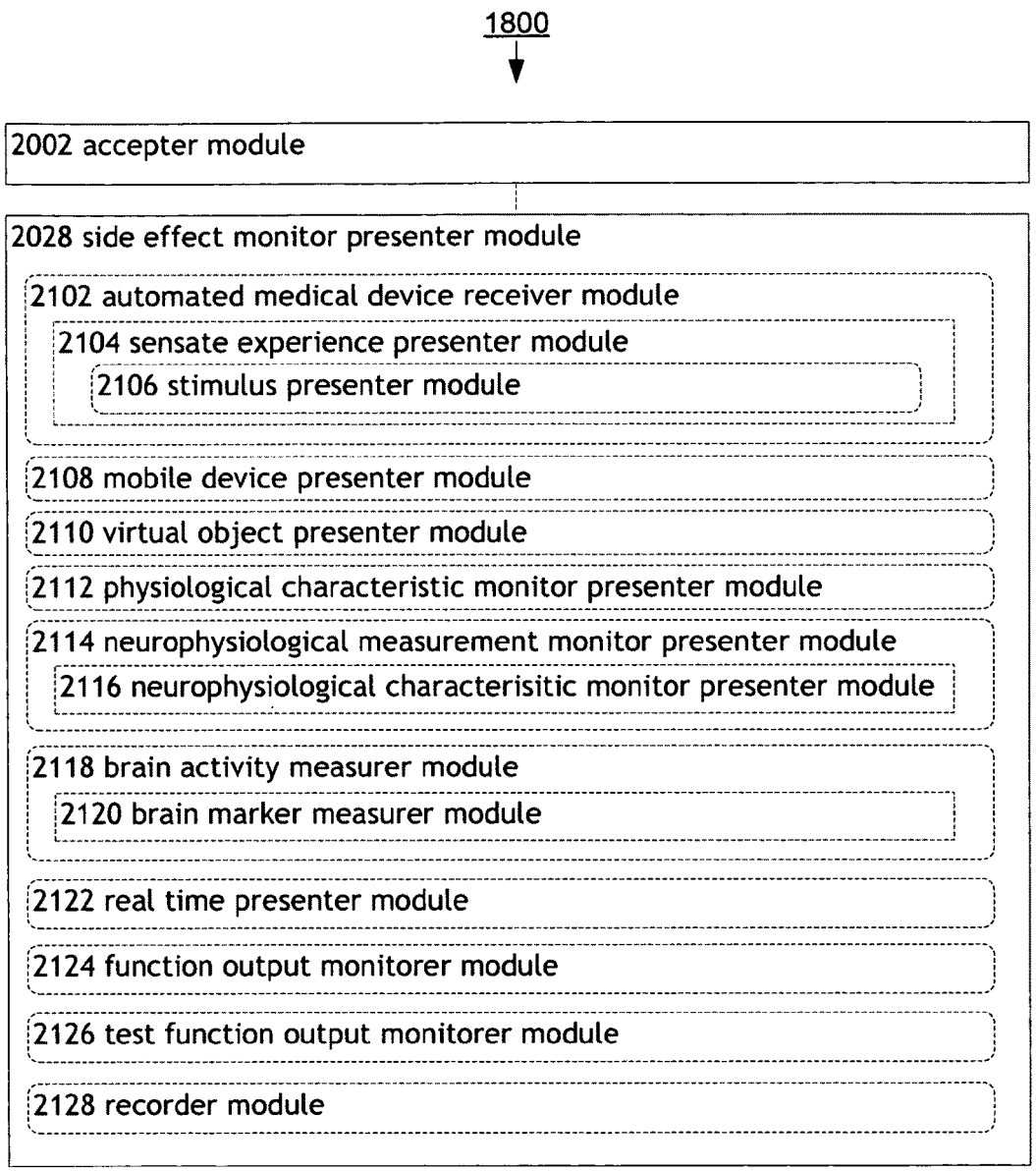
FIG. 21 illustrates an exemplary environment in which one or more technologies may be implemented.

FIG. 21 further illustrates system 1800 including accepter module 2002 and/or side effect monitor presenter module 2028. Side effect monitor presenter module 2028 may include automated medical device receiver module 2102, mobile device presenter module 2108, virtual object presenter module 2110, physiological characteristic monitor presenter module 2112, neurophysiological measurement monitor presenter module 2114, brain activity measurer module 2118, real time presenter module 2122, function output monitorer module 2124, test function output monitorer module 2126, and/or recorder module 2128. Automated medical device receiver module 2102 may include sensate experience presenter module 2104. Sensate experience presenter module 2104 may include stimulus presenter module 2106. Neurophysiological measurement monitor presenter module 2114 may include neurophysiological characteristic monitor presenter module 2116. Brain activity measurer module 2118 may include brain marker measurer module 2120.

FIG. 22 illustrates an operational flow 2200 representing example operations related to accepting at least one indication of use of an inhalation device configured to dispense a bioactive agent to an individual and presenting at least one artificial sensory experience to monitor at least one side effect of the bioactive agent on the individual. In FIG. 22 and in following figures that include various examples of operational flows, discussion and explanation may be provided with respect to the above-described examples of FIGS. 18 through 21, and/or with respect to other examples and contexts. However, it should be understood that the operational flows may be executed in a number of other environments and contexts, and/or in modified versions of FIGS. 18 through 21. Also, although the various operational flows are presented in the sequence(s) illustrated, it should be understood that the various operations may be performed in other orders than those which are illustrated, or may be performed concurrently.

After a start operation, the operational flow 2200 moves to an operation 2210. Operation 2210 depicts accepting at least one indication of use of an inhalation device configured to dispense a bioactive agent to an individual. For example, as shown in FIGS. 18 through 21, accepter module 2002 may accept an indication of use of an inhalation device configured to dispense a bioactive agent to an individual. One example of an inhalation device configured to dispense a bioactive agent may include an inhaler used for delivering a bioactive agent into the body using a body airway. Some other examples may include a collar, necklace, and/or a bracelet with a bioactive agent dispenser proximate to the nose, mouth, and/or inhalation route. In one embodiment, accepter module 2002 may accept an indication of a bioactive agent-dispensing collar for dispensing a medication, such as a steroid and/or a bronchodilator. In some instances, accepter module 2002 may include a computer processor, a user interface, and/or computer memory.

Then, operation 2220 depicts presenting at least one artificial sensory experience to monitor at least one side effect of the bioactive agent on the individual. For example, as shown in FIGS. 18 through 21, side effect monitor presenter module 2028 may present an artificial sensory experience to monitor at least one desired effect of the bioactive agent on the individual. Presenting an artificial sensory experience may include designating and/or specifying an artificial sensory experience tailored to the need of an individual 134, such as a patient in a doctor's care. Some examples of an artificial sensory experience may include a virtual experience, such as an online game or a social networking site, and/or a real-world sensory stimulus, such as a smell, a sound, and/or a sight. A side effect may include a harmful and/or undesired effect resulting from a medication or other intervention. Some side effect examples may include addiction, fever, headache, insomnia, drowsiness, nausea, irritability, and/or muscle aches. In one example, side effect monitor presenter module 2028 may present a virtual world or a modification to a virtual world, such as a modification to an online game such as World of Warcraft, to monitor a side effect of a specific medication administered, such as a steroid medication. In the same example, the medication side effect may be monitored based on a pattern of activity, such as aggression by the player in the virtual world and/or individual 134 in eliminating trolls and/or advancement by the player's avatar. Presenting may include, for example, searching a database 122 and matching a bioactive agent with an appropriate artificial sensory experience while taking into account characteristics of the individual 134, such as age, gender, susceptibility to adverse effects, and/or medication or therapeutic history. The presenting operation may entail merely the selection of a monitoring function to be carried out locally at the location of, for example, individual 134. In one embodiment, the selection of a monitoring function may be presented and/or reported to a third party and/or to the individual 134. In other embodiments, the presenting operation may entail implementation of a monitoring function directly, either remotely or locally. For each artificial sensory experience, in addition to therapeutic functions, monitoring functions may be implemented, for example, as a modification to a virtual experience computer program and/or through a separate monitoring function. In some embodiments, one or more stimuli in an artificial sensory experience may elicit one or more reactions in an individual that may relate to a side effect of a bioactive agent. For example, assignment of a Wii fitness virtual experience to provide physical therapy may serve to monitor the effectiveness of a coincident pain medication in the individual by measuring frequency of use, duration of use, range of motion, facial expression, or the like, which may be presented to another party and/or entity. Such monitoring capabilities may be added as a software module to the Wii itself, or the monitoring may be carried out by a different device. In some instances, side effect monitor presenter module 2028 may include a computer processor.

FIG. 23 illustrates alternative embodiments of the example operational flow 2200 of FIG. 22. FIG. 23 illustrates example embodiments where the operation 2210 may include at least one additional operation. Additional operations may include operation 2302, and/or operation 2304.

Operation 2302 illustrates accepting an indication of a bioactive agent-dispensing inhalation device configured to interface with a computing device. For example, as shown in FIGS. 18 through 21, computer interface accepter module 2004 may accept an indication of a bioactive agent-dispensing inhalation device configured to interface with a computing device. In one embodiment, computer interface accepter module 2004 may accept an indication of a bioactive agent-dispensing inhalation device configured to interface with a virtual game, such as World of Warcraft. Some examples of a computing device may include a personal computer, a virtual-reality helmet and/or headset, and/or a virtual environment. In some instances, computer interface accepter module 2004 may include a computer processor.

Further, operation 2304 illustrates accepting an indication of a bioactive agent-dispensing inhalation device configured to interface wirelessly with a computing device. For example, as shown in FIGS. 18 through 21, wireless device accepter module 2006 may accept an indication of a bioactive agent-dispensing inhalation device configured to interface wirelessly with a computing device. In one embodiment, wireless device accepter module 2006 may accept an indication of a wireless inhalation collar configured to interface wirelessly with a computer coupled to wireless video glasses. In this embodiment, both the inhalation collar and the video glasses may be wirelessly connected to the computer. The wireless bioactive agent-dispensing inhalation device may be wirelessly coupled to a computing device using, for example, an IEEE 802.11 computer network and/or a Bluetooth wireless sensor network. One example of wireless video glasses may include Qingbar GP300 video glasses available from 22moo International Pty Ldt., Cabramatta NSW, Australia. In some instances, wireless device accepter module 2006 may include a computer processor and/or a wireless receiving device, such as a receiving antenna.

FIG. 24 illustrates alternative embodiments of the example operational flow 2200 of FIG. 22. FIG. 24 illustrates example embodiments where the operation 2210 may include at least one additional operation. Additional operations may include operation 2402, operation 2404, and/or operation 2406.

Operation 2402 illustrates accepting an indication of a bioactive agent-dispensing inhalation collar. For example, as shown in FIGS. 18 through 21, inhalation collar accepter module 2008 may accept an indication of a bioactive agent-dispensing inhalation collar. A bioactive agent-dispensing inhalation collar may include a collar with, for example, means for dispensing a bioactive agent, such as a reservoir and/or an accompanying valve and spray nozzle. Additionally, means for dispensing a bioactive agent may include means for dispensing an aerosol, vapor, a powder (e.g., pulmicort and/or foradil), and/or a mist, such as a nebulizer, means for measuring and/or detecting a condition, such as blood oxygen level and/or body temperature, and/or means for processing information, such as a computer processor and/or computer memory. Further, a bioactive agent may be dispensed and/or dispersed in and/or include a surfactant. In one embodiment, inhalation collar accepter module 2008 may accept an indication of a bioactive agent-dispensing collar having means for dispensing a steroid as an aerosol. Further, a bioactive agent-dispensing inhalation collar may include means for power, such as a battery and/or circuitry for receiving power from an external source, such as an AC adapter power supply. Additionally, a bioactive agent-dispensing inhalation collar may receive power remotely, for example from a RF signal and/or via wireless power. Additional examples of receiving power remotely may be found in Clark et al., U.S. Patent Publication No. 2006/0058694, and Harland, C. J., et al., *Remote Detection of Human Electroencephalograms Using Ultrahigh Input Impedance Electrical Potential Sensors*, APPL. PHYS. LETT., 81(17) 3284-86, both of which are incorporated herein by reference. In some instances, inhalation collar accepter module 2008 may include a computer processor.

Operation 2404 illustrates accepting an indication of a bioactive agent-dispensing virtual-reality headset. For example, as shown in FIGS. 18 through 21, virtual headset accepter module 2010 may accept an indication of a bioactive agent-dispensing virtual-reality headset. A virtual-reality headset may include a microphone, headphones or speakers for hearing, and/or a display. A virtual-reality headset may be configured for enabling a user to engage in an artificial sensory experience including sound, smell, and/or sight. One example of a virtual-reality headset may include a virtual reality helmet configured to give the user a 360° view of a mountain landscape while dispensing a bronchodilator for helping the user learn improved breathing techniques. Another example of a virtual reality head set may include an Olympus Eye-Trek FMD-200-TFT active matrix head mounted display with Speaker, available from Olympus America Inc., Center Valley Pa. In one embodiment, headset accepter module 2010 may accept an indication of a bronchodilator dispensed by the above Olympus headset fitted with a bioactive agent reservoir and dispensing means. In some instances, virtual headset accepter module 2010 may include a computer processor.

Further, operation 2406 illustrates accepting at least one of a bioactive agent dosing schedule or a bioactive agent administration schedule. For example, as shown in FIGS. 18 through 21, schedule accepter module 2012 may accept at least one of a bioactive agent dosing schedule or a bioactive agent administration schedule. Accepting a bioactive agent dosing schedule or a bioactive agent administration schedule may include accepting from a computer processor, accepting from a memory device, and/or accepting from a user input. In one embodiment, schedule accepter module 2012 may accept a dosing schedule specifying a bronchodilator administration dosage for a specified time period, such one dose from an inhalation device once every thirty minutes. In another embodiment, schedule accepter module 2012 may accept a bioactive agent administration schedule specifying at least one time a bronchodilator may be administered. In some instances, schedule accepter module 2012 may include a computer processor.

Figure 25:
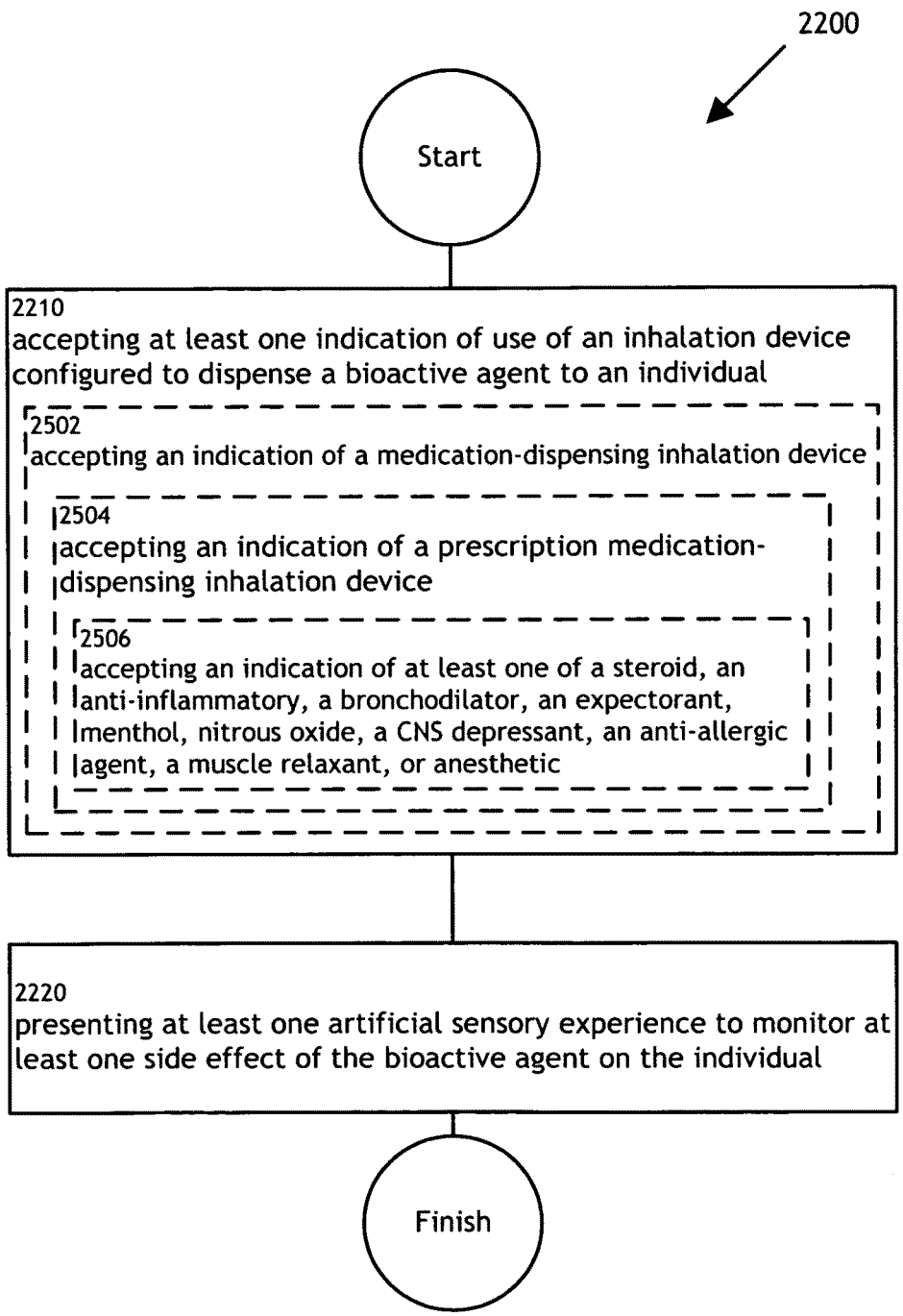
FIG. 25 illustrates an alternative embodiment of the operational flow of FIG. 22.

FIG. 25 illustrates alternative embodiments of the example operational flow 2200 of FIG. 22. FIG. 25 illustrates example embodiments where the operation 2210 may include at least one additional operation. Additional operations may include operation 2502, operation 2504, and/or operation 2506.

Operation 2502 illustrates accepting an indication of a medication-dispensing inhalation device. For example, as shown in FIGS. 18 through 21, medication inhalation device accepter module 2014 may accept an indication of a medication-dispensing inhalation device. In one embodiment, medication inhalation device accepter module 2014 may accept an indication of a medication-dispensing inhalation necklace adapted with a gas sensor where the indication includes the concentration of a by-product given off by an ingested bioactive agent. Additionally, indication of a medication-dispensing inhalation device may include a breath and/or gas analysis, for example, by a detection device coupled to the medication-dispensing inhalation device, such as tubing delivering a gas (e.g., breath) sample to a gas chromatograph from the medication-dispensing inhalation device. A medication-dispensing inhalation device may include a device, such as a collar, a necklace, and or a bracelet configured to dispense medicine, for example, with a bioactive agent reservoir and/or dispensing nozzles. In some instances, medication inhalation device accepter module 2014 may include a computer processor and/or means for detecting, such as a chemical sensor and/or a detector (e.g., for example an electric nose).

Further, operation 2504 illustrates accepting an indication of a prescription medication-dispensing inhalation device. For example, as shown in FIGS. 18 through 21, prescription medication device accepter module 2016 may accept an indication of a prescription medication-dispensing inhalation device. A prescription medication-dispensing inhalation device may include a device configured to dispense a medication only available from a licensed health care provider. One example of a prescription medication-dispensing inhalation device may include a collar and/or a bracelet with a reservoir for containing a bioactive agent and dispensing means, such as a nebulizer and/or nozzles. Some examples of a prescription medication available from a licensed health care provider may include a bronchodilator (including beta-agonists and anti-cholinergics) such as albuterol, coricosteroids, nitrous oxide, a sedative, such as benzodiazepine, Theophylline, nedocromil sodium, and/or fluticasone and salmeterol, and/or combinations thereof. In one embodiment, prescription medication device accepter module 2016 may accept an indication of a prescription medication-dispensing inhalation device configured for dispensing ciclesonide. The indication of the prescription medication-dispensing inhalation device may include, for example, an electrical and/or wireless signal from the device to a computer, computer software program, and/or computer monitor. In some instances, prescription medication device accepter module 2016 may include a computer processor.

Further, operation 2506 illustrates accepting an indication of at least one of a steroid, an anti-inflammatory, a bronchodilator, an expectorant, menthol, nitrous oxide, a CNS depressant, an anti-allergic agent, a muscle relaxant, or anesthetic. For example, as shown in FIGS. 18 through 21, bioactive agent accepter module 2018 may accept an indication of at least one of a steroid, an anti-inflammatory, a bronchodilator, an expectorant, menthol, nitrous oxide, a CNS-depressant, an anti-allergenic agent, a muscle relaxant, or an anesthetic. One example of a steroid may include an anabolic steroid, which may be a derivative of androgens (such as testosterone), for stimulating growth. Another example of a steroid may include a corticosteroid, which may be often used as an anti-inflammatory prescribed for asthma. An anti-inflammatory may include a bioactive agent utilized to treat and/or reduce inflammation. Some examples of an anti-inflammatory may include glucocorticoids, ibuprofen, and/or naproxen. A bronchodilator may include a substance that dilates the bronchi and bronchioles decreasing airway resistance and thereby facilitating airflow. A bronchodilator may include a beta-agonist, an anti-cholinergic, and/or a muscle relaxant, such as theophylline. An expectorant may include a bioactive agent used for dissolving and/or bringing up mucus from the lungs, respiratory tract, and/or trachea. Some examples of an expectorant may include guaifenesin and/or tyloxapol. Menthol may include an organic and/or synthetic compound with local anesthetic and counterirritant qualities often used for relieving throat irritation and/or as a decongestant. Nitrous oxide may include a gas often used as a weak general anesthetic. A CNS-depressant, such as benzodiazepine and/or a sedative, may include one class of psychoactive drugs with varying hypnotic, sedative, anxiolytic, anticonvulsant, muscle relaxant and amnesic properties, which may be mediated by slowing down the central nervous system. In one embodiment, bioactive agent accepter module 2018 may accept an indication of a benzodiazepine. One example of benzodiazepine delivery through an inhalation route may be disclosed in Kim et al., U.S. Patent Publication No. 2003/0032638, which is incorporated herein by reference. An anti-allergic agent may include an agent configured to block the action of allergic mediators and/or to prevent activation of cells and degranulation processes. Some examples of an anti-allergic agent may include an antihistamine and/or cromones like mast cell stabilizers, such as cromoglicic acid and nedocromil sodium. A muscle relaxant may include a bioactive agent for affecting skeletal muscle function, decreasing muscle tone, and/or affecting smooth muscle function. One example of a muscle relaxant may include a methylxanthine, such as Theophylline. An anesthetic may include an inhalational general anesthetic, such as halothane, desflurane, enflurane, isoflurane, and/or sevoflurane. Detecting an indication of a bioactive agent may include discovering the presence of the bioactive agent, such as through a chemical testing means (e.g., a breathalyzer, a litmus test, and/or a drug test). In some instances, bioactive agent accepter module 2018 may include a computer processor, an input device, such as a touchscreen user interface, and/or a mobile device.

Figure 26:
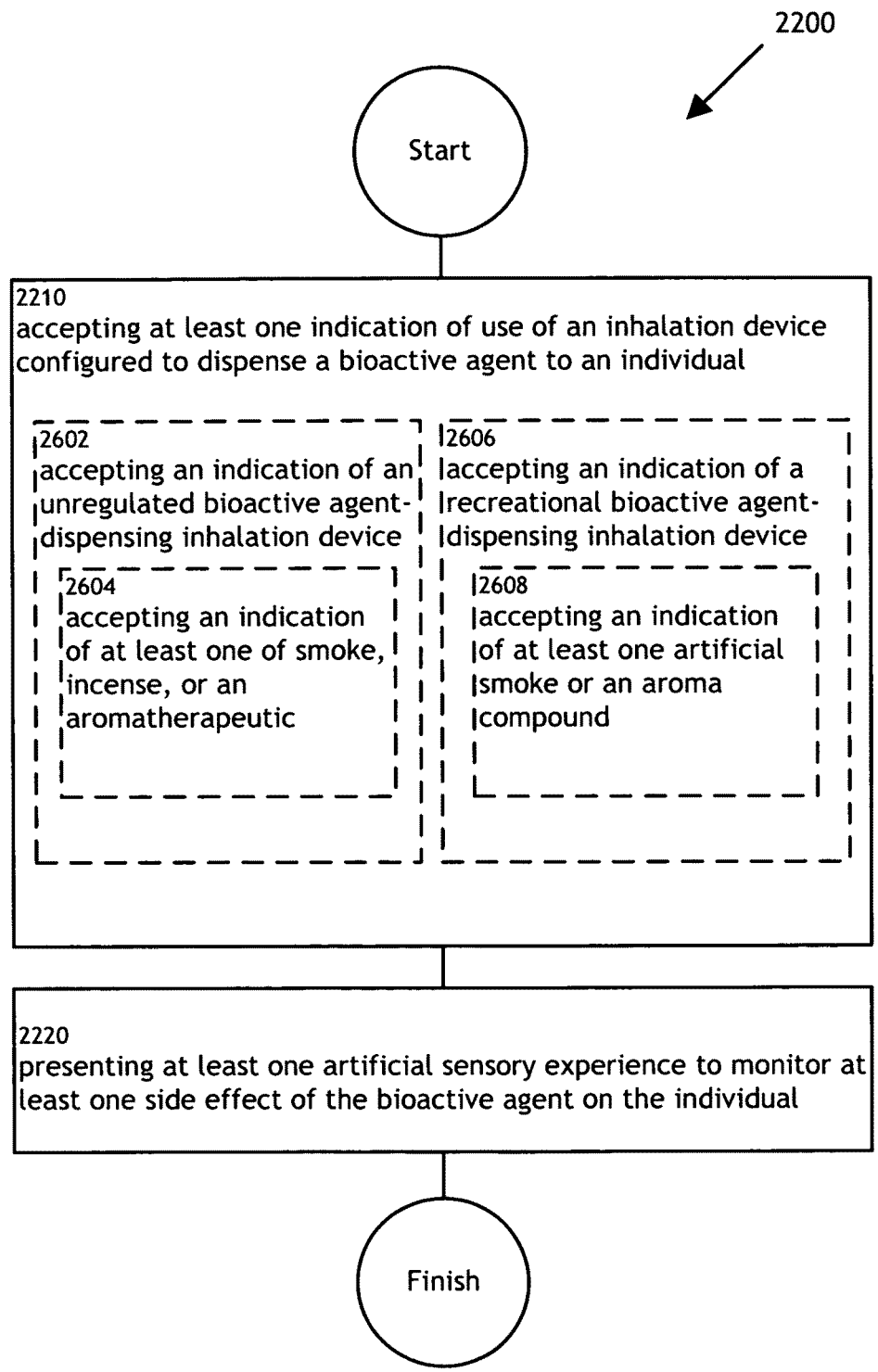
FIG. 26 illustrates an alternative embodiment of the operational flow of FIG. 22.

FIG. 26 illustrates alternative embodiments of the example operational flow 2200 of FIG. 22. FIG. 26 illustrates example embodiments where the operation 2210 may include at least one additional operation. Additional operations may include operation 2602, operation 2604, operation 2606, and/or operation 2608.

Operation 2602 illustrates accepting an indication of an unregulated bioactive agent-dispensing inhalation device. For example, as shown in FIGS. 18 through 21, unregulated bioactive agent accepter module 2020 may accept an indication of an unregulated bioactive agent-dispensing device. In one embodiment, unregulated bioactive agent accepter module 2020 may accept an indication of an aromatherapeutic-dispensing device. In some instances, unregulated bioactive agent accepter module 2020 may include a computer processor and/or an input device, for example a touchscreen user interface.

Further, operation 2604 illustrates accepting an indication of at least one of smoke, incense, or an aromatherapeutic. For example, as shown in FIGS. 18 through 21, unregulated inhalation agent accepter module 2022 may detect an indication of at least one of smoke, incense, or an aromatherapeutic. In one embodiment, unregulated inhalation agent accepter module 2022 may detect an indication of smoke. Smoke may include the collection of airborne colloids. Some uses of smoke may include simulation of a campfire and/or the use of smoke in a ritual when incense, sage, and/or a resin are burned to produce a smell for a spiritual purpose. Incense may include an aromatic biotic material and/or the smoke released when the aromatic biotic material is burned. Incense may be used for religious, practical, and/or aesthetic purposes. An aromatherapeutic may include a volatile material, such as an essential oil. Some examples of an aromatherapeutic may include essential oils (eucalyptus oil and/or grapefruit oil), absolutes (jasmine and/or rose absolute), herbal distillates (lemon balm and/or chamomile), and/or a volatile medication, such as a decongestant with menthol. The volatile material may be applied using aerial diffusion, direct inhalation, and/or a topical application. In another embodiment, unregulated inhalation agent accepter module 2022 may detect incense with a smoke detector. In some instances, unregulated inhalation agent accepter module 2022 may include a computer processor and/or detection means, such as an oxygen detector and/or a smoke detector.

Operation 2606 illustrates accepting an indication of a recreational bioactive agent-dispensing inhalation device. For example, as shown in FIGS. 18 through 21, recreational agent device accepter module 2024 may accept an indication of a recreational bioactive agent-dispensing inhalation device. In one embodiment, recreational agent device accepter module 2024 may accept an indication of a recreational bioactive agent-dispensing inhalation device. Some examples of a recreational bioactive agent may include an aroma compound used for aromatherapy and/or artificial smoke. Other examples of a recreational bioactive agent may include incense and/or smoke, such as incense and/or smoke used in a religious rite. In some instances, recreational agent device accepter module 2024 may include a computer processor.

Further, operation 2608 illustrates accepting an indication of at least one artificial smoke or an aroma compound. For example, as shown in FIGS. 18 through 21, recreational bioactive agent accepter module 2026 may accept an indication of at least one artificial smoke or an aroma compound. In one embodiment, recreational bioactive agent accepter module 2026 may accept an indication of artificial smoke while experiencing a virtual world. In another embodiment, recreational bioactive agent accepter module 2026 may accept an indication of lemon oil while experiencing an artificial sensory experience. In this embodiment, the use of lemon oil as an aromatherapeutic may serve to enhance a user's mood and/or provide relaxation. In some instances, recreational bioactive agent accepter module 2026 may include a computer processor.

FIG. 27 illustrates alternative embodiments of the example operational flow 2200 of FIG. 22. FIG. 27 illustrates example embodiments where the operation 2220 may include at least one additional operation. Additional operations may include operation 2702, operation 2704, and/or operation 2706.

Operation 2702 illustrates receiving data from an automated medical device. For example, as shown in FIGS. 18 through 21, automated medical device receiver module 2102 may receive data from an automated medical device, such as an electrocardiograph. An automated medical device may include a medical monitor, or a device that senses a patient's vital signs and communicates the results to a monitor and/or a user 118. Some examples of an automated medical device may include an electrocardiograph, such as a Holter monitor, medical imaging machines, such as an ultrasound machine and/or a magnetic resonance imaging machine, analysis instrumentation, such as a blood glucose meter, and/or a pulse oximeter. Other examples of an automated medical device may include a pedometer, a heart rate monitor, a blood pressure monitor, a body-fat analyzer, and/or a neurophysiological monitor. Additionally, a multi-parameter automated medical device may simultaneously measure and/or track multiple vital signs. One example of an automated device may include a tele-medicine application, further described in Jeanpierre, L. et al., *Automated medical diagnosis with fuzzy stochastic models: monitoring chronic diseases*, ACTA BIOTHERETICA, 52(4):291-311 (2004), which is incorporated herein by reference. In one embodiment, automated medical device receiver module 2102 may receive data from an electrocardiograph while an individual is experiencing a combined artificial sensory experience and an inhaled bioactive agent. In some instances, automated medical device receiver module 2102 may include a computer processor and/or a monitor coupled to a computer processor.

Operation 2704 illustrates presenting a sensate experience. For example, as shown in FIGS. 18 through 21, sensate experience presenter module 2104 may present a sensate experience as at least a portion of an artificial sensory experience, such as an aroma. A sensate experience may include a thing perceived by the senses, such as an aroma, a sound, a feel, a taste, and/or a sight. In some instances, sensate experience presenter module 2104 may include a computer processor.

Further, operation 2706 illustrates presenting at least one of an olfactory stimulus, a haptic stimulus, a visual stimulus, an auditory stimulus, or a taste stimulus for monitoring the at least one desired effect of the bioactive agent. For example, as shown in FIGS. 18 through 21, stimulus presenter module 2106 may present at least one of an auditory stimulus, such as music with an upbeat tempo, to monitor an effect of the bioactive agent, such as an inhaled antidepressant. In this example, presenting a suitable auditory stimulus and monitoring an individual's reaction, such as attention, alertness, and/or receptivity to the upbeat tempo music, may indicate a decrease in depression and may serve to monitor the inhaled antidepressant. Further discussion regarding an olfactory stimulus may be found in Shaw, D. et al., *Anxiolytic effects of lavender oil inhalation on open-field behaviour in rats*, PHYTOMEDICINE, 14(9):613-20 (2007); Marlier, L. et al., *Olfactory Stimulation Precents Apnea in Premature Newborns*, PEDIATRICS, 115(1):83-88 (2005); and Murayama et al., U.S. Pat. No. 6,282,458; each incorporated by reference. In one embodiment, stimulus presenter module 2106 may present a haptic stimulus suitable to be combined with an inhaled bioactive agent. In this embodiment, the haptic stimulus may include touching and detecting a rough friction-causing surface, in an individual with a sensory deficit, such that detection of and/or reaction to the rough friction-causing surface indicates improvement of the sensory deficit. Detection of a rough surface combined with administration of a bioactive agent, such as a growth factor protein used for stimulating nerve regeneration, may serve to monitor an effect and/or efficacy of the bioactive agent in reducing and/or eliminating the sensory deficit. Further discussion regarding human perception of friction and growth factor proteins may be found respectively in Lawrence, D. A. et al., *Human Perception of Friction in Haptic Interfaces, Human Perceptual Thresholds of Friction in Haptic Interfaces*, PROC. ASME DYNAMIC SYSTEMS AND CONTROL DIVISION, DSC-Vol. 64, pp. 287-294, ASME INT. MECH. ENGR. CONG. & EXPO., Anaheim, Calif., November 1998; and Washington University In St. Louis (Jul. 26, 2002), *New Horizons Of Nerve Repair: Biomedical Engineer Trips Up Proteins In Nerve Regeneration System*, SCIENCEDAILY. Retrieved Jul. 2, 2008, from http://www.sciencedaily.com/releases/2002/07/020725082253.htm.; both incorporated herein by reference. Further discussion regarding a haptic stimulus and/or an auditory stimulus may be found in Canadas-Quesada, F. J. et al., *Improvement of Perceived Stiffness Using Auditory Stimuli in Haptic Virtual Reality*, IEEE MELECON, May 16-19, Benalmadena (Málaga) Spain; and Rizzo, A. et al., *Virtual Therapeutic Environments with Haptics: An Interdisciplinary Approach for Developing Post-Stroke Rehabilitation Systems*, Proceedings of The 2005 International Conference on Computers for People with Special Needs, 70-76, CPSN 2005, Las Vegas, Nev., Jun. 20-23, 2005, both incorporated herein by reference. Presenting stimuli and/or a reaction to stimuli, such as an olfactory stimulus, a haptic stimulus, a visual stimulus, an auditory stimulus, or a taste stimulus, may elicit reactions in individual 134 that indicate at least one effect of the bioactive agent and may serve to monitor the at least one effect of the bioactive agent. In some instances, stimulus presenter module 2106 may include a computer processor.

FIG. 28 illustrates alternative embodiments of the example operational flow 2200 of FIG. 22. FIG. 28 illustrates example embodiments where the operation 2220 may include at least one additional operation. Additional operations may include operation 2802, and/or operation 2804.

Operation 2802 illustrates presenting an artificial sensory experience implemented on a mobile device. For example, as shown in FIGS. 18 through 21, mobile device presenter module 2108 may present a bright background color theme in a virtual world implemented on a mobile device, such as a web browser on a laptop computer having wireless capability and a battery. In this example, presenting a bright background color theme on a mobile device combined with a bioactive agent, for example an antidepressant, may elicit a reaction by individual 134, such as increased activity and less depressive behavior (e.g., more message posting and less reclusive behavior while interacting with others on a social networking website, such as MySpace.com) indicating an effect of the bioactive agent and serving to monitor an effect of the bioactive agent. Some examples of a mobile device may include a laptop or notebook computer, a personal digital assistant (PDA), an ipod, a smartphone, an Enterprise digital assistant (EDA), and/or a pager. One example of a mobile device for use in a virtual environment may include multiple access terminals and a removable memory card, further discussed in Viktorsson et al., U.S. Pat. No. 6,397,080, which is incorporated herein by reference. In some instances, mobile device presenter module 2108 may include a computer processor.

Operation 2804 illustrates presenting a virtual world, a modification to a virtual world, a computer game, a modification to a computer game, a website, a modification to a website, an online course, or a modification to an online course. For example, as shown in FIGS. 18 through 21, virtual object presenter module 2110 may present a virtual world suitable for combining with an inhaled bioactive agent. A virtual world may include a computer-based simulated environment intended for its users to inhabit and interact via avatars. Some examples of a virtual world may include a massively multiplayer online role-playing game (MMORPG), such as World of Warcraft, a snow world, and/or simple virtual geocaching, such as on Google Earth. In one embodiment, virtual object presenter module 2110 may assign World of Warcraft as a virtual world. A computer game may include a video game and/or other software-based game executed on a personal computer, an arcade machine, and/or other video game console. Some examples of a computer game may include Super Mario 64, World of Warcraft, and/or Guild Wars. A website may include a collection of webpages, images, videos, and/or other digital assets hosted on at least one webserver and may be accessible via the Internet. Some examples of a website may include yahoo.com and/or MySpace.com. In one embodiment, virtual object presenter module 2110 may present the use of a website including Facebook.com. An online course may include an online educational experience such as a tutorial, a lesson, and/or an online class. Some examples of an online course may include a HTML tutorial, an online piano lesson, and/or an online degree program from the University of Phoenix. In another embodiment, virtual object presenter module 2110 may present an online social skills tutorial to help individual 134 overcome a social phobia where the tutorial is coupled with a bioactive agent, such as an antianxiety medication. Examples of a modification to a virtual world, a computer game, a website, and/or an online course may include restricting access, granting access, altering a visual object, altering a color scheme, modifying text, and/or altering a sound, music, a voice, and/or ambient sound. In some instances, virtual object presenter module 2110 may include a computer processor configured to match an artificial sensory experience with a bioactive agent based on the individual.

FIG. 29 illustrates alternative embodiments of the example operational flow 2200 of FIG. 22. FIG. 29 illustrates example embodiments where the operation 2220 may include at least one additional operation. Additional operations may include operation 2902.

Operation 2902 illustrates presenting an artificial sensory experience to monitor at least one of physical activity, body weight, body mass index, heart rate, blood oxygen level, or blood pressure temporally associated with an artificial sensory experience. For example, as shown in FIGS. 18 through 21, physiological characteristic monitor presenter module 2112 may present an individual's heart rate. Physical activity may include any form of exercise, movement, and/or bodily activity. Some examples of a physical activity may include exercise, body movement, walking, running, and/or muscle stretching. Presenting and/or monitoring a physical activity may include using a pedometer, an accelerometer, for example, available from New-Lifestyles, Inc., Lee's Summit, Mo., and/or other devices, such as actometers, further discussed in Zhang et al., *Measurement of Human Daily Physical Activity*, OBESITY RESEARCH, 11(1):33-40 (2003), which is incorporated herein by reference. Presenting and/or monitoring a body weight and/or a body mass index may include using a scale and/or a computing device. In one embodiment, physiological characteristic monitor presenter module 2112 may present and/or monitor a body mass index of an individual experiencing a Wii Fitness game while being administered a weight loss medication by using a scale 3220 coupled with a computer processor. In the same embodiment, scale 3220 and computer processor may constantly monitor the body mass index of the individual 134. Presenting and/or monitoring a heart rate may include measuring work done by the heart, such as measuring beats per unit time and/or a pulse. Presenting and/or monitoring a blood oxygen level may include utilizing a pulse oximeter and/or measuring oxygen saturation directly through a blood sample. Presenting and/or monitoring blood pressure may include utilizing a sphygmomanometer, which may be coupled to a computer processor or other monitoring device. Presenting and/or monitoring physical activity, a heart rate, a blood oxygen level, and/or blood pressure when an individual is experiencing an artificial sensory experience may serve to determine the efficacy of a bioactive agent. For example, when an antianxiety medication is administered to an individual prior to and/or during an artificial sensory experience, such as a spider world designed to overcome a spider phobia, physiological characteristic monitor presenter module 2112 may monitor a heart rate in order to determine whether the antianxiety medication is effective. In the above example, the individual's heart rate may decrease due to a decrease in anxiety as the antianxiety medication takes effect indicating drug efficacy. Additionally, physiological characteristic monitor presenter module 2112 may monitor before, during, and/or after experiencing an artificial sensory experience. In some instances, physiological characteristic monitor presenter module 2112 may include a computer processor and/or medical instrumentation.

Figure 30:
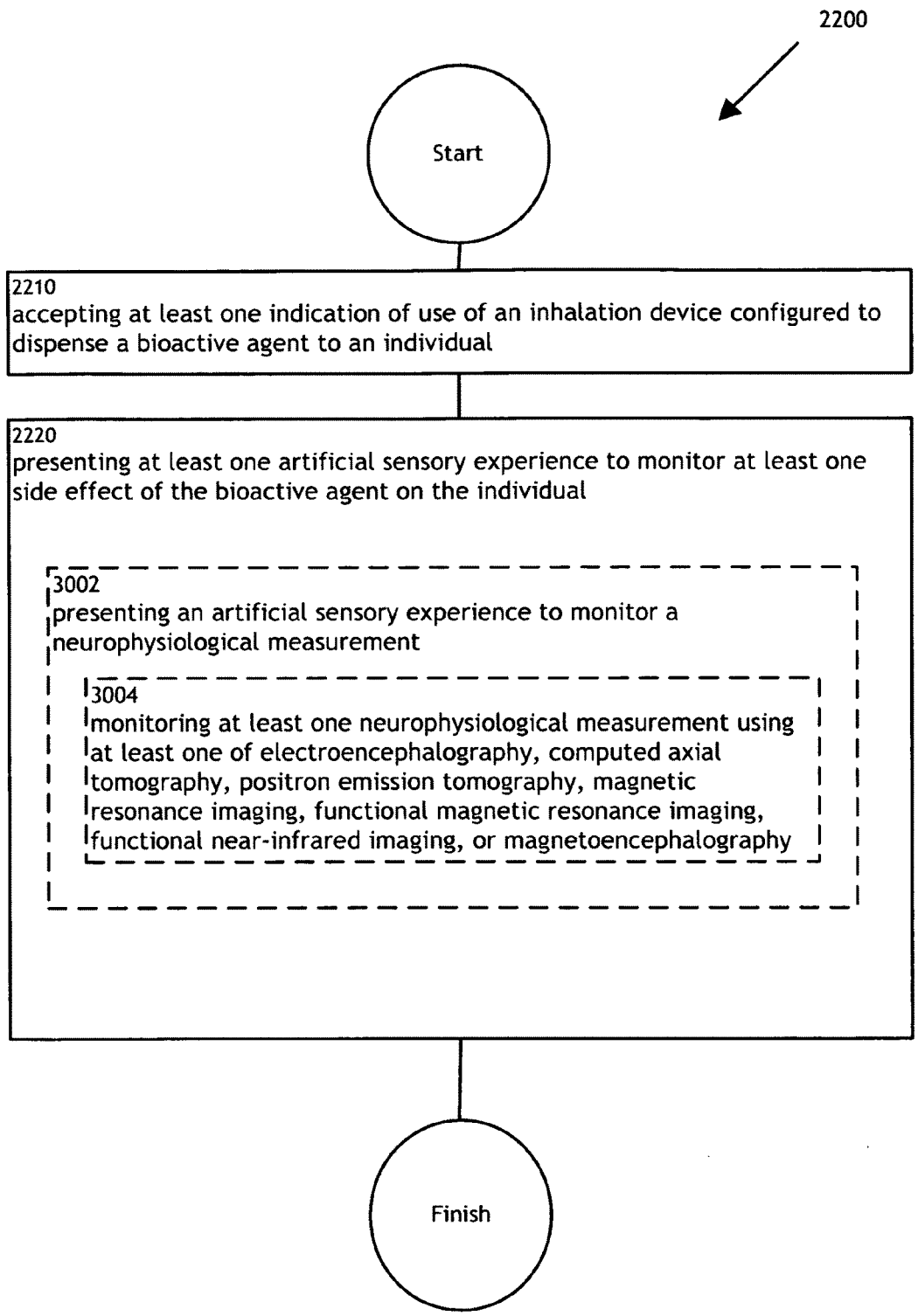
FIG. 30 illustrates an alternative embodiment of the operational flow of FIG. 22.

FIG. 30 illustrates alternative embodiments of the example operational flow 2200 of FIG. 22. FIG. 30 illustrates example embodiments where the operation 2220 may include at least one additional operation. Additional operations may include operation 3002, and/or operation 3004.

Operation 3002 illustrates presenting an artificial sensory experience to monitor a neurophysiological measurement. For example, as shown in FIGS. 18 through 21, neurophysiological measurement monitor presenter module 2114 may present an artificial sensory experience to monitor a neurophysiological measurement, such as a measurement of the activation signal of muscles (electromyography) and/or the measurement of transcranial magnetic stimulation. A neurophysiological measurement may include a measurement of the brain, nervous system, and/or neuromonitoring. In some instances, neurophysiological measurement monitor presenter module 2114 may include a computer processor, a monitor, a printer, a mobile device, and/or a medical device, such as device configured to measure somatosensory evoked potentials (SSEPs), auditory brainstem response (ABR), and/or scalp or remote sensors used in electroencephalography (EEG).

Further, operation 3004 illustrates monitoring at least one neurophysiological measurement using at least one of electroencephalography, computed axial tomography, positron emission tomography, magnetic resonance imaging, functional magnetic resonance imaging, functional near-infrared imaging, or magnetoencephalography. For example, as shown in FIGS. 18 through 21, neurophysiological characteristic monitor presenter module 2116 may monitor at least one neurophysiological measurement using at least one of electroencephalography, computed axial tomography, positron emission tomography, magnetic resonance imaging, functional magnetic resonance imaging, functional near-infrared imaging, or magnetoencephalography. In some instances, neurophysiological characteristic monitor presenter module 2116 may include a computer processor, and/or a medical device, such as an apparatus configured to perform a computed axial tomography scan.

Electroencephalography may include measuring the electrical activity of the brain by recording from electrodes placed on the scalp or, in special cases, subdurally, or in the cerebral cortex, or from remote sensors. The resulting traces are known as an electroencephalogram (EEG) and represent a summation of post-synaptic potentials from a Large number of neurons. EEG is most sensitive to a particular set of post-synaptic potentials: those which are generated in superficial layers of the cortex, on the crests of gyri directly abutting the skull and radial to the skull. Dendrites that are deeper in the cortex, inside sulci, are in midline or deep structures (such as the cingulate gyrus or hippocampus) or that produce currents that are tangential to the skull make a smaller contribution to the EEG signal.

One application of EEG is event-related potential (ERP) analysis. An ERP is any measured brain response that is directly the result of a thought or perception. ERPs can be reliably measured using electroencephalography (EEG), a procedure that measures electrical activity of the brain, typically through the skull and scalp. As the EEG reflects thousands of simultaneously ongoing brain processes, the brain response to a certain stimulus or event of interest is usually not visible in the EEG. One of the most robust features of the ERP response is a response to unpredictable stimuli. This response is known as the P300 (P3) and manifests as a positive deflection in voltage approximately 300 milliseconds after the stimulus is presented.

A two-channel wireless brain wave monitoring system powered by a thermo-electric generator has been developed by IMEC (Interuniversity Microelectronics Centre, Leuven, Belgium). This device uses the body heat dissipated naturally from the forehead as a means to generate its electrical power. The wearable EEG system operates autonomously with no need to change or recharge batteries. The EEG monitor prototype is wearable and integrated into a headband where it consumes 0.8 milliwatts. A digital signal processing block encodes extracted EEG data, which is sent to a PC via a 2.4-GHz wireless radio Link. The thermoelectric generator is mounted on the forehead and converts the heat flow between the skin and air into electrical power. The generator is composed of 10 thermoelectric units interconnected in a flexible way. At room temperature, the generated power is about 2 to 2.5-mW or 0.03-mW per square centimeter, which is the theoretical limit of power generation from the human skin. Such a device is proposed to associate emotion with EEG signals. See Clarke, "IMEC has a brain wave: feed EEG emotion back into games," EE Times online, http://www.eetimes.eu/design/202801063 (Nov. 1, 2007).

Computed axial tomography may include medical imaging employing tomography and digital geometry processing for generating a three-dimensional image of the inside of an object from a large series of two-dimensional X-ray images taken around a single axis of rotation. Positron emission tomography may include a nuclear medicine imaging technique, which produces a three-dimensional image and/or map of at least one functional process in the body. The system detects pairs of gamma rays emitted indirectly by a positron-emitting radionuclide (a tracer), which is introduced into the body on a biologically active molecule. Images of tracer concentration in 3-dimensional space within the body may then be reconstructed by computer analysis. Magnetic resonance imaging may include a medical imaging technique using a magnetic field to align the nuclear magnetization of hydrogen atoms in water in the body, resulting in an image of the body. Functional magnetic resonance imaging may include and imaging method for measuring haemodynamic response related to neural activity in the brain or spinal cord. Functional near-infrared imaging (fNIR) may include a spectroscopic neuro-imaging method for measuring the level of neuronal activity in the brain. Functional near-infrared imaging (fNIR) is based on neuro-vascular coupling, or the relationship between metabolic activity and oxygen level (oxygenated hemoglobin) in feeding blood vessels.

Magnetoencephalography includes measuring the magnetic fields produced by electrical activity in the brain using magnetometers such as superconducting quantum interference devices (SQUIDs) or other devices. Smaller magnetometers are in development, including a mini-magnetometer that uses a single milliwatt infrared laser to excite rubidium in the context of an applied perpendicular magnetic field. The amount of laser light absorbed by the rubidium atoms varies predictably with the magnetic field, providing a reference scale for measuring the field. The stronger the magnetic field, the more light is absorbed. Such a system is currently sensitive to the 70 fT range, and is expected to increase in sensitivity to the 10 fT range. See Physorg.com, "New mini-sensor may have biomedical and security applications," Nov. 1, 2007, http://www.physorg.com/news113151078.html, which is incorporated herein by reference.

Figure 31:
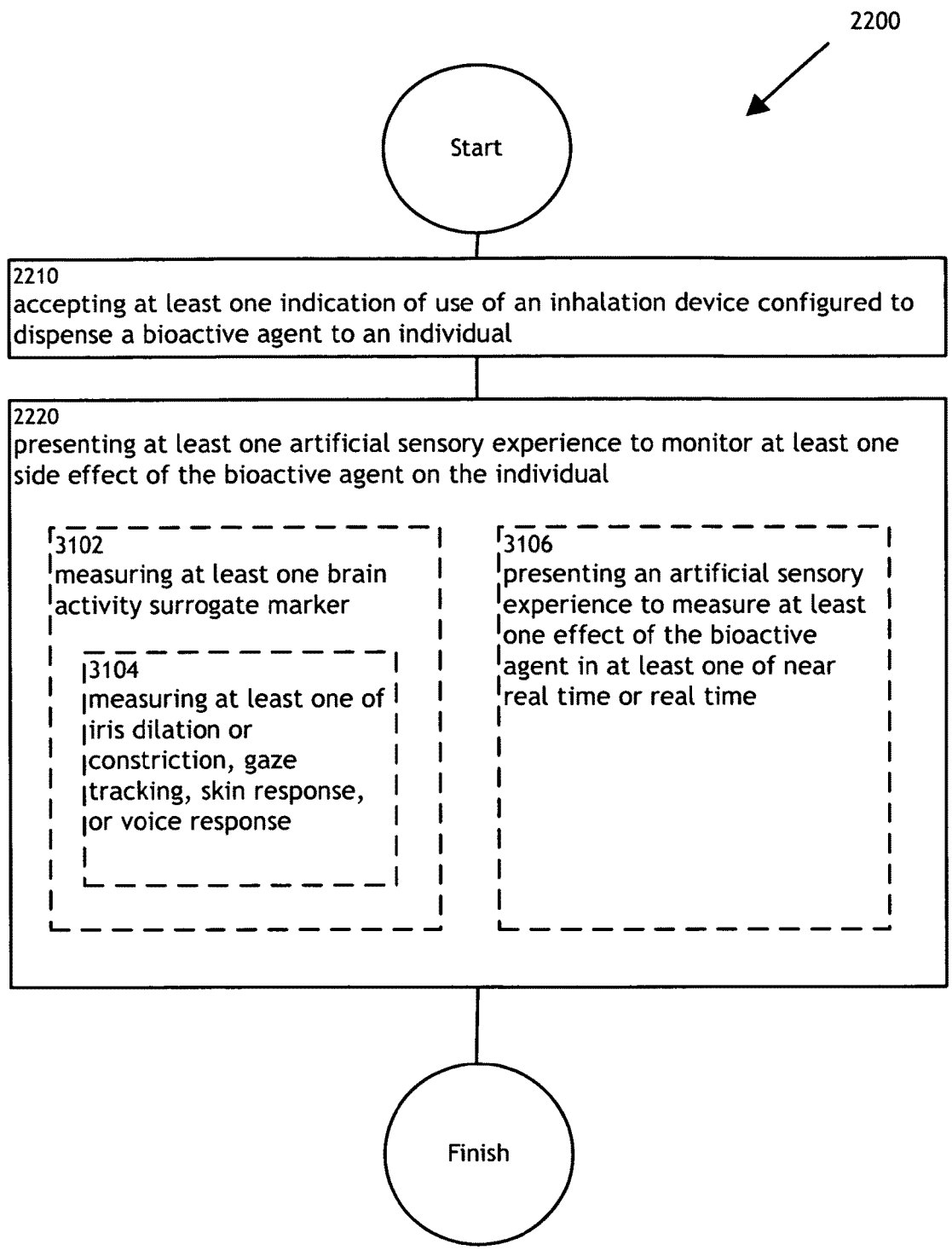
FIG. 31 illustrates an alternative embodiment of the operational flow of FIG. 22.

FIG. 31 illustrates alternative embodiments of the example operational flow 2200 of FIG. 22. FIG. 31 illustrates example embodiments where the operation 2220 may include at least one additional operation. Additional operations may include operation 3102, operation 3104, and/or operation 3106.

Operation 3102 illustrates measuring at Least one brain activity surrogate marker. For example, as shown in FIGS. 18 through 21, brain activity measurer module 2118 may measure a brain activity surrogate marker. In some instances, brain activity measurer module 2118 may include a computer processor and/or medical instrumentality configured to measure a surrogate marker, such as a stethoscope, a face recognition system, and/or a sphygmomanometer. Brain activity surrogate markers may include indicators of attention, approval, disapproval, recognition, cognition, memory, trust, or the like in response to a stimulus, other than measurement of brain activity associated with the stimulus. Some examples of surrogate markers may include a skin response to a stimulus; a face pattern indicative of approval, disapproval, or emotional state; eye movements or pupil movements indicating visual attention to an object; voice stress patterns indicative of a mental state, or the like. Surrogate markers may be used in conjunction with brain activity measurements for higher confidence in a predictive or interpretational outcome. For example, brain activation of the caudate nucleus in combination with calm voice patterns may increase confidence in a predictor of trust between a subject and a stimulus. Additional discussion regarding surrogate markers may be found in Cohn, J. N., *Introduction to Surrogate Markers*, CIRCULATION 109:IV20-21, American Heart Association, (2004), which is incorporated herein by reference.

For example, emotion links to cognition, motivation, memory, consciousness, and learning and developmental systems. Affective communication depends on complex, rule-based systems with multiple channels and redundancy built into the exchange system, in order to compensate if one channel fails. Channels can include all five senses: for example, increased heart-rate or sweating may show tension or agitation and can be heard, seen, touched, smelt or tasted. Emotional exchanges may be visible displays of body tension or movement, gestures, posture, facial expressions or use of personal space; or audible displays such as tone of voice, choice of pitch contour, choice of words, speech rate, etc. Humans also use touch, smelt, adornment, fashion, architecture, mass media, and consumer products to communicate our emotional state. Universals of emotion that cross cultural boundaries have been identified, and cultural differences have also been identified. For example 'love' is generally categorized as a positive emotion in Western societies, but in certain Eastern cultures there is also a concept for 'sad love.' Accordingly, universal emotional triggers may be used to transcend cultural barriers.

When communicating with computers, people often treat new media as if they were dealing with real people. They often follow complex social rules for interaction and modify their communication to suit their perceived conversation partner. Much research has focused on the use of facial actions and ways of coding them. Speech recognition systems have also attracted attention as they grow in capability and reliability, and can recognize both verbal messages conveyed by spoken words, and non verbal messages, such as those conveyed by pitch contours.

System responses and means of expressing emotions also vary. Innovative prototypes are emerging designed to respond indirectly, so the user is relatively unaware of the response: for example by adaptation of material, such as changing pace or simplifying or expanding content. Other systems use text, voice technology, visual agents, or avatars to communicate. See Axelrod et al., "Smoke and Mirrors: Gathering User Requirements for Emerging Affective Systems," 26th Int. Conf. Information Technology Interfaces/TI 2004, Jun. 7-10, 2004, Cavtat, Croatia, pp. 323-328, which is incorporated herein by reference.

Further, operation 3104 illustrates measuring at least one of iris dilation or constriction, gaze tracking, skin response, or voice response. For example, as shown in FIGS. 18 through 21, brain marker measurer module 2120 may measure voice response of individual 134. In some instances, brain marker measurer module 2120 may include a computer processor and/or medical instrumentality, such as a stethoscope and/or a sphygmomanometer. In one embodiment, brain marker measurer module 2120 may record changes in the movement of an individual's iris (with corresponding changes in the size of the pupil) before, during, and/or after administration of a bioactive agent and/or an artificial sensory experience. Such measurements of physiologic activity that indicate brain activity and/or mental state may be carried out at a time that is proximate to administration of a bioactive agent and/or an artificial sensory experience.

In one embodiment, brain marker measurer module 2120 may measure and/or record gaze tracking. In some instances, brain marker measurer module 2120 may include a camera that can monitor a subject's eye movements in order to determine whether the subject looks at a presented characteristic, for example, during a certain time period. For example, a camera may include a smart camera that can capture images, process them and issue control commands within a millisecond time frame. Such smart cameras are commercially available (e.g., Hamamatsu's Intelligent Vision System; http://jp.hamamatsu.com/en/product_info/index.html). Such image capture systems may include dedicated processing elements for each pixel image sensor. Other camera systems may include, for example, a pair of infrared charge coupled device cameras to continuously monitor pupil size and position as a user watches a visual target moving forward and backward. This can provide real-time data relating to pupil accommodation relative to objects on, for example, user interface 116, such as a display. (e.g., http://jp.hamamatsu.com/en/rd/publication/scientific_american/common/pdf/scientific_0608.pdf).

Eye movement and/or iris movement may also be measured by video-based eye trackers. In these systems, a camera focuses on one or both eyes and records eye movement as the viewer looks at a stimulus. Contrast may be used to locate the center of the pupil, and infrared and near-infrared non-collumnated tight may be used to create a corneal reflection. The vector between these two features can be used to compute gaze intersection with a surface after a calibration for an individual 134.

In one embodiment, brain marker measurer module 2120 may measure and/or record skin response. Brain activity may be determined by detection of a skin response associated with a stimulus. One skin response that may correlate with mental state and/or brain activity is galvanic skin response (GSR), also known as electrodermal response (EDR), psychogatvanic reflex (PGR), or skin conductance response (SCR). This is a change in the electrical resistance of the skin. There is a relationship between sympathetic nerve activity and emotional arousal, although one may not be able to identify the specific emotion being elicited. The GSR is highly sensitive to emotions in some people. Fear, anger, startle response, orienting response, and sexual feelings are all among the emotions which may produce similar GSR responses. GSR is typically measured using electrodes to measure skin electrical signals.

For example, an Ultimate Game study measured skin-conductance responses as a surrogate marker or autonomic index for affective state, and found higher skin conductance activity for unfair offers, and as with insular activation in the brain, this measure discriminated between acceptances and rejections of these offers. See Sanfey, "Social Decision-Making: Insights from Game Theory and Neuroscience," Science, vol. 318, pp. 598-601 (26 Oct. 2007), which is incorporated herein by reference. Other skin responses may include flushing, blushing, goose bumps, sweating, or the like.

In one embodiment, brain marker measurer module 2120 may measure and/or record voice response. Voice response may include speech captured by a microphone during presentation of a characteristic. Speech or voice can be measured, for example, by examining voice, song, and/or other vocal utterances of a subject before, during, and/or after administration of a bioactive agent and/or an artificial sensory experience to an individual 134. Such measurements may include, for example, as discussed above, layered voice analysis, voice stress analysis, or the like.

The reaction of an individual to an administered bioactive agent and/or an artificial sensory experience, such as an event in a virtual world may be a recognizable vocal exclamation such as "Wow, that's nice!" that may be detectable by a brain marker measurer module 2120, such as a microphone monitoring the subject while being administered an artificial sensory experience. A brain marker measurer module 2120 may include a voice response module and/or a speech recognition function, such as a software program or computational device, that can identify and/or record an utterance of a subject as speech or voice data.

Operation 3106 illustrates presenting an artificial sensory experience to measure at least one effect of the bioactive agent in at least one of near real time or real time. For example, as shown in FIGS. 18 through 21, real time presenter module 2122 may present an artificial sensory experience to measure an effect of the bioactive agent in near real time. A near real time event may include the current time of an event plus processing time. In one embodiment, real time presenter module 2122 may present a virtual world, such as World of Warcraft, to measure a bioactive agent effect in near real time. A further example of presenting in real time, for example real-time medical alerting, may be found in McGovern, U.S. Pat. No. 6,909,359, which is incorporated herein by reference. In some instances, real time presenter module 2122 may include a computer processor.

FIG. 32 illustrates alternative embodiments of the example operational flow 2200 of FIG. 22. FIG. 32 illustrates example embodiments where the operation 2220 may include at least one additional operation. Additional operations may include operation 3202, and/or operation 3204.

Operation 3202 illustrates monitoring at least one of visual field test function output, eye movement test function output, pupil movement test function output, face pattern test function output, hearing test function output, or voice test function output. For example, as shown in FIGS. 18 through 21, function output monitorer module 2124 may monitor a visual field test function output. For example, an individual 134 may undertake a visual field test, for example, on a personal computer so as to obtain visual field test data. A visual field test function may include, for example, one or more visual field test functions, one or more pointing device manipulation test functions, and/or one more reading test functions. Visual field attributes are indicators of an individual's ability to see directly ahead and peripherally. An example of a visual field test function may be a measure of an individual's gross visual acuity, for example using a Snellen eye chart or visual equivalent on a display. Alternatively, a campimeter may be used to conduct a visual field test. Such visual field tests or campimeters are available online (e.g., at http://www.testvision.org/what_is.htm). Visual field testing could be done in the context of, for example, new email alerts that require clicking and that appear in various locations on a display. Based upon the location of decreased visual field, the defect can be localized, for example in a quadrant system.

In an embodiment, function output monitorer module 2124 may measure eye movement test function output. An eye movement test function or a pupil movement test function may include, for example, one or more eye movement test functions, one more pupil movement test functions, and/or one or more pointing device manipulation test functions. An example of an eye movement test function may be a measurement of an individual's ability to follow a target on a display with her eyes throughout a 360° range. Such testing may be done in the context of an individual experiencing an artificial sensory experience or participating in a virtual world. In such examples, eye movement test function output may be obtained through a camera in place as a monitoring device that can monitor the eye movements of the individual during interaction with administration of the artificial sensory experience and/or the bioactive agent. Another example of an eye movement test function may include eye tracking data from an individual monitoring device, such as a video communication device, for example, when a task requires tracking objects on a display, reading, or during resting states between activities in an application. A further example includes pupil movement tracking data from the individual 134 at rest or during an activity required by an application or user-health test function.

In an embodiment, function output monitorer module 2124 may measure pupil movement test function output. An example of a pupil movement test function may be a measure of an individual's pupils when exposed to light or objects at various distances. A pupillary movement test may assess the size and symmetry of an individual's pupils before and after a stimulus, such as light or focal point. In the above embodiments, altered eye movement ability and/or pupil movement ability may indicate and/or monitor a desired effect of an administered bioactive agent.

In an embodiment, function output monitorer module 2124 may measure face pattern test function output. A face pattern test function may include, for example, one or more face movement test functions involving an individual's ability to move the muscles of the face. An example of a face pattern test function may be a comparison of an individual's face while at rest, specifically looking for nasolabial fold flattening or drooping of the corner of the mouth, with the individual's face while moving certain facial features. The individual may be asked to raise her eyebrows, wrinkle her forehead, show her teeth, puff out her cheeks, or close her eyes tight. Such testing may be done via facial pattern recognition software used in conjunction with, for example, an artificial sensory experience. Abnormalities in facial expression or pattern may indicate efficacy of and/or a desired effect of a bioactive agent while experiencing an artificial sensory experience.

In one embodiment, function output monitorer module 2124 may measure measuring hearing test function output. A hearing test function may include, for example, one or more conversation hearing test functions such as one or more tests of an individual's ability to detect conversation, for example in a virtual world and/or an artificial sensory experience scenario. An example of a hearing test function may include a gross hearing assessment of an individual's ability to hear sounds. This may be done by simply presenting sounds to the individual or determining if the individual can hear sounds presented to each of the ears. For example, at least one hearing test device may vary volume settings or sound frequency over time to test an individual's hearing. For example, a mobile phone device or other communication device may carry out various hearing test functions. Altered hearing ability may indicate efficacy of and/or a desired effect of a bioactive agent while experiencing an artificial sensory experience.

In one embodiment, function output monitorer module 2124 may measure measuring hearing test function output. A voice test function may include, for example, one or more voice test functions. An example of a voice test function may be a measure of symmetrical elevation of the palate when the user says "aah" or a test of the gag reflex. A voice test function may monitor user voice frequency or volume data during, for example, gaming, such as a virtual world, an artificial sensory experience, videoconferencing, speech recognition software use, or mobile phone use. A voice test function may assess an individual's ability to make simple sounds or to say words, for example, consistently with an established voice pattern for the individual. An abnormal or altered voice may indicate efficacy of and/or a desired effect of a bioactive agent while experiencing an artificial sensory experience.

In some instances, function output monitorer module 2124 may include a computer processor and/or medical instrumentality, such as that described in the above paragraphs. One skilled in the art may select, establish or determine an appropriate pupil movement test function for monitoring a desired bioactive agent effect. Test function sets and test functions may be chosen by one skilled in the art based on knowledge, direct experience, or using available resources such as websites, textbooks, journal articles, or the like. An example of a relevant website can be found in the online Merck Manual at http://www.merck.com/mmhe/sec06/ch077/ch077c.html#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16th Ed., McGraw-Hill, New York, 2005; Greenberg, M. S., "Handbook of Neurosurgery," 6th Ed., Thieme, Lakeland, 2006; and Victor, M., and Ropper, A. H., "Adams and Victor's Principles of Neurology," 7th Ed., McGraw-Hill, New York, 2001.

Operation 3204 illustrates monitoring at least one of body movement test function output or motor skill test function output. For example, as shown in FIGS. 18 through 21, test function output monitorer module 2126 may monitor body movement test function output or motor skill test function output. An example of a body movement test function may include prompting an individual 134 to activate or click a specific area on a display to test, for example, arm movement, hand movement, or other body movement or motor skill function. Another example is visual tracking of an individual's body, for example during an artificial sensory experience, wherein changes in facial movement, limb movement, or other body movements are detectable. A further example is testing an individual's ability to move while using a game controller in an artificial sensory experience containing an accelerometer, for example, the Wii remote that is used for transmitting an individual's movement data to a computing device. A body movement test function may perform gait analysis, for example, in the context of video monitoring of the user. A body movement test function may also include a test function of fine movements of the hands and feet. Rapid alternating movements, such as wiping one palm alternately with the palm and dorsum of the other hand, may be tested as well. A common test of coordination is the finger-nose-finger test, in which the user is asked to alternately touch their nose and an examiner's finger as quickly as possible. Alternatively, testing of fine movements of the hands may be tested by measuring an individual's ability to make fine movements of a cursor on a display. To test the accuracy of movements in a way that requires very little strength, an individual may be prompted to repeatedly touch a line drawn on the crease of the individual's thumb with the tip of their forefinger; alternatively, an individual may be prompted to repeatedly touch an object on a touchscreen display. Abnormalities and/or alterations of body movement may indicate the efficacy of and/or a desired effect of a bioactive agent while experiencing an artificial sensory experience.

A motor skill test function may include, for example, one or more deliberate body movement test functions such as one or more tests of an individual's ability to move an object, including objects on a display, e.g., a cursor. An example of a motor skill test function may be a measure of an individual's ability to perform a physical task. A motor skill test function may measure, for example, an individual's ability to traverse a path on a display in straight Line with a pointing device, to type a certain sequence of characters without error, or to type a certain number of characters without repetition. For example, a slowed cursor on a display may indicate a desired effect of a bioactive medication, such as an antianxiety medication. An antianxiety medication may work to calm an individual resulting in a slowed response time and a slowed cursor on a display and indicating a desired effect of a bioactive agent. Alternatively, an individual may be prompted to switch tasks, for example, to alternately type some characters using a keyboard and click on some target with a mouse. If a user has a motor skill deficiency, she may have difficulty stopping one task and starting the other task indicating a desired effect of a bioactive agent during an artificial sensory experience. In some instances, test function output monitorer module 2126 may include a computer processor, computer equipment, such as a touch screen display, and/or medical instrumentality, such as that described in the above paragraphs.

FIG. 33 illustrates alternative embodiments of the example operational flow 2200 of FIG. 22. FIG. 33 illustrates example embodiments where the operation 2220 may include at least one additional operation. Additional operations may include operation 3302, and/or operation 3304.

Operation 3302 illustrates recording at least one monitored effect of the bioactive agent. For example, as shown in FIGS. 18 through 21, recorder module 2128 may record at least one monitored effect of the bioactive agent. Recording a monitored effect may include capturing data including the monitored effect to a record, or a format stored on a storage medium. In one embodiment, recorder module 2128 may record body movement test function output onto a hard disk drive. Other examples of a record and/or storage medium may include flash memory devices, a tape drive, circuitry with non-volatile and/or volatile RAM, an optical disc, for example a CD and/or DVD, and/or a paper record, such as a collection of printed spreadsheets and/or other Lists of data. In an additional embodiment, recorder module 2128 may record a monitored effect by utilizing data acquisition software. Further discussion of data acquisition may be found in Green, T. et al., *PC-Based Medical Data Acquisition and Analysis, cbms*, p. 0159, EIGHTH IEEE SYMPOSIUM ON COMPUTER-BASED MEDICAL SYSTEMS (CBMS'95), 1995, which is incorporated herein by reference. In some instances, recorder module 2128 may include a computer processor and/or other data togging instrumentation, such as NI CompactDAQ hardware, available from National Instruments, Austin, Tex. (http://www.ni.com/dataacquisition/compactdaq/).

Operation 3304 illustrates accepting an indication of a collar configured to dispense a bronchodilator to an individual and presenting a virtual world to monitor an individual's hypertension in response to administration of the bronchodilator. For example, as shown in FIGS. 18 through 21, accepter module 2002 and side effect monitor presenter module 2028 may accept an indication of a collar configured to dispense a bronchodilator to an individual and present a virtual game to monitor an individual's response time to the bronchodilator. In some instances, accepter module 2002 may include a computer processor, a user interface, and/or computer memory. In some instances, side effect monitor presenter module 2028 may include a computer processor.

Figure 34:
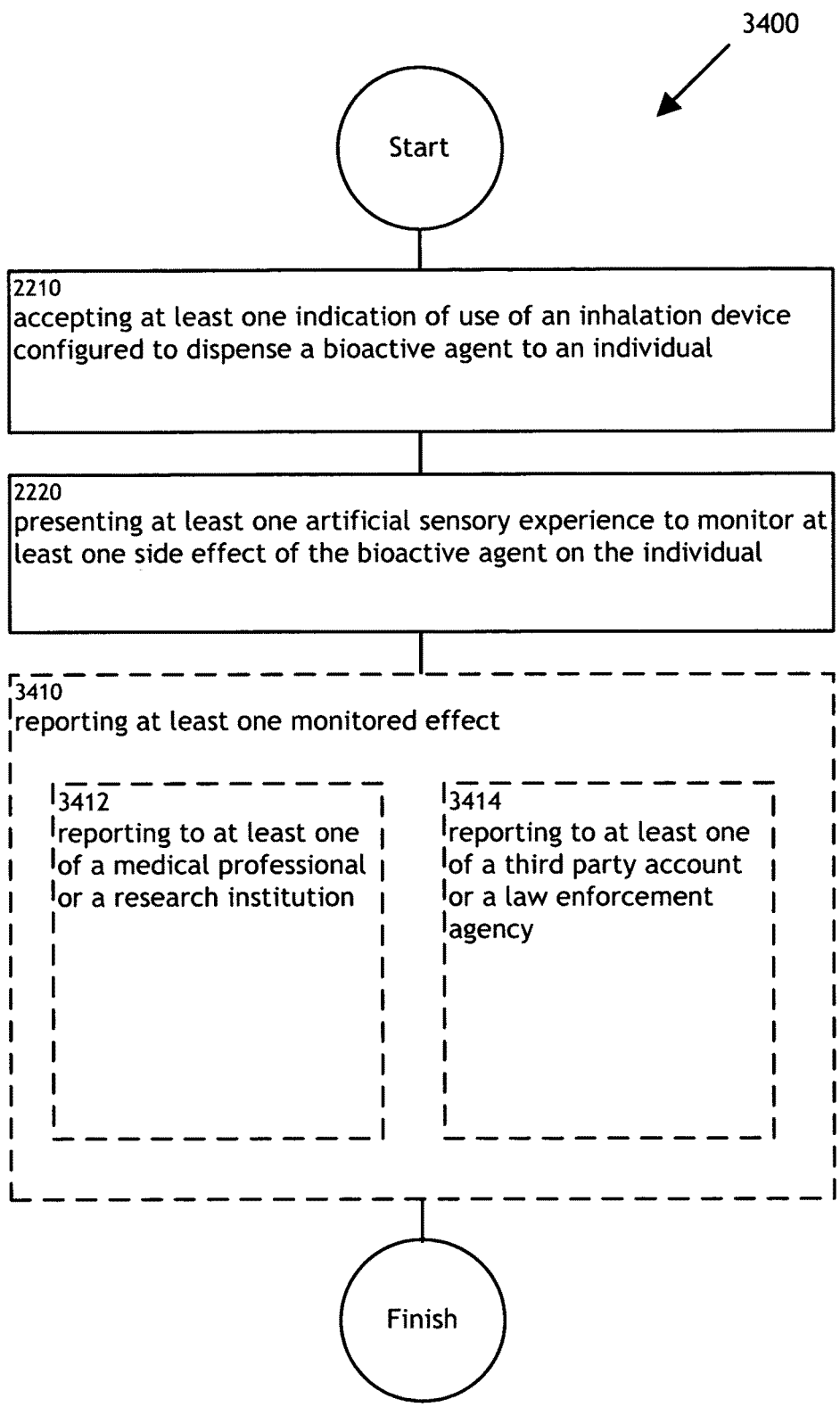
FIG. 34 illustrates an alternative embodiment of the operational flow of FIG. 22.

FIG. 34 illustrates an operational flow 3400 representing example operations related to accepting at least one indication of use of an inhalation device configured to dispense a bioactive agent to an individual, presenting at least one artificial sensory experience to monitor at least one side effect of the bioactive agent on the individual, and reporting at least one monitored effect. FIG. 34 illustrates an example embodiment where the example operational flow 2200 of FIG. 22 may include at Least one additional operation. Additional operations may include operation 3410, operation 3412, and/or operation 3414.

After a start operation, operation 2210, and operation 2220, the operational flow 3400 moves to operation 3410. Operation 3410 illustrates reporting at least one monitored effect. For example, as shown in FIGS. 18 through 21, reporter module 2030 may report at least one monitored effect. Reporting may include relating or passing on information, and/or describing a monitored effect status. In one embodiment, reporter module 2030 may report acquired data including a monitored effect of an inhaled antidepressant, such as a heart rate, while an individual 134 is experiencing an artificial sensory experience, such as the social networking site MySpace with a brightened lighting scheme. In this embodiment, acquired data including an increased heart rate may be reported to a medical professional administering the artificial sensory experience to the individual 134 by giving the acquired data in the form of a CD. One example regarding a clinical information reporting system may be found in Selker, U.S. Pat. No. 5,277,188, which is incorporated herein by reference. In some instances, reporter module 2030 may include a computer processor.

Operation 3412 illustrates reporting to at least one of a medical professional or a research institution. For example, as shown in FIGS. 18 through 21, institution reporter module 2032 may report a monitored effect to a medical professional, such as a family physician. A medical professional may include at least one person, agency, department, unit, subcontractor, and/or other entity that delivers a health-related service. Some examples of a medical professional may include a physician, a nurse, a psychiatrist, a clinical social worker, a clinical psychologist, support staff, a pharmacist, a therapist, a hospital, and/or a medical insurance professional. In another embodiment, institution reporter module 2032 may report to a research institution. A research institution may include a research laboratory, an academic institution, a private research institution, and/or a commercial entity. Some examples of a research institution may include Oregon Health & Science University (OHSU), Bell Laboratories, SRI International, Boston Biomedical Research Institute (BBRI), and/or the National Institutes of Health (NIH). In one embodiment, data may be reported to a health clinic, which is further discussed in Selker, U.S. Pat. No. 5,277,188. In some instances, institution reporter module 2032 may include a computer processor and/or a communications link.

Operation 3414 illustrates reporting to at least one of a third party account or a law enforcement agency. For example, as shown in FIGS. 18 through 21, third party reporter module 2034 may report to a third party account. A third party may include a person, organization, and/or entity not actively involved in the current method. A third party account may include, for example, an account granting access to a third party by inputting a user name, password, and/or some other identifying information, such as an account number. Some examples of a third party account may include a gaming account, such as a World of Warcraft account, a website account, such as a personal and/or secured website where data may be uploaded or accessed, and/or an account on a networked computer, such as a ftp server account. In one specific embodiment, third party reporter module 2034 may report acquired data, such as at least one monitored effect of an inhaled antianxiety medication, to a World of Warcraft account, which in turn, for example, may be configured to modify an element of an artificial sensory experience. In another embodiment, third party reporter module 2034 may report to a law enforcement agency, such as the Federal Bureau of Investigation (FBI). A law enforcement agency may include an agency and/or agency representative directly and/or indirectly responsible for enforcing the law of a governing body. Some examples of law enforcement agencies may include the Federal Bureau of Investigation (FBI), the New York City Police Department, the Drug Enforcement Administration (DEA), a county sheriff's department and/or a local police detective. In some instances, third party reporter module 2034 may include a computer processor and/or a communications link.

Figure 35:
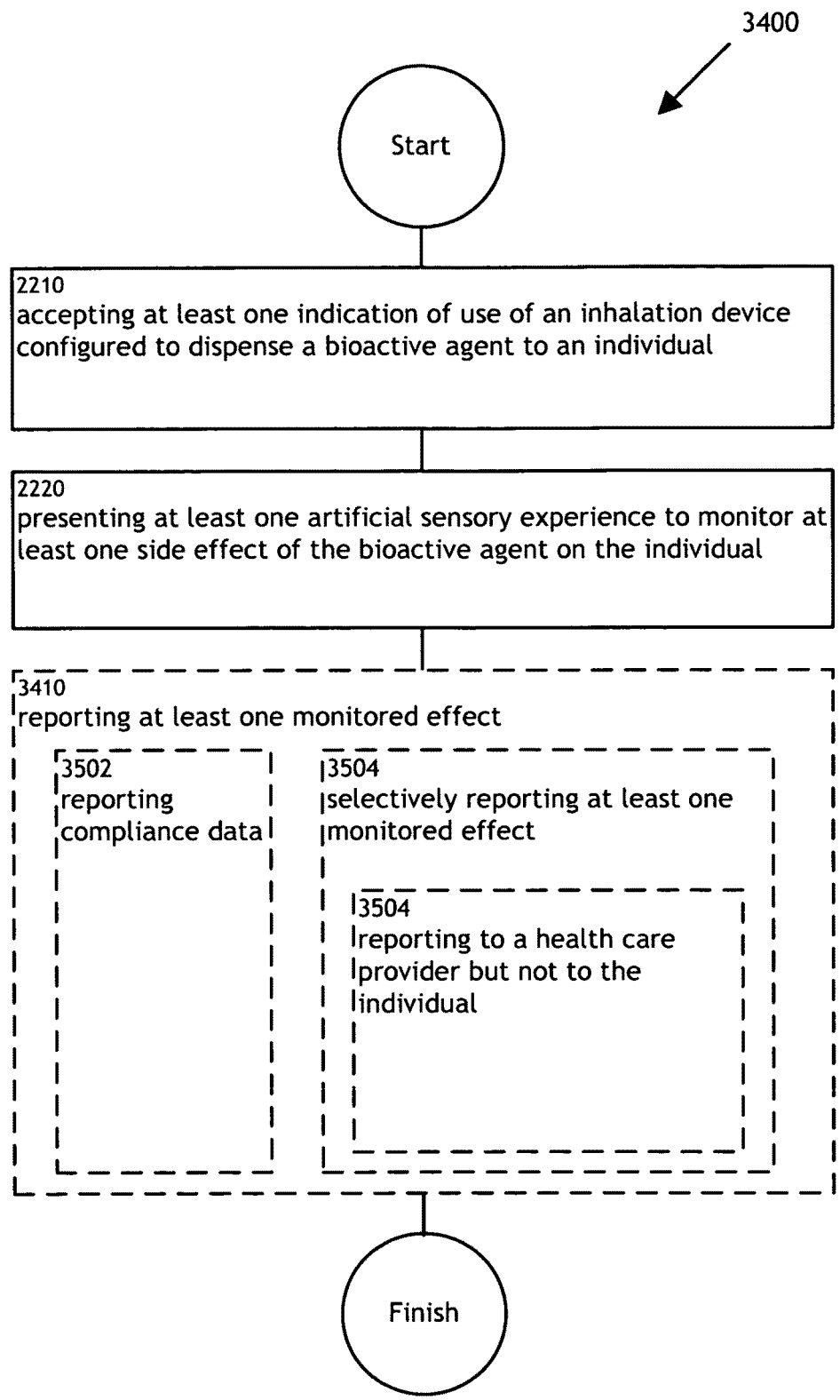
FIG. 35 illustrates an alternative embodiment of the operational flow of FIG. 22.

FIG. 35 illustrates alternative embodiments of the example operational flow 3400 of FIG. 34. FIG. 35 illustrates example embodiments where the operation 3410 may include at least one additional operation. Additional operations may include an operation 3502, an operation 3504, and/or an operation 3506.

Operation 3502 illustrates reporting compliance data. For example, as shown in FIGS. 18 through 21, compliance reporter module 2036 may report compliance data. Compliance data may include data demonstrating adherence to a standard or a regulation, such as, for example, compliance to a physician's prescription. In one embodiment, compliance reporter module 2036 may report whether individual 134 has complied with a physician's prescription to take an inhaled antidepressant by correlating the amount of activity in an artificial sensory experience, such as an amount of avatar interaction by individual 134 in the virtual world Second Life, with efficacy of the inhaled antidepressant. In the current embodiment, a decreased amount of activity by individual 134 in SecondLife may indicate noncompliance with the physician's prescription based on a tendency to be less active socially when depressed. The data, including the indication of noncompliance, may be then reported to an interested party. In some instances, data reporter module 2036 may include a computer processor, a monitor, a mobile device, and/or a printer.

Operation 3504 illustrates selectively reporting at least one monitored effect. For example, as shown in FIGS. 18 through 21, selective reporter module 2038 may selectively report at least one monitored effect. Selective reporting may include limiting and/or blocking access of monitoring results to a specific party. For example, selective reporter module 2038 may report to a physician and not report to the individual 134. Selective reporter module 2038, for example, may report to only a third party. In another example, selective reporter module 2038 may report results only to individual 134. In one embodiment, selective reporter module 2038 may report to a law enforcement agency but not to an individual 134 data indicating the use of an illegal substance. In some instances, selective reporter module 2038 may include a computer processor.

Further, operation 3506 illustrates reporting to a health care provider but not to the individual. For example, as shown in FIGS. 18 through 21, health care provider reporter module 2040 may report to a health care provider but not to the individual. A health care provider may include a hospital, a doctor, a nurse, a medical clinic, a dentist, and/or any provider of preventive, diagnostic, therapeutic, rehabilitative, maintenance, or palliative care and/or counseling. Additionally, a healthcare provider may include a seller and/or dispenser of prescription drugs or medical devices. In one embodiment, health care provider reporter module 2040 may report to a physician and a hospital results from administering an antidepressant to an individual 134, assigning time spent on a social networking website, and monitoring the intensity of a desired effect of the bioactive agent on the individual 134, such as an increased disposition. In the current embodiment, an increased disposition may indicate that an antidepressant medication is effective when coupled with the social networking website. In some instances, health care provider reporter module 2040 may include a computer processor.

Figure 36:
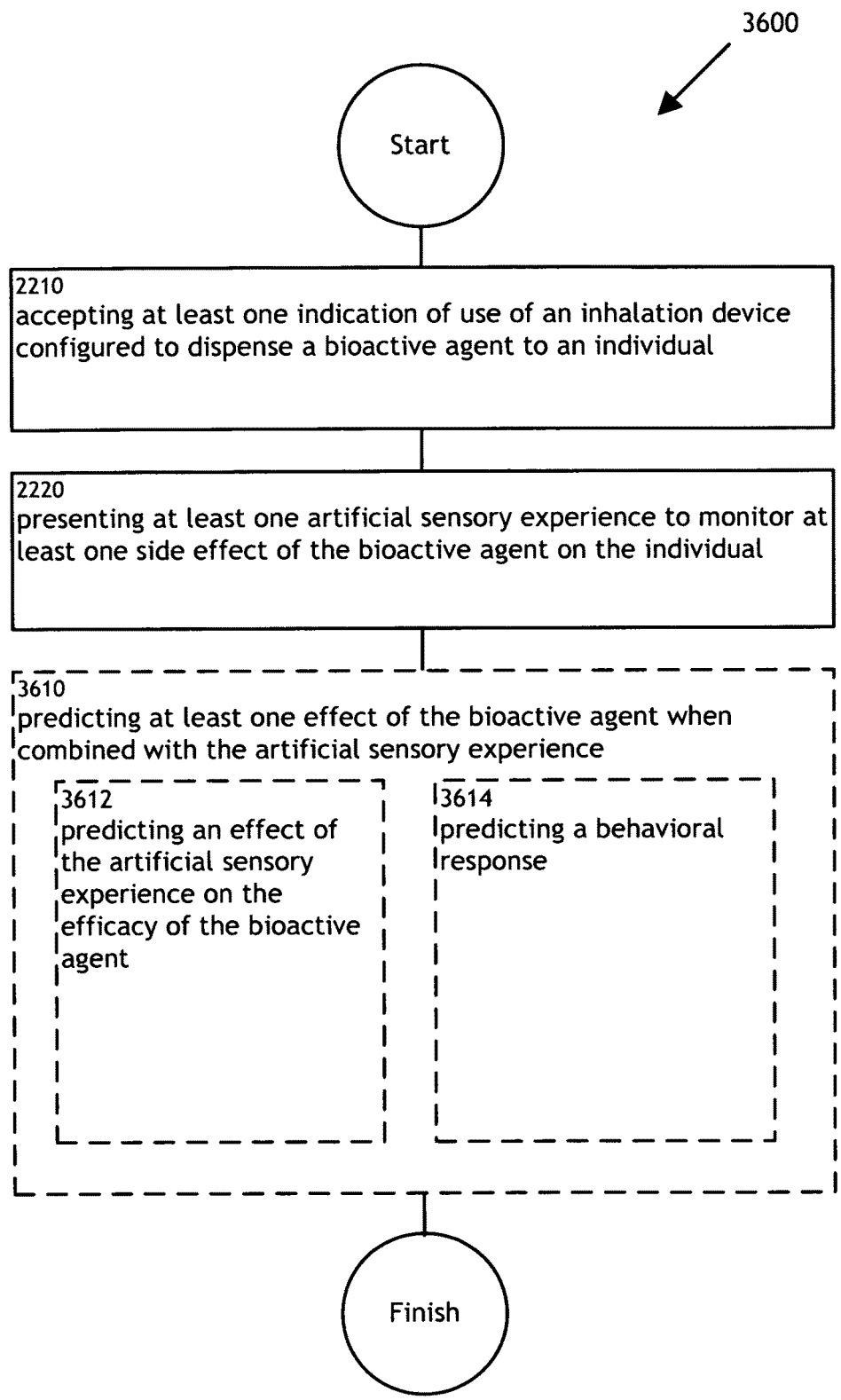
FIG. 36 illustrates an alternative embodiment of the operational flow of FIG. 22.

FIG. 36 illustrates an operational flow 3600 representing example operations related to accepting at least one indication of use of an inhalation device configured to dispense a bioactive agent to an individual, presenting at least one artificial sensory experience to monitor at least one side effect of the bioactive agent on the individual, and predicting at least one effect of the bioactive agent when combined with the artificial sensory experience. FIG. 36 illustrates an example embodiment where the example operational flow 2200 of FIG. 22 may include at least one additional operation. Additional operations may include operation 3610, operation 3612, and/or operation 3614.

After a start operation, operation 2210, and operation 2220, the operational flow 3600 moves to operation 3610. Operation 3610 illustrates predicting at least one effect of the bioactive agent when combined with the artificial sensory experience. For example, as shown in FIGS. 18 through 21, predictor module 2042 may predict an effect of the bioactive agent, such as a higher Wii game score after being administered an inhaled antidepressant medication, when combined with the artificial sensory experience, such as a Wii sports game. Predicting an effect may, for example, include utilizing a mathematical model, prediction software, an algorithm, and/or a statistical model. In one embodiment, predictor module 2042 may predict a decrease in activity in an artificial sensory experience, such as troll-killing in World of Warcraft, when an individual 134 is administered a bioactive agent, such as an inhaled antianxiety medication. In the current embodiment, predictor module 2042 may arrive at a certain prediction by utilizing empirical data and comparing the empirical data with characteristics of the individual 134. Other examples of prediction may be found in Jokiniitty, J. M. et al., *Prediction of blood pressure level and need for antihypertensive medication: 10 years of follow-up*, J HYPERTENSION, 19(7):1193-201 (2001); Yamada, K. et al., *Prediction of medication noncompliance in outpatients with schizophrenia: 2-year follow-up study*, PSYCHIATRY RESEARCH, 141(1):61-69 (2004); and Parker, G. et al., *Prediction of response to antidepressant medication by a sign-based index of melancholia*, AUSTRALIAN AND NEW ZEALAND JOURNAL OF PSYCHIATRY, 27(1):56-61 (1993); each being incorporated herein by reference. In some instances, predictor module 2042 may include a computer processor.

Operation 3612 illustrates predicting an effect of the artificial sensory experience on the efficacy of the bioactive agent. For example, as shown in FIGS. 18 through 21, effect predictor module 2044 may predict an effect of the artificial sensory experience, such as a background color modification and the addition of calming music, on the efficacy of the bioactive agent. In one embodiment, effect predictor module 2044 may predict that the addition of uptempo music and bright background colors to a social networking website enhances the efficacy of an inhaled antidepressant. Effect predictor module 2044 may predict whether an artificial sensory experiment effect improves and/or decreases a bioactive agent efficacy by utilizing and comparing empirical data and characteristics of an individual 134, as described above. Further discussion of music effects may be found in Schellenberg, E. G. et al., *Exposure to music and cognitive performance: tests of children and adults*, PSYCHOLOGY OF MUSIC, Vol. 35, No. 1, 5-19 (2007), incorporated herein by reference. Discussion regarding the effects of color and/or light on nonvisual psychological processes may be found in Knez, *Effects of colour of light on nonvisual psychological processes*, JOURNAL OF ENVIRONMENTAL PSYCHOLOGY, 21(2):201-208 (2001); M. R Basso Jr., *Neurobiological relationships between ambient lighting and the startle response to acoustic stress in humans*, INT J NEUROSCI., 110(3-4):147-57 (2001), and Lam et al., *The Can-SAD Study: a randomized controlled trial of the effectiveness of light therapy and fluoxetine in patients with winter seasonal affective disorder*, AMERICAN JOURNAL OF PSYCHIATRY, 163(5):805-12 (2006), each incorporated by reference.

Other methods for predicting an effect of the artificial sensory experience on the efficacy of the bioactive agent may include trend estimation, regression analysis, and or data extrapolation. In one embodiment, effect predictor module 2044 may utilize trend estimation to predict an effect of the artificial sensory experience, such as a snowy environment in a virtual world, on the efficacy of the bioactive agent, such as an analgesic. Trend estimation may include the application of statistics to make predictions about trends in data using previously measured data utilizing methods which may include, for example, the method of least squares, an R-squared fit, and a trend plus noise method. An additional example may be found in Greenland, S. et al., *Methods for Trend Estimation from Summarized Dose-Response Data, with Applications to Meta-Analysis*, AM. J. EPIDEMIOL., 135(11):1301-09 (1992), which is incorporated herein by reference.

In another embodiment, effect predictor module 2044 may utilize regression analysis to predict an effect of the artificial sensory experience, such as a snowy environment in a virtual world, on the efficacy of the bioactive agent, such as an analgesic. Regression analysis may include statistical technique for determining the best mathematical expression describing the functional relationship between one response, such as efficacy of the bioactive agent, and one or more independent variables, for example, an effect of the artificial sensory experience. A further discussion of regression analysis may be found in Matthews D. E. and Farewell V. T., *Using and Understanding Medical Statistics*, Basel, S. Karger A. G., 2007, which is incorporated herein by reference.

In another embodiment, effect predictor module 2044 may utilize data extrapolation to predict an effect of the artificial sensory experience, such as a snowy environment in a virtual world, on the efficacy of the bioactive agent, for example an analgesic. Data extrapolation may include the process of constructing new data points outside a discrete set of known data points. For example, a bioagent's efficacy may be predicted by using and/or comparing previous measurements of an artificial sensory experience effect on a bioagent's efficacy using a population with similar characteristics as individual 134. One example using a data extrapolation algorithm may be found in Smith, M. R., et al., *A data extrapolation algorithm using a complex domain neuralnetwork*, IEEE TRANSACTIONS ON CIRCUITS AND SYSTEMS II: ANALOG AND DIGITAL SIGNAL PROCESSING, 44(2):143-47 (1997), which is incorporated herein by reference. In some instances, effect predictor module 2044 may include a computer processor.

Operation 3614 illustrates predicting a behavioral response. For example, as shown in FIGS. 18 through 21, behavioral response predictor module 2046 may predict a behavioral response. In one embodiment, behavioral response predictor module 2046 may predict an increased score in an artificial sensory experience, such as a Wii Sports game, when an individual is administered an inhaled antidepressant. In this embodiment, the administration of an inhaled antidepressant may serve to heighten the mood of an individual 134 and increase a desire to be competitive while experiencing an artificial sensory experience. Behavioral response predictor module 2046 may predict using methods described above, such as using empirical data and regression analysis, trend estimation, and or data extrapolation. Other examples of a behavioral response may include a lack of ability to concentrate while experiencing acute stress and/or flinching when exposed to a loud sound and/or loud acoustics. In some instances, behavioral response predictor module 2046 may include a computer processor.

Figure 37:
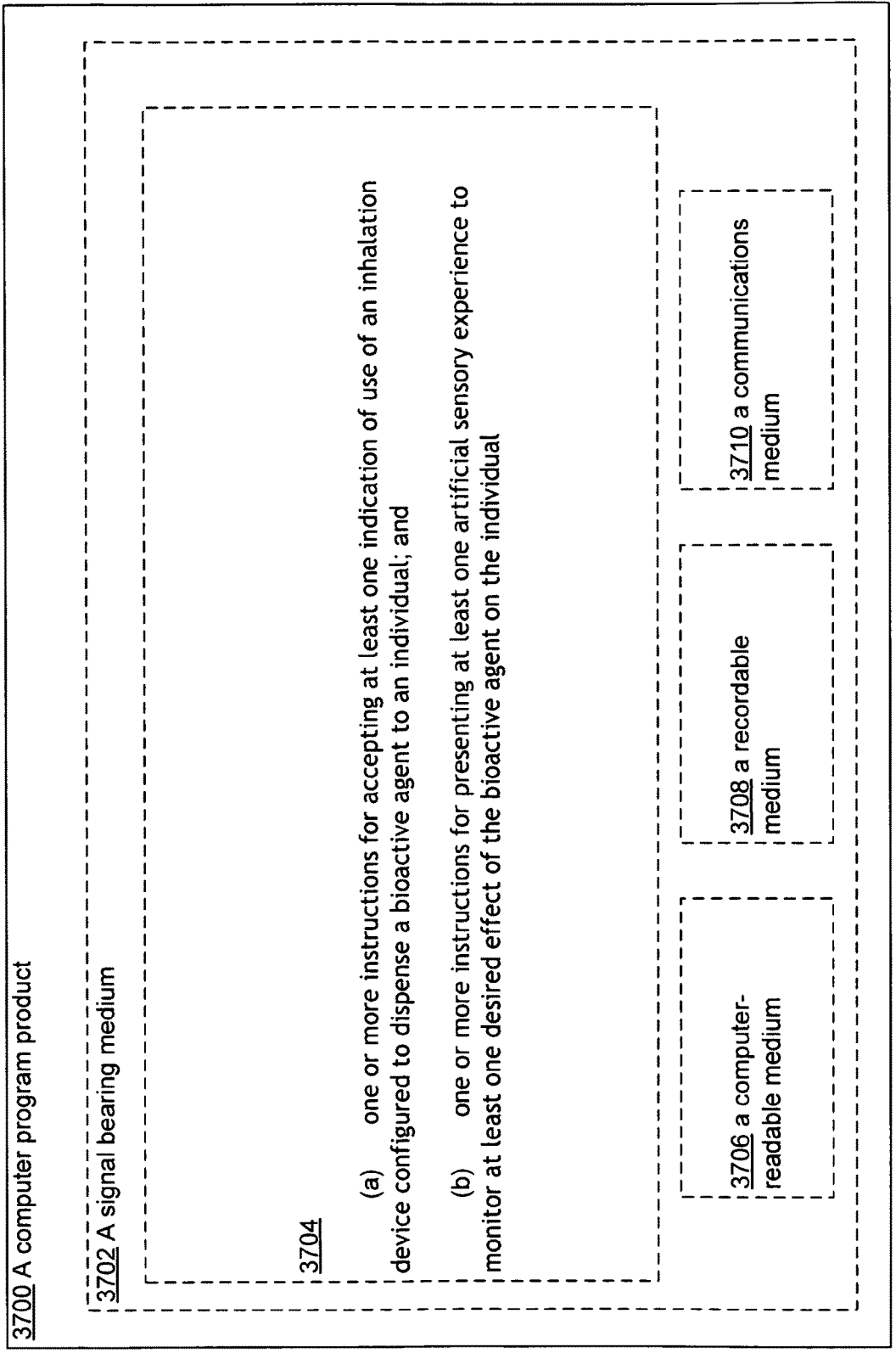
FIG. 37 illustrates a computer program product related to combining an inhaled bioactive agent and an artificial sensory experience.

FIG. 37 illustrates a partial view of an example computer program product 3700 that includes a computer program 3704 for executing a computer process on a computing device. An embodiment of the example computer program product 3700 is provided using a signal-bearing medium 3702, and may include one or more instructions for accepting at least one indication of use of an inhalation device configured to dispense a bioactive agent to an individual and one or more instructions for presenting at least one artificial sensory experience to monitor at least one side effect of the bioactive agent on the individual. The one or more instructions may be, for example, computer executable and/or logic-implemented instructions. In one implementation, the signal-bearing medium 3702 may include a computer-readable medium 3706. In one implementation, the signal bearing medium 3702 may include a recordable medium 3708. In one implementation, the signal bearing medium 3702 may include a communications medium 3710.

Figure 38:
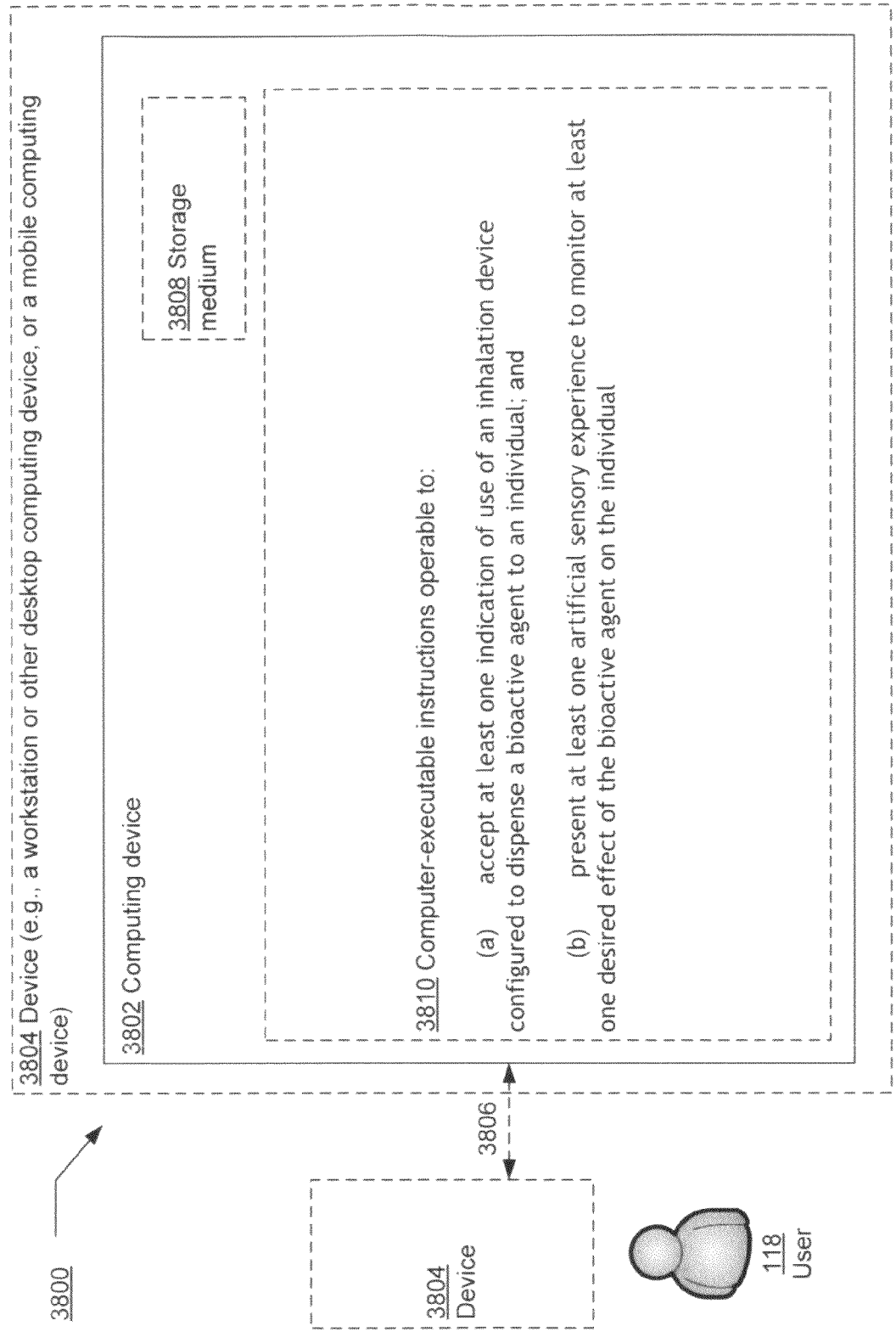
FIG. 38 illustrates a system related to combining an inhaled bioactive agent and an artificial sensory experience.

FIG. 38 illustrates an example system 3800 in which embodiments may be implemented. The system 3800 includes a computing system environment. The system 3800 also illustrates the user 118 using a device 3804, which is optionally shown as being in communication with a computing device 3802 by way of an optional coupling 3806. The optional coupling 3806 may represent a local, wide-area, or peer-to-peer network, or may represent a bus that is internal to a computing device (e.g., in example embodiments in which the computing device 3802 is contained in whole or in part within the device 3804). A storage medium 3808 may be any computer storage media.

The computing device 3802 includes computer-executable instructions 3810 that when executed on the computing device 3802 cause the computing device 3802 to accept at least one indication of use of an inhalation device configured to dispense a bioactive agent to an individual and present at least one artificial sensory experience to monitor at least one side effect of the bioactive agent on the individual. As referenced above and as shown in FIG. 38, in some examples, the computing device 3802 may optionally be contained in whole or in part within the device 3804.

In FIG. 38, then, the system 3800 includes at least one computing device (e.g., 3802 and/or 3804). The computer-executable instructions 3810 may be executed on one or more of the at least one computing device. For example, the computing device 3802 may implement the computer-executable instructions 3810 and output a result to (and/or receive data from) the computing device 3804. Since the computing device 3802 may be wholly or partially contained within the computing device 3804, the device 3804 also may be said to execute some or all of the computer-executable instructions 3810, in order to be caused to perform or implement, for example, various ones of the techniques described herein, or other techniques.

The device 3804 may include, for example, a portable computing device, workstation, or desktop computing device. In another example embodiment, the computing device 3802 is operable to communicate with the device 3804 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also tends itself well to modular and/or object-oriented program design paradigms.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction Left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in tight of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art wilt also appreciate that examples of electromechanical systems include but are not limited to a variety of consumer electronics systems, medical devices, as well as other systems such as motorized transport systems, factory automation systems, security systems, and/or communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are Located and/or used outside the territory.

Further, implementation of at Least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user 118 is shown/described herein as a single illustrated figure, those skilled in the art will appreciate that user 118 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art wilt recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at Least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments wilt be apparent to those skilled in the art. The various aspects and embodiments disclosed herein are for purposes of illustration and are not intended to be limiting, with the true scope and spirit being indicated by the following claims.

What is claimed is:

1. A system, comprising:
   means for accepting at least one indication of use of an inhalation device configured to dispense a bioactive agent to an individual;
   means for presenting at least one virtual reality experience, including at least one virtual reality device, configured to monitor at least one effect of the bioactive agent on the individual, the monitoring operable to predict the at least one effect of the bioactive agent on the individual;
   means for reporting the at least one effect of the bioactive agent to a user; and
   means for accepting at least some input from the user, the input operable to modify at least one element of the at least one virtual reality experience.

2. The system of claim 1 wherein the means for accepting at least one indication of use of an inhalation device configured to dispense a bioactive agent to an individual comprises:
   means for accepting an indication of a bioactive agent-dispensing inhalation device configured to interface with a computing device.

3. The system of claim 2 wherein the means for accepting an indication of a bioactive agent-dispensing inhalation device configured to interface with a computing device comprises:
   means for accepting an indication of a bioactive agent-dispensing inhalation device configured to interface wirelessly with a computing device.

4. The system of claim 1 wherein the means for accepting at least one indication of use of an inhalation device configured to dispense a bioactive agent to an individual comprises:
   means for accepting an indication of a bioactive agent-dispensing inhalation collar.

5. The system of claim 1 wherein the means for accepting at least one indication of use of an inhalation device configured to dispense a bioactive agent to an individual comprises:
   means for accepting an indication of a bioactive agent-dispensing virtual-reality headset.

6. The system of claim 5, wherein the means for accepting an indication of a bioactive agent-dispensing virtual-reality headset comprises:
   means for accepting at least one of a bioactive agent dosing schedule or a bioactive agent administration schedule.

7. The system of claim 1 wherein the means for accepting at least one indication of use of an inhalation device configured to dispense a bioactive agent to an individual comprises:
   means for accepting an indication of a medication-dispensing inhalation device.

8. The system of claim 7, wherein the means for accepting an indication of a medication-dispensing inhalation device comprises:
   means for accepting an indication of a prescription medication-dispensing inhalation device.

9. The system of claim 1 wherein the means for accepting at least one indication of use of an inhalation device configured to dispense a bioactive agent to an individual comprises:
   means for accepting an indication of an unregulated bioactive agent-dispensing inhalation device.

10. The system of claim 1 wherein the means for accepting at least one indication of use of an inhalation device configured to dispense a bioactive agent to an individual comprises:
   means for accepting an indication of a recreational bioactive agent-dispensing inhalation device.

11. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for receiving data from an automated medical device.

12. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for presenting a sensate experience.

13. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for presenting at least one virtual reality experience implemented on a mobile device.

14. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for presenting at least one of an artificial sensory experience, a virtual world, a modification to a virtual world, a computer game, a modification to a computer game, a website, a modification to a website, an online course, or a modification to an online course.

15. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for presenting at least one virtual reality experience to monitor at least one of physical activity, body weight, body mass index, heart rate, blood oxygen level, or blood pressure temporally associated with an artificial sensory experience.

16. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for presenting at least one virtual reality experience to monitor a neurophysiological measurement.

17. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for measuring at least one brain activity surrogate marker.

18. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for presenting at least one virtual reality experience to measure at least one effect of the bioactive agent in at least one of near real time or real time.

19. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for monitoring at least one of visual field test function output, eye movement test function output, pupil movement test function output, face pattern test function output, hearing test function output, or voice test function output.

20. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for monitoring at least one of body movement test function output or motor skill test function output.

21. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for recording at least one monitored effect of the bioactive agent.

22. The system of claim 1, wherein the means for accepting at least one indication of use of an inhalation device configured to dispense a bioactive agent to an individual and the means for presenting at least one virtual reality experience, including at least one virtual reality device, configured to monitor at least one effect of the bioactive agent on the individual, the monitoring operable to predict the at least one effect of the bioactive agent on the individual comprise:
   means for accepting an indication of a collar configured to dispense a bronchodilator to an individual and presenting at least one virtual reality experience to monitor an individual's hypertension in response to administration of the bronchodilator.

23. The system of claim 1, further comprising:
   means for reporting at least one monitored effect.

24. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:
   means for predicting at least one effect of the bioactive agent when combined with the at least one virtual reality experience.

25. The system of claim 1, wherein the means for accepting at least one indication of use of an inhalation device configured to dispense a bioactive agent to an individual, the means for presenting at least one virtual reality experience, including at least one virtual reality device, configured to monitor at least one effect of the bioactive agent on the individual, the monitoring operable to predict the at least one effect of the bioactive agent on the individual, the means for reporting the at least one effect of the bioactive agent to a user, and the means for accepting at least some input from the user, the input operable to modify at least one element of the virtual reality experience comprise:

means for accepting at least one indication of a patient's compliance with a physician's prescription via at least the patient utilizing a virtual reality helmet configured to dispense an inhaled medication, the helmet utilized by the patient to participate in a World of Warcraft game while receiving an inhaled prescribed antidepressant medication;

means for presenting the World of Warcraft game to monitor the patient's troll-killing in World of Warcraft, the monitoring of the patient's troll-killing operable to predict a current level of depression in the patient based at least in part on the prescribed antidepressant medication;

means for reporting the monitored effect to the physician; and means for accepting at least some input from the physician, the input operable to modify at least one level of the prescribed antidepressant medication responsive to the predicted current level of depression in the individual.

26. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual and the means for accepting at least some input from the user, the input operable to modify at least one element of the virtual reality experience comprise:

means for predicting at least one level of depression via at least monitoring at least some social networking activity of the individual; and means for at least partially altering the efficacy of an inhaled antidepressant medication via at least alteration of a background color or music of the social networking website by the user.

27. The system of claim 1, wherein the means for presenting at least one virtual reality experience, including at least one virtual reality device, configured to monitor at least one effect of the bioactive agent on the individual, the monitoring operable to predict the at least one effect of the bioactive agent on the individual comprises:

means for presenting at least one virtual reality experience to monitor at least one bioactive agent, wherein one or more of the at least one virtual reality experience or the at least one bioactive agent is associated with a central nervous system condition.

28. The system of claim 1, wherein the means for presenting at least one virtual reality experience, including via at least one virtual reality device, configured to monitor at least one effect of the bioactive agent on the individual, the monitoring operable to predict the at least one effect of the bioactive agent on the individual comprises:

means for presenting at least one of an artificial sensory experience, a sensate experience, a virtual world, a massively multiplayer online game, a learning tutorial, a computer-based simulated environment, a text-based chat room, a picture chat, an instant messaging application, an online class, an internet marketplace, a computer conferencing, an online game, a single player game, a networked game, a video game, an interactive experience including at least a religious ceremony, an interactive experience including at least a combat training exercise, a screen recording, a written document, an audio file, a virtual scent environment, an interactive experience including at least a secular ceremony, a social networking environment, an online learning environment, an online educational experience, an online shopping environment, or an online medical information environment.

29. A method, comprising:

accepting at least one indication of use of an inhalation device configured to dispense a bioactive agent to an individual;

presenting at least one virtual reality experience, including via at least one virtual reality device, configured to monitor at least one effect of the bioactive agent on the individual, the monitoring operable to predict the at least one effect of the bioactive agent on the individual;

reporting the at least one effect of the bioactive agent to a user; and accepting at least some input from the user, the input operable to modify at least one element of the at least one virtual reality experience.

30. A system, comprising:

circuitry for accepting at least one indication of use of an inhalation device configured to dispense a bioactive agent to an individual; and circuitry for presenting at least one virtual reality experience, including at least one virtual reality device, configured to monitor at least one effect of the bioactive agent on the individual, the monitoring operable to predict the at least one effect of the bioactive agent on the individual;

circuitry for reporting the at least one effect of the bioactive agent to a user; and circuitry for accepting at least some input from the user, the input operable to modify at least one element of the at least one virtual reality experience.

31. A computer program product, comprising:

at least one non-transitory computer readable medium including at least:

one or more instructions for accepting at least one indication of use of an inhalation device configured to dispense a bioactive agent to an individual;

one or more instructions for presenting at least one virtual reality experience, including via at least one virtual reality device, configured to monitor at least one effect of the bioactive agent on the individual, the monitoring operable to predict the at least one effect of the bioactive agent on the individual;

one or more instructions for reporting the at least one effect of the bioactive agent to a user; and one or more instructions for accepting at least some input from the user, the input operable to modify at least one element of the at least one virtual reality experience.

32. A system comprising:

a computing device; and at least some instructions that when executed on the computing device cause the computing device to accept at least one indication of use of an inhalation device configured to dispense a bioactive agent to an individual;

present at least one virtual reality experience, including via at least one virtual reality device, configured to monitor at least one effect of the bioactive agent on the individual, the monitoring operable to predict the at least one effect of the bioactive agent on the individual;

report the at least one effect of the bioactive agent to a user; and accept at least some input from the user, the input operable to modify at least one element of the at least one virtual reality experience.

33. The system of claim 32 wherein the computing device comprises:
one or more of a personal digital assistant (PDA), a personal entertainment device, a mobile phone, a laptop computer, a tablet personal computer, a networked computer, a computing system comprised of a cluster of processors, a computing system comprised of a cluster of servers, a workstation computer, and/or a desktop computer.

34. The system of claim 32, wherein the computing device is operable to accept the at least one attribute of the at least one individual and present the indication of the at least one prescription medication and the at least one artificial sensory experience from at least one memory.

* * * * *